United States Patent
Deng et al.

(10) Patent No.: US 11,312,701 B2
(45) Date of Patent: Apr. 26, 2022

(54) FORMYLPYRIDINE DERIVATIVE HAVING FGFR4 INHIBITORY ACTIVITY, PREPARATION METHOD THEREFOR AND USE THEREOF

(71) Applicant: Abbisko Therapeutics Co., Ltd., Pudong New Area Shanghai (CN)

(72) Inventors: Haibing Deng, Pudong New Area Shanghai (CN); Fei Yang, Pudong New Area Shanghai (CN); Hongping Yu, Pudong New Area Shanghai (CN); Zhui Chen, Pudong New Area Shanghai (CN); Yaochang Xu, Pudong New Area Shanghai (CN)

(73) Assignee: ABBISKO THERAPEUTICS CO., LTD, Shanghai (CN)

(*) Notice: Subject to any disclaimer, the term of this patent is extended or adjusted under 35 U.S.C. 154(b) by 8 days.

(21) Appl. No.: 16/633,254

(22) PCT Filed: Aug. 1, 2018

(86) PCT No.: PCT/CN2018/098078
§ 371 (c)(1),
(2) Date: Jan. 23, 2020

(87) PCT Pub. No.: WO2019/024876
PCT Pub. Date: Feb. 7, 2019

(65) Prior Publication Data
US 2021/0130323 A1 May 6, 2021

(30) Foreign Application Priority Data
Aug. 4, 2017 (CN) .......................... 201710661244.8

(51) Int. Cl.
| | | |
|---|---|---|
| C07D 401/14 | (2006.01) | |
| A61P 35/00 | (2006.01) | |
| C07D 405/14 | (2006.01) | |
| C07D 413/14 | (2006.01) | |
| C07D 491/107 | (2006.01) | |

(52) U.S. Cl.
CPC ............ *C07D 401/14* (2013.01); *A61P 35/00* (2018.01); *C07D 405/14* (2013.01); *C07D 413/14* (2013.01); *C07D 491/107* (2013.01)

(58) Field of Classification Search
CPC .. C07D 401/14; C07D 413/14; C07D 401/12; C07D 213/75; A61P 35/00; A61K 31/444; A61K 31/506
See application file for complete search history.

(56) References Cited

U.S. PATENT DOCUMENTS

2006/0235037 A1* 10/2006 Purandare ............ C07D 401/14
514/278
2019/0144427 A1* 5/2019 Kong .................... A61K 31/496
514/235.8

FOREIGN PATENT DOCUMENTS

WO     2016/151499 A1     9/2016
WO     2018010514 A1     1/2018

OTHER PUBLICATIONS

Hagel et al., First Selective Small Molecule Inhibitor of FGFR4 for the Treatment of Hepatocellular Carcinomas with an Activated FGFR4 Signaling Pathway, Cancer Discovery, pp. 424-437 (2015).*
Int'l Search Report dated Nov. 8, 2018 in Int'l Application No. PCT/CN2018/098078.
Extended European Search Report dated Apr. 8, 2021 in EP Application No. 18842293.5.

* cited by examiner

*Primary Examiner* — Deepak R Rao
(74) *Attorney, Agent, or Firm* — Panitch Schwarze Belisario & Nadel LLP

(57) ABSTRACT

Formylpyridine derivatives having FGFR4 inhibitory activities, a preparation method therefor and use thereof are described. In particular, the formylpyridine derivatives have a structure of formula (I), and the definition of each substituent in the formula are described in the description and claims. The series of compounds of the formula (I) have very strong inhibitory effects on FGFR4 kinases and very high selectivity, and can be widely used in the preparation of medicaments for treating cancers, particularly prostate cancer, liver cancer, pancreatic cancer, esophageal cancer, stomach cancer, lung cancer, breast cancer, ovarian cancer, colon cancer, skin cancer, neuroglioblastoma or rhabdomyosarcoma, and prospectively will be further developed to become a new generation of FGFR4 inhibitors.

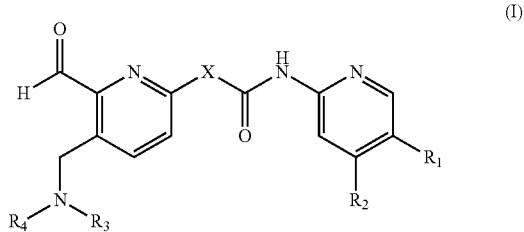

(I)

6 Claims, No Drawings

FORMYLPYRIDINE DERIVATIVE HAVING FGFR4 INHIBITORY ACTIVITY, PREPARATION METHOD THEREFOR AND USE THEREOF

CROSS-REFERENCE TO RELATED APPLICATION

This application is a Section 371 of International Application No. PCT/CN2018/098078, filed Aug. 1, 2018, which was published in the Chinese language on Feb. 7, 2019, under International Publication No. WO 2019/024876 A1, which claims priority under 35 U.S.C. § 119(b) to Chinese Application No. 201710661244.8, filed Aug. 4, 2017, the disclosures of which are incorporated herein by reference in their entirety.

TECHNICAL FIELD

The present invention belongs to the field of medicament synthesis, and in particular relates to formylpyridine derivative having FGFR4 inhibitory activity, preparation method therefor and use thereof

TECHNICAL BACKGROUND

Fibroblast growth factor (FGF) is a family of 22 structurally related polypeptides with diverse biological activities that can regulate cell proliferation, differentiation and migration, and play a major role in the processes such as limb development, angiogenesis, tissue repair, tumor formation and the like.

FGF receptors (FGFRs) belong to a family of RPTK of receptor tyrosine kinases. Four FGFRs, FGFR1, FGFR2, FGFR3 and FGFR4, have been identified to date. The interaction between receptors and the corresponding ligands FGF leads to receptor dimerization and autophosphorylation, thereby initiating multiple downstream signaling cascades including MAPK and AKT.

FGFR1-3 has been found to be overexpressed, mutated or translocated in a variety of tumors (including myeloma, breast cancer, stomach cancer, colon cancer, bladder cancer, pancreatic cancer, and hepatocellular carcinoma), and considered to be driver gene in cancer. Some FGFR inhibitors have also been developed in the clinical and preclinical development process. However, previous studies have shown that FGFR1 can regulate the level of phosphate, so pan-FGFR inhibitors may pose safety concerns.

Hepatocellular carcinoma (HCC) is one of the leading causes of cancer-related deaths in China and is one of the fastest growing cancers every year. Currently, the first-line treatment option is sorafenib, there are no approved second-line treatments, and there is still a need for targeted therapy with anti-tumor agents.

Overexpression of FGF19 is present in 5-10% of hepatocellular carcinoma patients, whereas FGFR4 is a dominant FGFR present in human hepatocytes, and its high expression in hepatocytes is found to be associated with the aggressiveness of hepatocellular tumors. Therefore, FGFR4 plays a very important role in liver cancer. In addition, the interaction of FGF19 and FGFR4 is also considered to be related to the aggressiveness of other cancers (such as gastric cancer, prostate cancer, lung cancer, colorectal cancer, pancreatic cancer, and ovarian cancer).

At present, some FGFR inhibitors have entered into the clinical research stage as anti-tumor drugs, but mostly inhibitors against FGFR1, 2 and 3, with weaker inhibition of FGFR4 activity. The inhibition of FGFR1-3 has on-target side effects such as hyperphosphatemia. Highly selective inhibitor of FGFR4 can effectively treat cancer caused by abnormal FGFR4 signaling, and can avoid the side effects caused by FGFR-3 inhibition such as hyperphosphatemia. Highly selective small molecule inhibitors against FGFR4 have significant application prospects in the field of anti-tumor targeted therapy. Therefore, the development of a novel anti-tumor agent that can selectively target FGFR4 as a good drug candidate will meet the needs of domestic liver cancer and other anti-tumor target therapy, and have the advantages of better safety and higher selectivity.

SUMMARY OF THE INVENTION

An object of the present invention is to provide an FGFR4 inhibitor, preparation method and pharmaceutical use thereof.

The first aspect of the invention provides a compound of formula (I), a stereoisomer or pharmaceutically acceptable salt thereof:

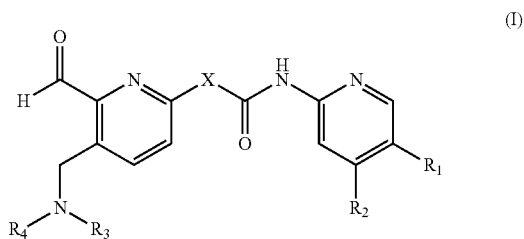

wherein, X is —N($R_5$)— or —C($R_6R_7$)—;

$R_1$ is selected from the group consisting of hydrogen, deuterium, halogen, cyano, nitro, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_9$, —$C_{0-8}$—O—$R_{10}$, —$C_{0-8}$—C(O)$R_{11}$, —$C_{0-8}$—N$R_{12}R_{13}$, —$C_{0-8}$—C(O)N$R_{12}R_{13}$ and —$C_{0-8}$—N($R_{12}$)—C(O)$R_{11}$, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —$C_{0-8}$—N($R_{12}$)—C(O)$R_{11}$ and —$C_{0-8}$—N($R_{12}$)—C(O)O$R_{10}$, above groups are further more optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —$C_{0-8}$—N($R_{12}$)—C(O)$R_{11}$ and —$C_{0-8}$—N($R_{12}$)—C(O)O$R_{10}$;

$R_2$ is selected from the group consisting of hydrogen, deuterium, halogen, cyano, nitro, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —$C_{0-8}$—N($R_{12}$)—C(O)$R_{11}$ and —$C_{0-8}$—N($R_{12}$)—C(O)O$R_{10}$, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$, above groups are further more optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$;

$R_3$ and $R_4$ are each independently selected from the group consisting of hydrogen, deuterium, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=NR$_8$)R$_9$, —$C_{0-8}$—P(O)(R$_9$)$_2$, —$C_{0-8}$—S(O)R$_9$, —$C_{0-8}$—S(O)$_2$R$_9$, —$C_{0-8}$—C(O)OR$_{10}$, —$C_{0-8}$—C(O)R$_{11}$, —$C_{0-8}$—NR$_{12}$R$_{13}$, —$C_{0-8}$—C(O)NR$_{12}$R$_{13}$ and —$C_{0-8}$—N(R$_{12}$)—C(O)R$_{11}$, or, $R_3$ and $R_4$ together with the nitrogen atom directly attached thereto, form a 3-10 membered heterocyclyl or 5-10 membered heteroaryl, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, =O, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$;

$R_5$ is selected from the group consisting of hydrogen, deuterium $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl and 5-10 membered heteroaryl, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$;

$R_6$ and $R_7$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$, or, $R_6$ and $R_7$, together with the carbon atom directly attached thereto, form a C(O), $C_{3-10}$ cycloalkyl or 3-10 membered heterocyclyl, above groups are further more optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$;

each $R_8$ is independently selected from the group consisting of hydrogen, deuterium, $C_{1-8}$ alkyl, $C_{3-10}$ cycloalkylC$_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —$C_{0-8}$—N(R$_{12}$)—C(O)R$_{11}$ and —$C_{0-8}$—N(R$_{12}$)—C(O)OR$_{10}$;

each $R_9$ is independently selected from the group consisting of hydrogen, deuterium, hydroxy, $C_{1-8}$ alkyl, $C_{1-8}$ alkoxy, $C_{2-8}$ alkenyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{12}$R$_{13}$, above groups are further optionally substituted by one or more substituents selected from the group consisting of deuterium, halogen, hydroxy, =O, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{12}$R$_{13}$;

each $R_{10}$ is independently selected from the group consisting of hydrogen, deuterium, $C_{1-8}$ alkyl, $C_{2-8}$ alkenyl, $C_{3-10}$ cycloalkyl, 3-10 membered heterocyclyl, $C_{5-10}$ aryl and 5-10 membered heteroaryl, above groups are further optionally substituted by one or more substituents selected from the group consisting of deuterium, halogen, hydroxy, carbonyl, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{12}$R$_{13}$, above groups are further more optionally substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

each $R_{11}$ is independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{12}$R$_{13}$, above groups are further optionally substituted by one or more substituents selected from the group consisting of deuterium, halogen, hydroxy, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{12}R_{13}$;

each $R_{12}$ and each $R_{13}$ are each independently selected from the group consisting of hydrogen, deuterium, hydroxy, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, sulfonyl, methylsulfonyl, isopropylsulfonyl, cyclopropylsulfonyl, p-toluenesulfonyl, amino, monoalkylamino, dialkylamino and $C_{1-8}$ alkanoyl, above groups are further optionally substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl, above groups are further more optionally substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

or, $R_{12}$ and $R_{13}$, together with the nitrogen atom directly attached thereto, form a 3-10 membered heterocyclyl, above groups are further optionally substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{3-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

each r is independently 0, 1 or 2.

In a preferred embodiment, in the said compound of formula (I), the stereoisomer or pharmaceutically acceptable salt thereof, $R_1$ is selected from the group consisting of hydrogen, deuterium, halogen, cyano, nitro, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—$S(O)_rR_9$, —$C_{0-8}$—O—$R_{10}$, —$C_{0-8}$—$C(O)R_{11}$, —$C_{0-8}$—$NR_{12}R_{13}$, —$C_{0-8}$—$C(O)NR_{12}R_{13}$ and —$C_{0-8}$—N($R_{12}$)—$C(O)R_{11}$, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—$S(O)_rR_9$, —$C_{0-4}$—O—$R_{10}$, —$C_{0-4}$—$C(O)OR_{10}$, —$C_{0-4}$—$C(O)R_{11}$, —$C_{0-4}$—O—$C(O)R_{11}$, —$C_{0-4}$—$NR_{12}R_{13}$, —$C_{0-4}$—$C(O)NR_{12}R_{13}$, —$C_{0-4}$—N($R_{12}$)—$C(O)R_{11}$ and —$C_{0-4}$—N($R_{12}$)—$C(O)OR_{10}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—$S(O)_rR_9$, —$C_{0-4}$—O—$R_{10}$, —$C_{0-4}$—$C(O)OR_{10}$, —$C_{0-4}$—$C(O)R_{11}$, —$C_{0-4}$—O—$C(O)R_{11}$, —$C_{0-4}$—$NR_{12}R_{13}$, —$C_{0-4}$—$C(O)NR_{12}R_{13}$, —$C_{0-4}$—N($R_{12}$)—$C(O)R_{11}$ and —$C_{0-4}$—N($R_{12}$)—$C(O)OR_{10}$.

In a more preferred embodiment, in the said compound of formula (I), the stereoisomer or pharmaceutically acceptable salt thereof, $R_1$ is selected from deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—$S(O)_rR_9$, —$C_{0-4}$—O—$R_{10}$, —$C_{0-4}$—$NR_{12}R_{13}$ and —$C_{0-4}$—$C(O)NR_{12}R_{13}$, above groups are further optionally substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, —$C_{0-4}$—O—$R_{10}$ and —$C_{0-4}$—$NR_{12}R_{13}$, above groups are further more optionally substituted by one or more substituents selected from deuterium, halogen, $C_{3-10}$ cycloalkyl, 3-6 membered heterocyclyl, —$C_{0-4}$—O—$R_{10}$, —$C_{0-4}$—O—$C(O)R_{11}$ and —$C_{0-4}$—$NR_{12}R_{13}$.

In a further preferred embodiment, in the compound of formula (I), the stereoisomer or pharmaceutically acceptable salt thereof, $R_1$ is selected from the group consisting of deuterium, halogen, cyano, methyl, ethynyl, cyclopropyl, cyclopentyl, oxa-cyclobutyl, aza-cyclohexyl, morpholinyl, $C_{5-6}$ aryl, 5-6 membered heteroaryl, methoxy, ethoxy, tert-butoxyl, amino, methylamino, dimethylamino, aminoacyl, dimethylaminoacyl, methylthio, sulfonyl and methylsulfonyl, above groups are further optionally substituted by one or more substituents selected from the group consisting of deuterium, fluorine, chlorine, methyl, isopropyl, tert-butyl, cyclopropyl, cyclopentyl, oxa-cyclobutyl, aza-cyclohexyl, morpholinyl, methoxy, ethoxy, tert-butoxyl, hydroxy, amino, methylamino and dimethylamino, above groups are further more optionally substituted by one or more substituents selected from the group consisting of deuterium, fluorine, chlorine, cyclopropyl, cyclopentyl, oxa-cyclobutyl, hydroxy, methoxy and amino.

In a preferred embodiment, in the compound of formula (I), the stereoisomer or pharmaceutically acceptable salt thereof, $R_3$ and $R_4$ are each independently selected from the group consisting of hydrogen, deuterium, $C_{1-4}$ alkyl, $C_{3-8}$ cycloalkyl, 3-8 membered heterocyclyl, $C_{5-8}$ aryl, 5-8 membered heteroaryl, —$C_{0-8}$—$C(O)R_{11}$ and —$C_{0-8}$—$C(O)NR_{12}R_{13}$, or, $R_3$ and $R_4$. together with the nitrogen atom directly attached thereto form a 3-8 membered heterocyclyl, or 5-8 membered heteroaryl, above groups are further optionally substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, —$C_{0-4}$—O—$R_{10}$ and —$C_{0-4}$—$NR_{12}R_{13}$.

In a further preferred embodiment, in the compound of formula (I), the stereoisomer or pharmaceutically acceptable salt thereof, $R_3$ is selected from the group consisting of hydrogen, deuterium, methyl, ethyl, isopropyl, hydroxymethyl, methoxymethyl, methoxyethyl, cyclopropyl, cyclopropylmethyl, oxa-cyclobutyl, trifluoromethyl, trideuteriomethyl, aminomethyl and cyanomethyl, $R_4$ is —$C_{0-2}$—$C(O)R_{11}$ or —$C_{0-2}$—$C(O)NR_{12}R_{13}$, above groups are further optionally substituted by one or more substituents selected from the group consisting of deuterium, halogen, $C_{1-4}$ alkyl, $C_{3-6}$ cycloalkyl, 3-6 membered heterocyclyl, =O, —$C_{0-2}$—O—$R_{10}$ and —$C_{0-2}$—$NR_{12}R_{13}$, or, $R_3$ and $R_4$, together with the nitrogen atom directly attached thereto, form a 5-8 membered heterocyclyl, above groups are further optionally substituted by one or more substituents selected from the group consisting of deuterium, halogen, $C_{1-4}$ alkyl, $C_{3-6}$ cycloalkyl, 3-6 membered heterocyclyl, =O, —$C_{0-2}$—O—$R_{10}$ and —$C_{0-2}$—$NR_{12}R_{13}$.

In a further preferred embodiment, in the compound of formula (I), the stereoisomer or pharmaceutically acceptable salt thereof, $R_3$ is selected from the group consisting of hydrogen, deuterium, methyl, hydroxymethyl, methoxymethyl, methoxyethyl, cyclopropyl, cyclopropylmethyl, trifluoromethyl and trideuteriomethyl, $R_4$ is selected from the group consisting of —C(O)$R_{11}$ and —C(O)$NR_{12}R_{13}$, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino, or, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino.

In a preferred embodiment, in the compound of formula (I), the stereoisomer or pharmaceutically acceptable salt thereof, X is —N($R_5$)— or —C($R_6R_7$)—;

$R_5$ is selected from the group consisting of hydrogen, deuterium, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are further optionally substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, —$C_{0-4}$—S(O)$_r$$R_9$, —$C_{0-4}$—O—$R_{10}$ and —$C_{0-4}$—$NR_{12}R_{13}$;

$R_6$ and $R_7$ are each independently selected from the group consisting of hydrogen, deuterium, halogen, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)$_r$$R_9$, —$C_{0-4}$—O—$R_{10}$ and —$C_{0-4}$—$NR_{12}R_{13}$, or, $R_6$ and $R_7$, together with the nitrogen atom directly attached thereto, form a C(O), $C_{3-8}$ cycloalkyl or 3-8 membered heterocyclyl, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)$_r$$R_9$, —$C_{0-4}$—O—$R_{10}$, —$C_{0-8}$—C(O)O$R_{10}$, —$C_{0-4}$—C(O)$R_{11}$, —$C_{0-4}$—O—C(O)$R_{11}$, —$C_{0-4}$—$NR_{12}R_{13}$, —$C_{0-4}$—C(O)$NR_{12}R_{13}$, —$C_{0-4}$—N($R_{12}$)—C(O)$R_{11}$ and —$C_{0-4}$—N($R_{12}$)—C(O)O$R_{10}$.

In a further preferred embodiment, in the compound of formula (I), the stereoisomer or pharmaceutically acceptable salt thereof, X is —N($R_5$)— or —C($R_6R_7$)—;

$R_5$ is selected from the group consisting of deuterium, $C_{1-4}$ alkyl, $C_{3-8}$ cycloalkyl and 3-8 membered heterocyclyl, above groups are further optionally substituted by one or more substituents selected from the group consisting of deuterium, halogen, cyano, $C_{1-4}$ alkyl, $C_{3-6}$ cycloalkyl, 3-6 membered heterocyclyl, —S—$R_9$ and —O—$R_{10}$;

$R_6$ and $R_7$ are each independently selected from the group consisting of hydrogen, deuterium, halogen, $C_{1-4}$ alkyl, $C_{3-8}$ cycloalkyl, 3-8 membered heterocyclyl, —S—$R_9$ and —O—$R_{10}$, or, $R_6$ and $R_7$, together with the carbon atom directly attached thereto, form a C(O), $C_{3-6}$ cycloalkyl or 3-6 membered heterocyclyl, above groups are further more optionally substituted by one or more substituents selected from the group consisting of deuterium, halogen, cyano, $C_{1-4}$ alkyl, $C_{3-8}$ cycloalkyl 3-8 membered heterocyclyl, —S—$R_9$, —O—$R_{10}$ and —$NR_{12}R_{13}$.

In a preferred embodiment, the compound of formula (I), the stereoisomer or pharmaceutically acceptable salt thereof has the compound structure of the following formula (IIa):

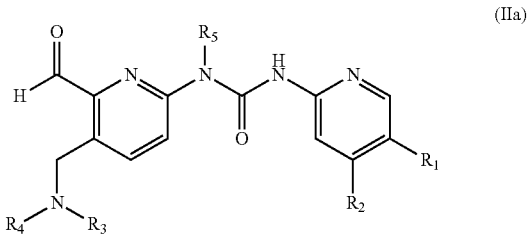

(IIa)

wherein, $R_1$ is selected rom the group consisting of deuterium, halogen, cyano, methyl, ethynyl, cyclopropyl cyclopentyl, oxa-cyclobutyl, aza-cyclohexyl, morpholinyl, $C_{5-6}$ aryl, 5-6 membered heteroaryl, methoxy, ethoxy, tert-butoxyl, amino, methylamino, dimethylamino, aminoacyl, dimethylaminoacyl, methylthio, sulfonyl and methylsulfonyl, above groups are further optionally substituted by one or more substituents selected from the group consisting of deuterium, fluorine, chlorine, methyl, isopropyl, tert-butyl, cyclopropyl, cyclopentyl, oxa-cyclobutyl, aza-cyclohexyl, morpholinyl, methoxy, ethoxy, tert-butoxyl, hydroxy, amino, methylamino and dimethylamino, above groups are further more optionally substituted by one or more substituents selected from the group consisting of deuterium, fluorine, chlorine, cyclopropyl, cyclopentyl, oxa-cyclobutyl, hydroxy, methoxy and amino;

$R_3$ is selected from the group consisting of hydrogen, deuterium, methyl, hydroxymethyl, methoxymethyl, methoxyethyl, cyclopropyl, cyclopropylmethyl, trifluoromethyl and trideuteriomethyl, $R_4$ is selected from the group consisting of —C(O)$R_{11}$ and —C(O)$NR_{12}R_{13}$, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino, or, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

R₅ is selected from the group consisting of deuterium, $C_{1-4}$ alkyl, $C_{3-8}$ cycloalkyl and 3-8 membered heterocyclyl, above groups are further optionally substituted by one or more substituents selected from the group consisting of deuterium, halogen, cyano, $C_{1-4}$ alkyl, $C_{3-6}$ cycloalkyl, 3-6 membered heterocyclyl, —S—$R_9$ and —O—$R_{10}$;

$R_2$, $R_9$, $R_{10}$, $R_{11}$, $R_{12}$, $R_{13}$ and r are defined as the compound of formula (I).

In a further preferred embodiment, in the compound of formula (I), the stereoisomer or pharmaceutically acceptable salt thereof, $R_1$ is selected from the group consisting of deuterium, halogen, ethynyl and cyclopropyl, said ethynyl or cyclopropyl is optionally further substituted by one or more substituents selected from the group consisting of deuterium, fluorine, chlorine, methyl, isopropyl, tert-butyl, cyclopropyl, cyclopentyl, oxa-cyclobutyl, aza-cyclohexyl, morpholinyl, methoxy, ethoxy, tert-butoxyl, hydroxy, amino, methylamino and dimethylamino, above groups are further more optionally substituted by one or more substituents selected from the group consisting of deuterium, fluorine, chlorine, cyclopropyl, cyclopentyl, oxa-cyclobutyl, hydroxy, methoxy and amino;

$R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

$R_5$ is selected from the group consisting of deuterium, $C_{1-4}$ alkyl, $C_{3-8}$ cycloalkyl and 3-8 membered heterocyclyl, above groups are further optionally substituted by one or more substituents selected from the group consisting of deuterium, halogen, cyano, $C_{1-4}$ alkyl, $C_{3-6}$ cycloalkyl, 3-6 membered heterocyclyl, —S—$R_9$ and —O—$R_{10}$.

In the most preferred embodiment, the compound of formula (I), the stereoisomer or pharmaceutically acceptable salt thereof includes, but is not limited to, the following compounds:

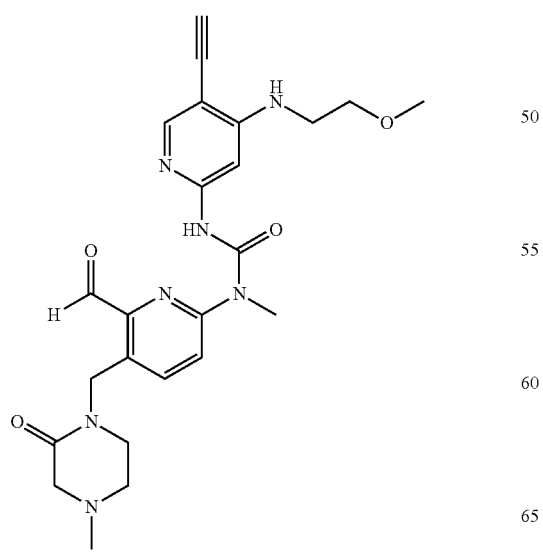

-continued

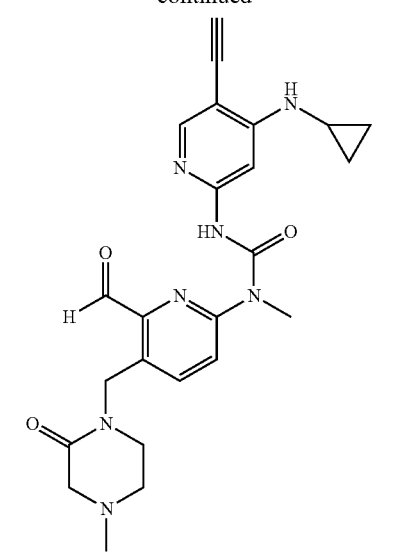

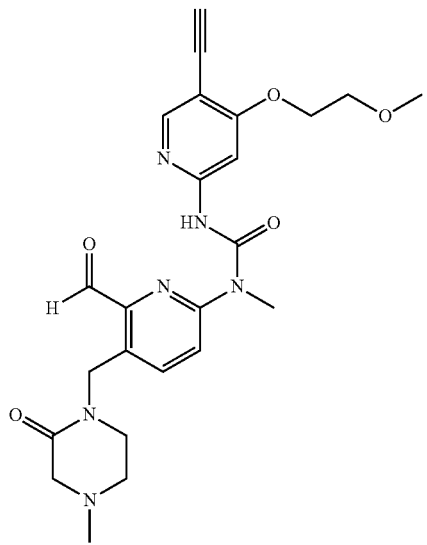

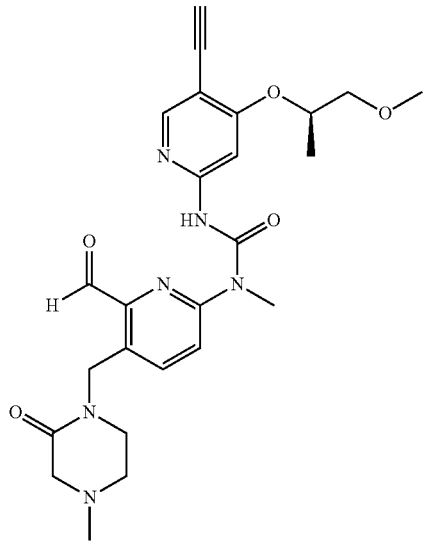

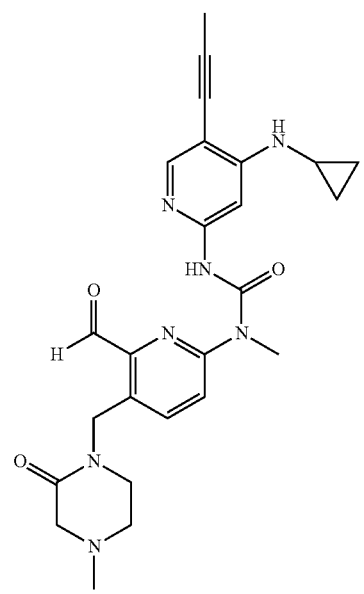
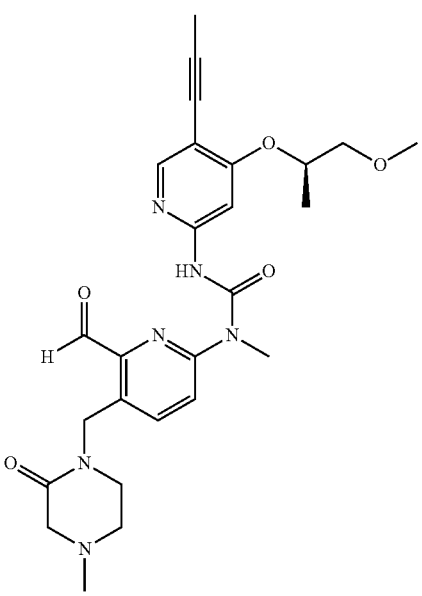
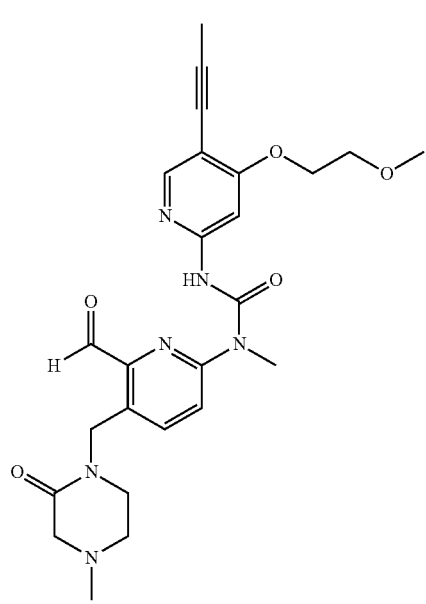
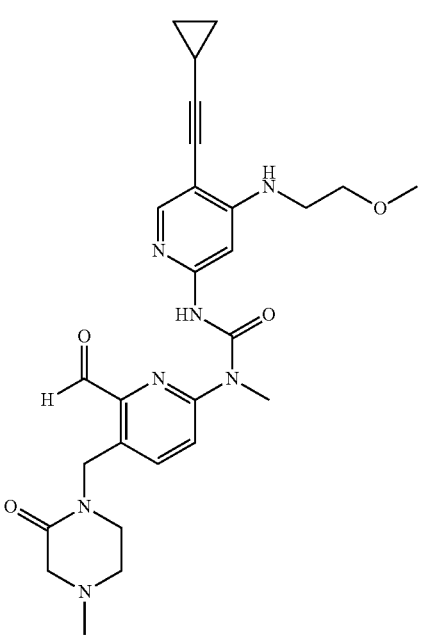

13
-continued
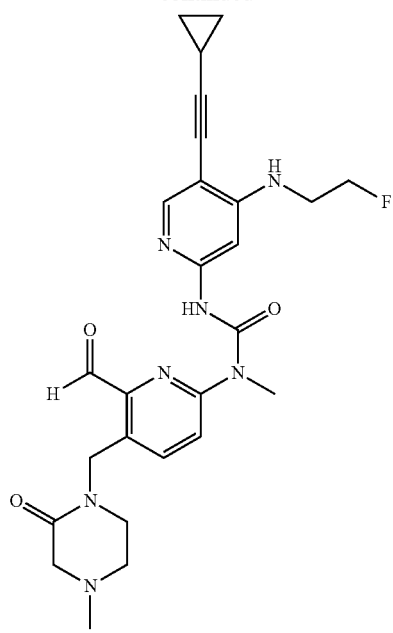
14
-continued
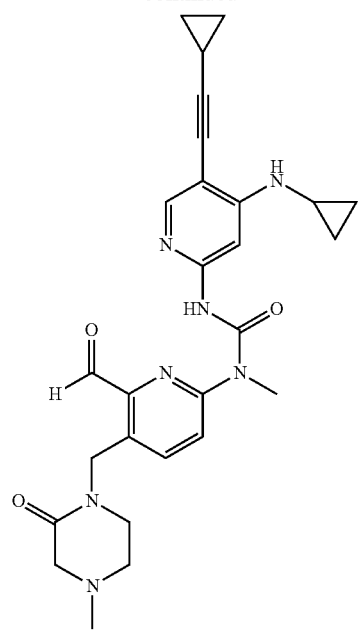

15
-continued
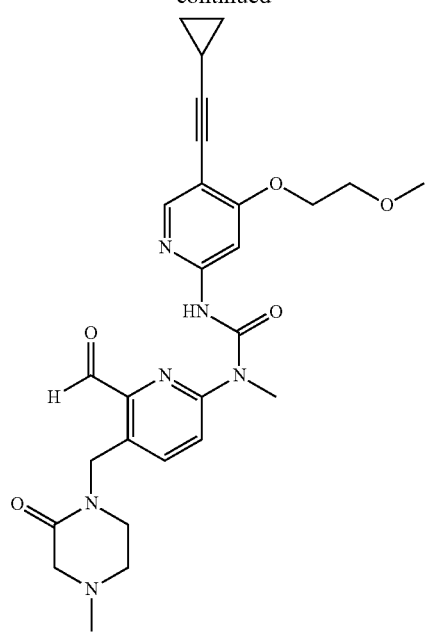
16
-continued
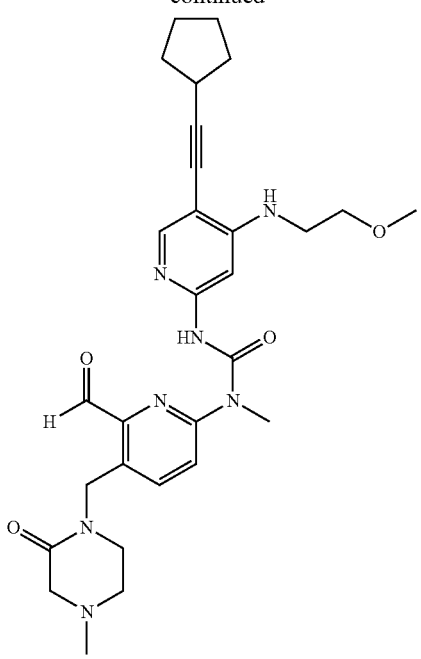
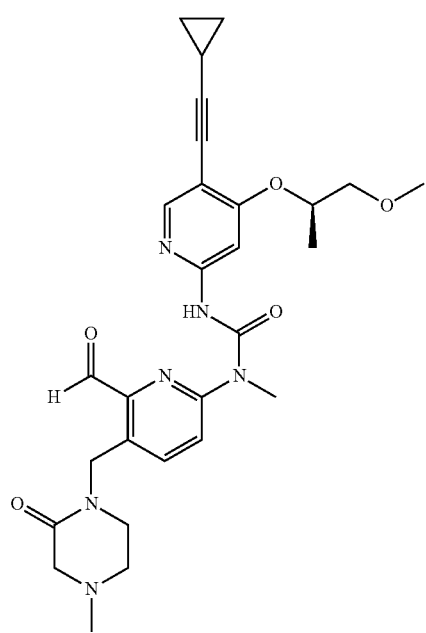
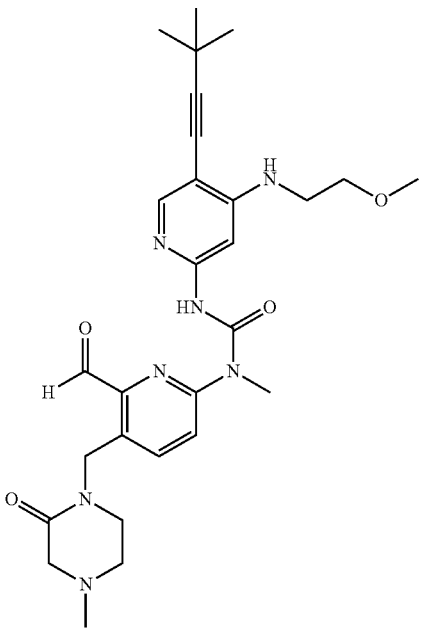

17
-continued

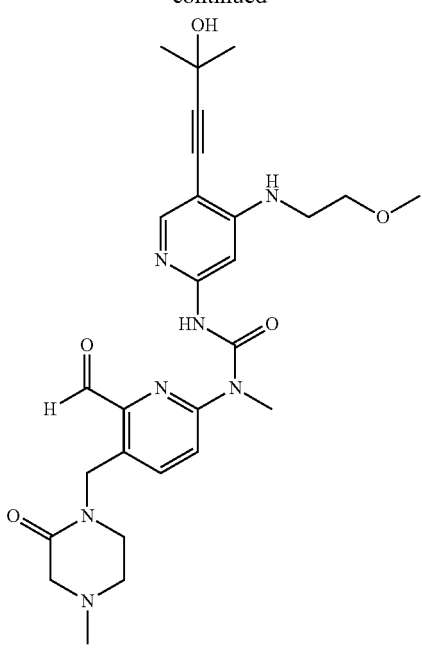

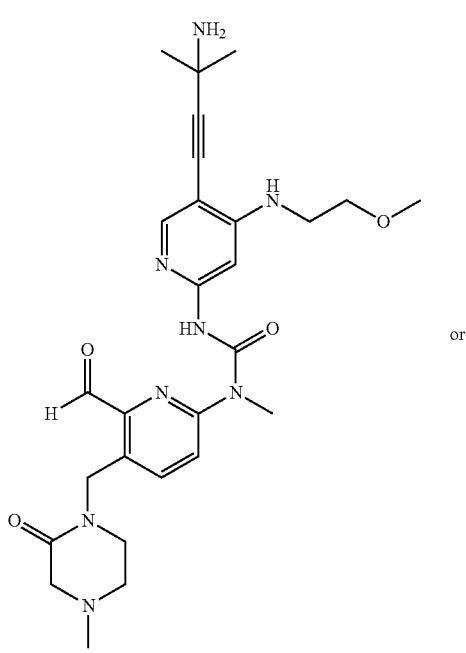

or

18
-continued

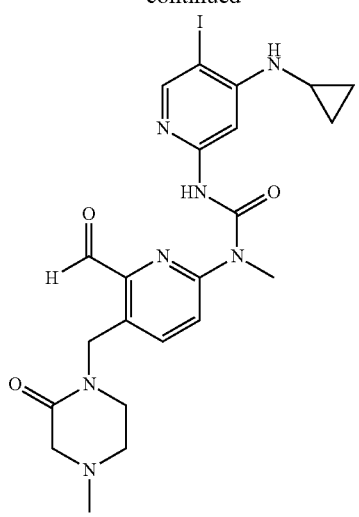

In a further preferred embodiment, in the compound of formula (I), the stereoisomer or pharmaceutically acceptable salt thereof, $R_1$ is cyano;

$R_2$ is —S—$R_9$, —O—$R_{10}$ or —$NR_{12}R_{13}$, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_9$, —$C_{0-8}$—O—$R_{10}$, —$C_{0-8}$—C(O)$R_{10}$, —$C_{0-8}$—C(O)$R_{11}$, —$C_{0-8}$—O—C(O)$R_{11}$, —$C_{0-8}$—$NR_{12}R_{13}$, —$C_{0-8}$—C(O)$NR_{12}R_{13}$, —$C_{0-8}$—N($R_{12}$)—C(O)$R_{11}$ and —$C_{0-8}$—N($R_{12}$)—C(O)$OR_{10}$, above groups are further more optionally substituted by one or more substituents selected from the group consisting of deuterium, halogen, cyano, nitro, azido $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_9$, —$C_{0-8}$—O—$R_{10}$, —$C_{0-8}$—C(O)$OR_{10}$, —$C_{0-8}$—C(O)$R_{11}$, —$C_{0-8}$—O—C(O)$R_{11}$, —$C_{0-8}$—$NR_{12}R_{13}$, —$C_{0-8}$—C(O)$NR_{12}R_{13}$, —$C_{0-8}$—N($R_{12}$)—C(O)$R_{11}$ and —$C_{0-8}$—N($R_{12}$)—C(O)$OR_{10}$;

$R_3$ is selected from the group consisting of hydrogen, deuterium, methyl, hydroxymethyl, methoxymethyl, methoxyethyl, cyclopropyl, cyclopropylmethyl, trifluoromethyl and trideuteriomethyl, $R_4$ is —C(O)Ru or —C(O)$NR_{12}R_{13}$, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino, or, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

$R_5$ is selected from the group consisting of deuterium, $C_{1-4}$ alkyl, $C_{3-8}$ cycloalkyl and 3-8 membered heterocyclyl, above groups are further optionally substituted by one or more substituents selected from the group consisting of deuterium, halogen, cyano, $C_{1-4}$ alkyl, $C_{3-6}$ cycloalkyl, 3-6 membered heterocyclyl, —S—$R_9$ and —O—$R_{10}$.

In a further preferred embodiment, the compound of formula (I), the stereoisomer or pharmaceutically acceptable salt thereof has the compound structure of the following formula (III a-1):

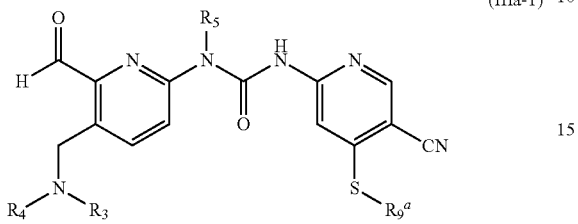

(IIIa-1)

wherein,

R$_3$ is selected from the group consisting of hydrogen, deuterium, methyl, hydroxymethyl, methoxymethyl, methoxyethyl, cyclopropyl, cyclopropylmethyl, trifluoromethyl and trideuteriomethyl, R$_4$ is —C(O)Ru or —C(O)NR$_{12}$R$_{13}$, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino, or, R$_3$ and R$_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

R$_5$ is selected from the group consisting of deuterium, C$_{1-4}$ alkyl, C$_{3-8}$ cycloalkyl and 3-8 membered heterocyclyl, above groups are further optionally substituted by one or more substituents selected from the group consisting of deuterium, halogen, cyano, C$_{1-4}$ alkyl, C$_{3-6}$ cycloalkyl, 3-6 membered heterocyclyl, —S—R$_9$ and —O—R$_{10}$;

R$_9^a$ is selected from the group consisting of hydrogen, deuterium, C$_{1-4}$ alkyl, C$_{2-8}$ alkenyl, C$_{3-10}$ cycloalkyl, 3-10 membered heterocyclyl, C$_{5-10}$ aryl and 5-10 membered heteroaryl, above groups are further optionally substituted by one or more substituents selected from the group consisting of deuterium, halogen, hydroxy, carbonyl, C$_{1-4}$ alkyl, C$_{1-4}$ alkoxy, C$_{3-8}$ cycloalkyl, C$_{3-8}$ cycloalkyloxy, 3-8 membered heterocyclyl, 3-8 membered heterocyclyloxy, C$_{5-8}$ aryl, C$_{5-8}$ aryloxy, 5-8 membered heteroaryl, 5-8 membered heteroaryloxy and —NR$_{12}$R$_{13}$;

R$_9$, R$_{10}$, R$_{11}$, R$_{12}$, R$_{13}$ and r are defined as the compound of formula (I).

In the most preferred embodiment, the compound of formula (I), the stereoisomer or pharmaceutically acceptable salt thereof includes, but is not limited to, the following compounds:

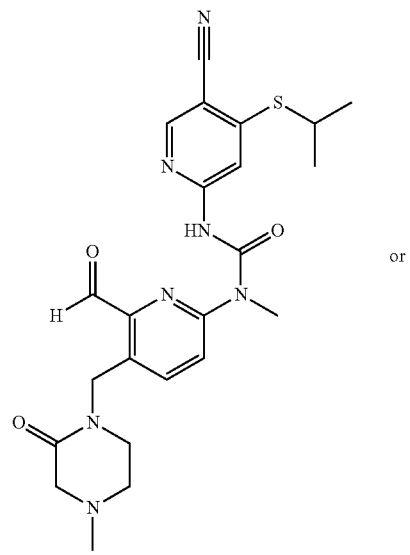

or

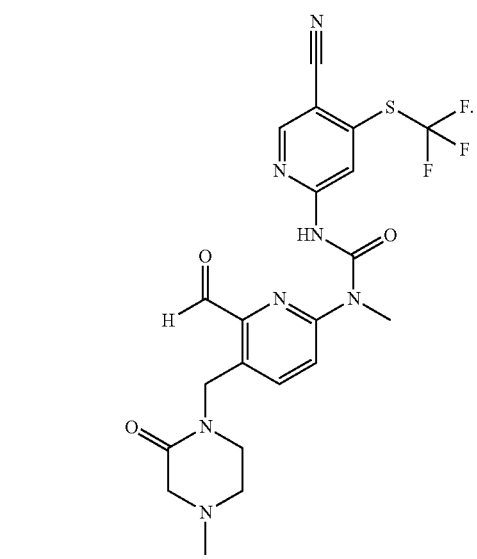

In a further preferred embodiment, the compound of formula (I), the stereoisomer or pharmaceutically acceptable salt thereof has the compound structure of the following formula (III a-2):

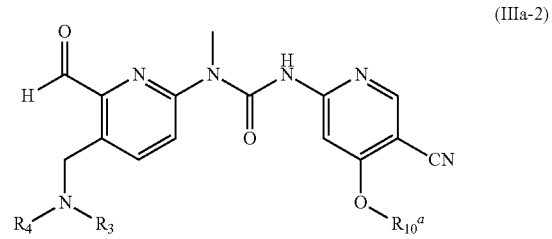

(IIIa-2)

wherein, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

$R_{10}{}^a$ is selected from (i) $C_{1-4}$ alkyl, said $C_{1-4}$ alkyl is further substituted by one or more substituents selected from the group consisting of deuterium, halogen, hydroxy, carbonyl, cyano, $C_{1-4}$ alkyl $C_{1-4}$ alkoxy, $C_{3-8}$ cycloalkyl, $C_{3-8}$ cycloalkyloxy, 3-8 membered heterocyclyl and 3-8 membered heterocyclyloxy, said $C_{3-8}$ cycloalkyl, or 3-8 membered heterocyclyl is optionally further more substituted by one or more substituents selected from the group consisting of deuterium, halogen, $C_{3-8}$ cycloalkyl, 3-8 membered heterocyclyl, hydroxy and $C_{1-4}$ alkoxy; or (ii) $C_{3-8}$ cycloalkyl or 3-8 membered heterocyclyl, above groups are further optionally substituted by one or more substituents selected from the group consisting of deuterium, halogen, hydroxy, carbonyl, cyano, $C_{1-4}$ alkyl, $C_{1-4}$ alkoxy, $C_{1-4}$ alkoxy $C_{1-4}$ alkyl, $C_{3-8}$ cycloalkyl, $C_{3-8}$ cycloalkyloxy, 3-8 membered heterocyclyl, and 3-8 membered heterocyclyloxy, the said $C_{3-8}$ cycloalkyl, or 3-8 membered heterocyclyl is optionally further more substituted by one or more substituents selected from the group consisting of deuterium, halogen, $C_{3-8}$ cycloalkyl, 3-8 membered heterocyclyl, hydroxy and $C_{1-4}$ alkoxy.

In the most preferred embodiment, the compound of formula (I), the stereoisomer or pharmaceutically acceptable salt thereof includes, but is not limited to, the following compounds:

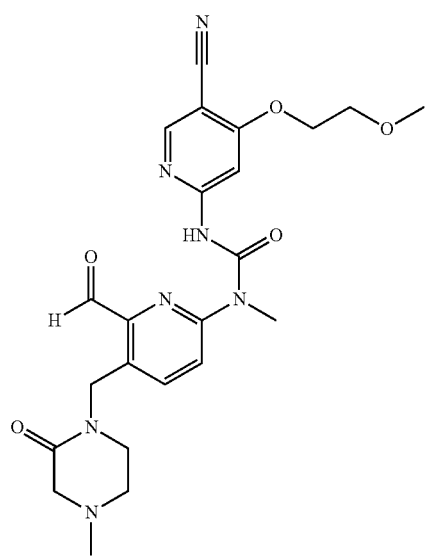

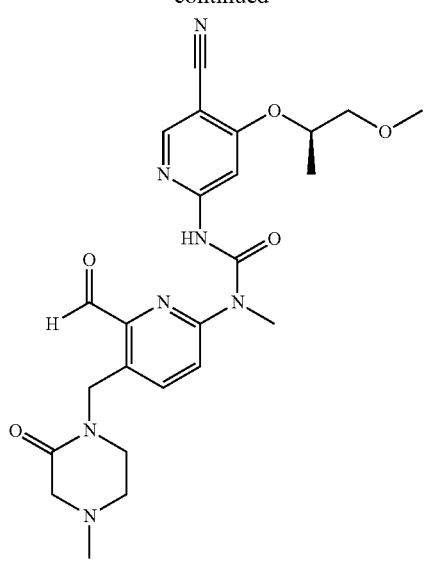

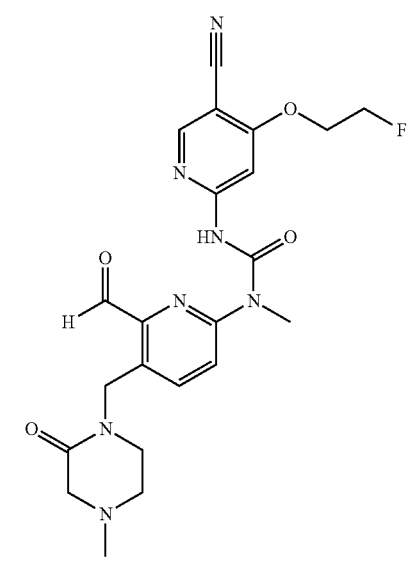

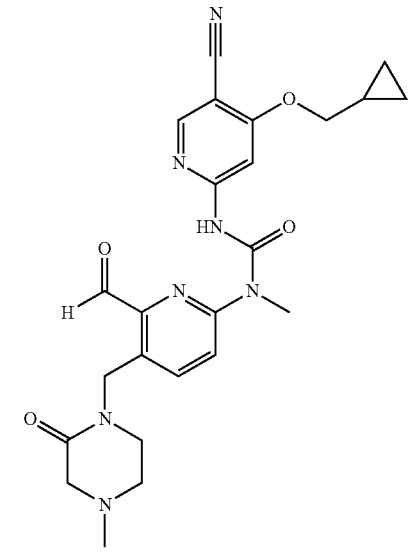

-continued
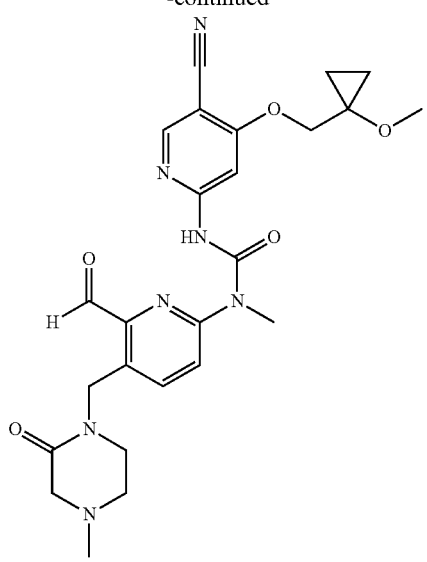
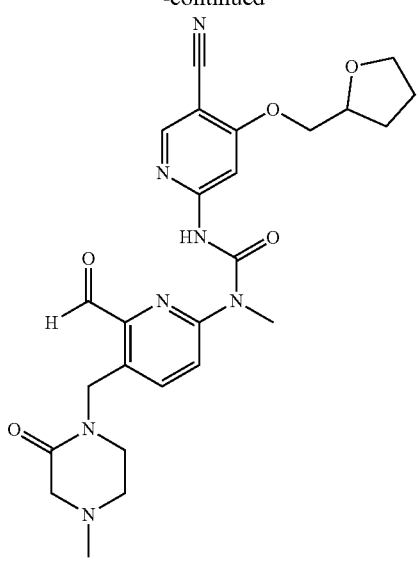

-continued

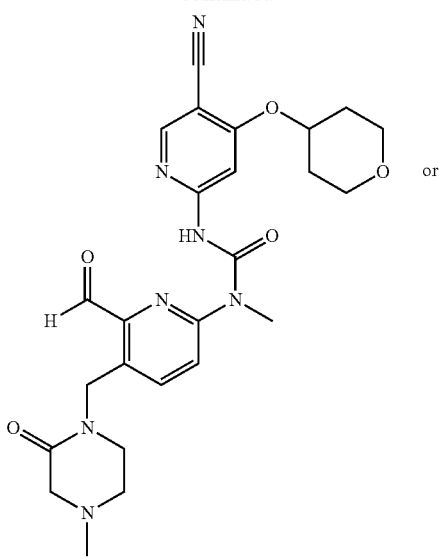

or

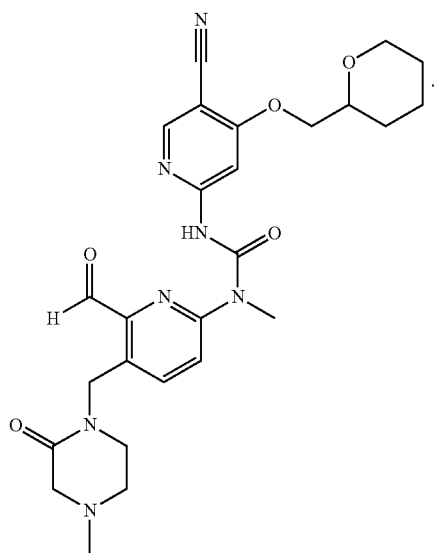

In a further preferred embodiment, the compound of formula (I), the stereoisomer or pharmaceutically acceptable salt thereof has the compound structure of the following formula (III a-3):

(IIIa-3)

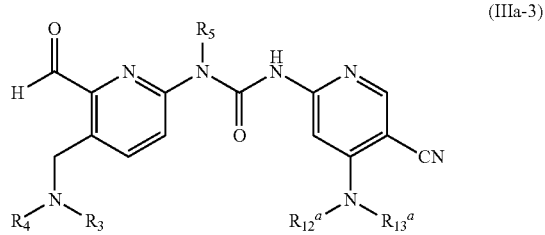

wherein, $R_3$ is selected from the group consisting of hydrogen, deuterium, methyl, hydroxymethyl, methoxymethyl, methoxyethyl, cyclopropyl, cyclopropylmethyl, trifluoromethyl and trideuteriomethyl, $R_4$ is —C(O)$R_{11}$ or —C(O)N$R_{12}R_{13}$, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino, or, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

$R_5$ is selected from the group consisting of deuterium, $C_{1-4}$ alkyl, $C_{3-8}$ cycloalkyl and 3-8 membered heterocyclyl, above groups are further optionally substituted by one or more substituents selected from the group consisting of deuterium, halogen, cyano, $C_{1-4}$ alkyl, $C_{3-6}$ cycloalkyl, 3-6 membered heterocyclyl and $C_{1-4}$ alkoxy;

$R_{12}^a$ is hydrogen or deuterium, $R_{13}^a$ is selected from (i) $C_{1-8}$ alkyl, said $C_{1-8}$ alkyl is further substituted by one or more substituents selected from the group consisting of deuterium, halogen, $C_{3-8}$ cycloalkyl, $C_{3-8}$ cycloalkyloxy, 3-8 membered heterocyclyl, and 3-8 membered heterocyclyloxy, said $C_{3-8}$ cycloalkyl, or 3-8 membered heterocyclyl is optionally further more substituted by one or more substituents selected from the group consisting of deuterium, halogen, $C_{3-8}$ cycloalkyl, 3-8 membered heterocyclyl, hydroxy and $C_{1-4}$ alkoxy; or, (ii) $C_{3-10}$ cycloalkyl or 3-10 membered heterocyclyl, said $C_{3-10}$ cycloalkyl or 3-10 membered heterocyclyl is optionally further substituted by one or more substituents selected from the group consisting of deuterium, halogen, hydroxy, $C_{1-4}$ alkyl, $C_{1-4}$ alkoxy, $C_{3-8}$ cycloalkyl, $C_{3-8}$ cycloalkyloxy, 3-8 membered heterocyclyl, and 3-8 membered heterocyclyloxy, said $C_{1-4}$ alkyl, $C_{3-8}$ cycloalkyl, or 3-8 membered heterocyclyl is optionally further substituted by one or more substituents selected from the group consisting of deuterium, halogen, $C_{3-8}$ cycloalkyl, 3-8 membered heterocyclyl, hydroxy and $C_{1-4}$ alkoxy, or, $R_{12}^a$ and $R_{13}^a$, together with the nitrogen atom directly attached thereto, form a 4-10 membered heterocyclyl, above groups are further optionally substituted by one or more substituents selected from the group consisting of deuterium, halogen, hydroxy, $C_{1-4}$ alkyl, $C_{1-4}$ alkoxy, $C_{3-8}$ cycloalkyl, $C_{3-8}$ cycloalkyloxy, 3-8 membered heterocyclyl, and 3-8 membered heterocyclyloxy.

In the most preferred embodiment, the compound of formula (I), the stereoisomer or pharmaceutically acceptable salt thereof includes, but is not limited to, the following compounds:
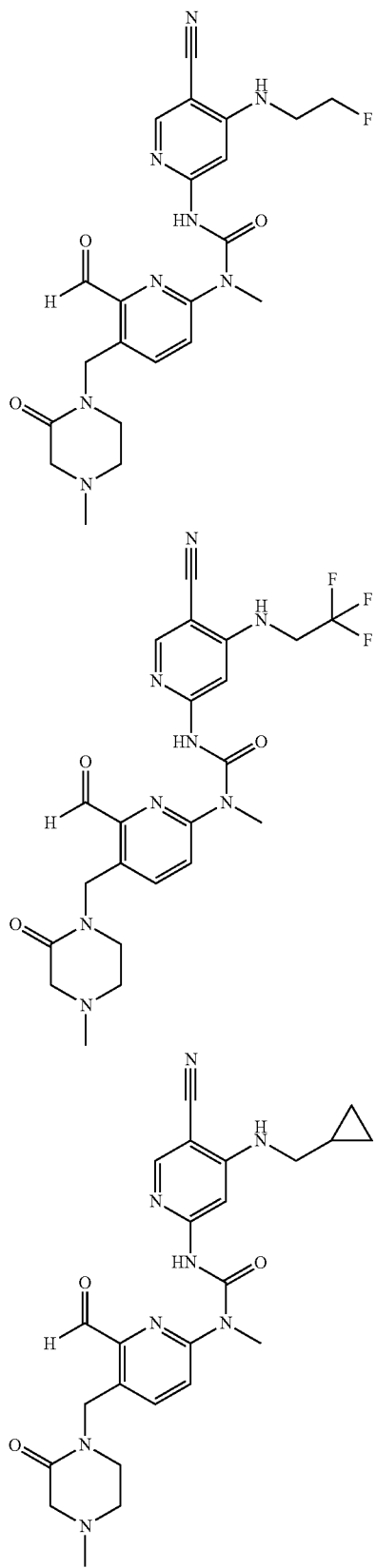
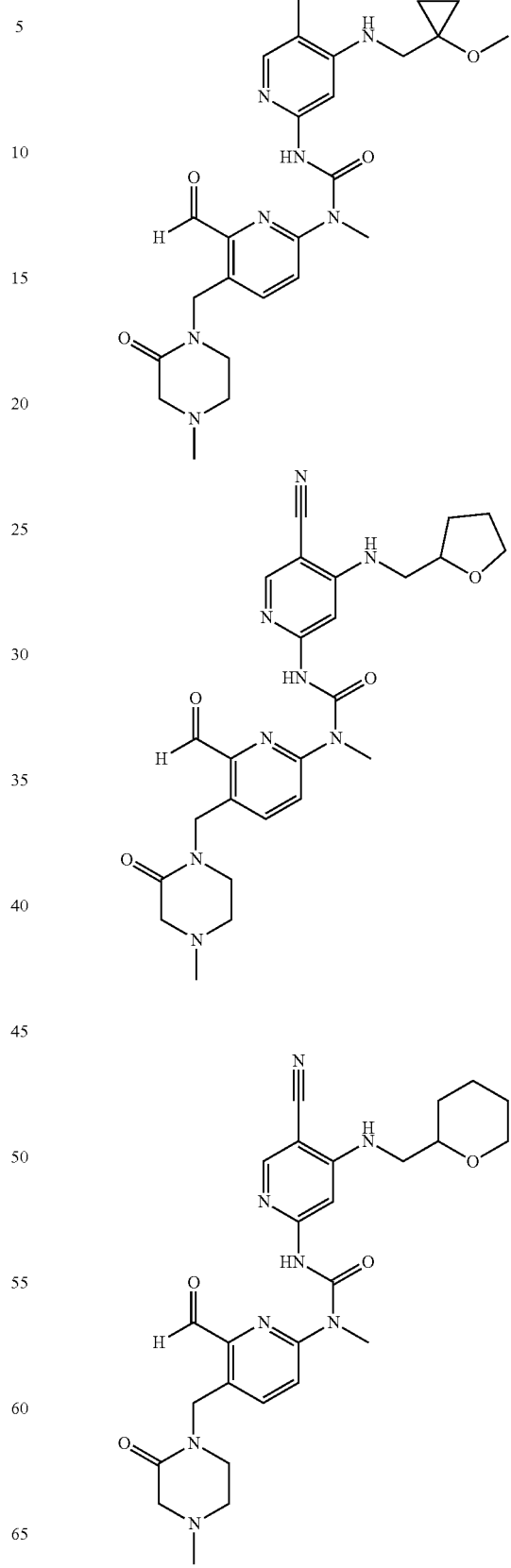

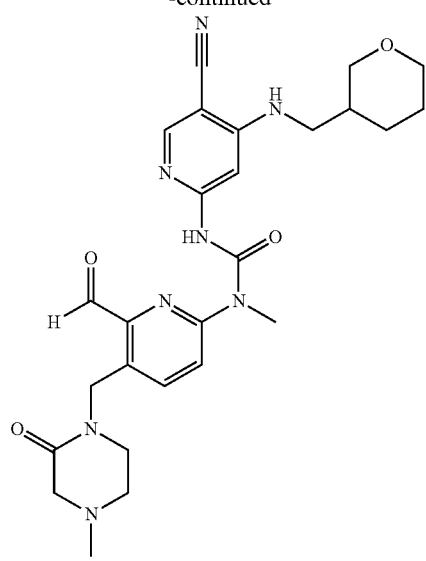
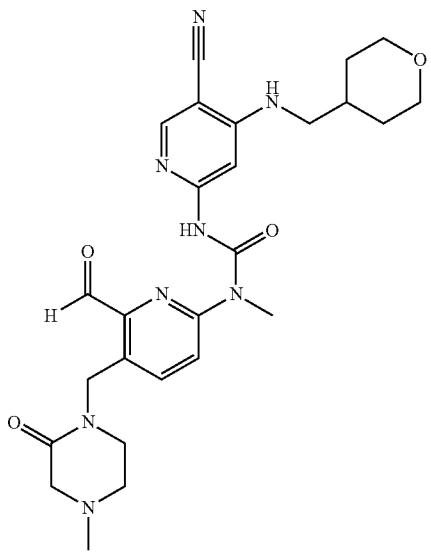
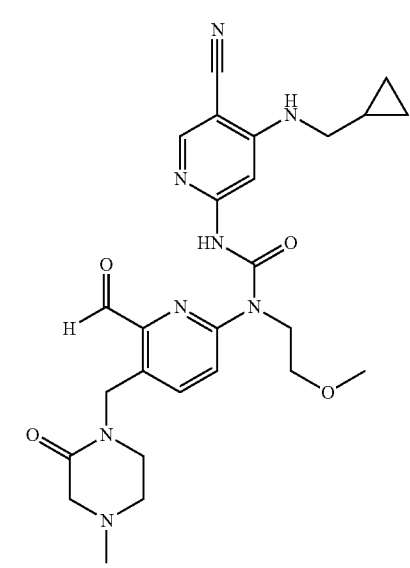
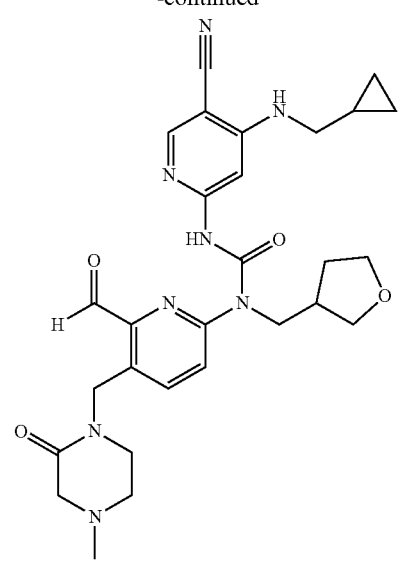
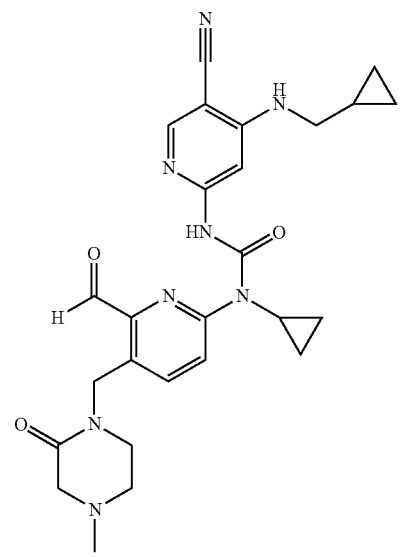
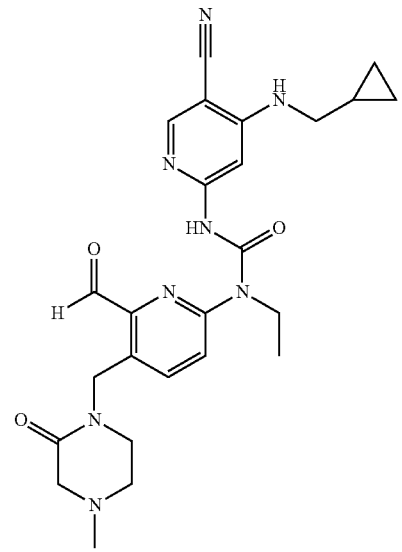

-continued
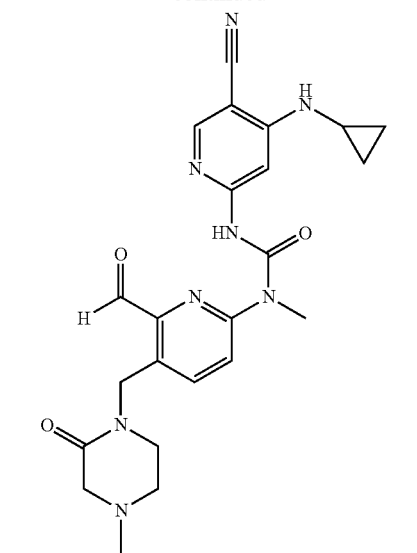
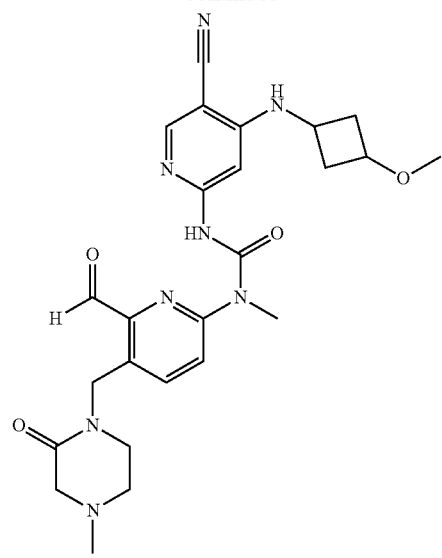
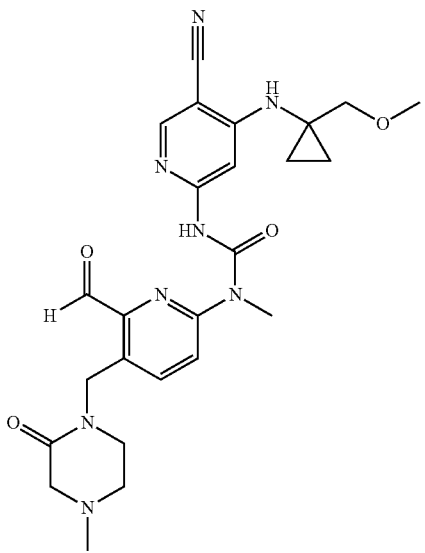
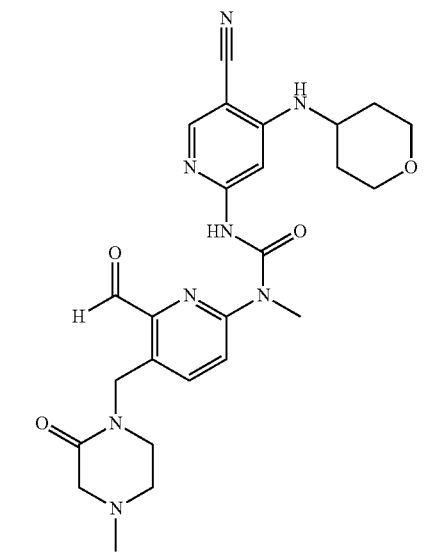
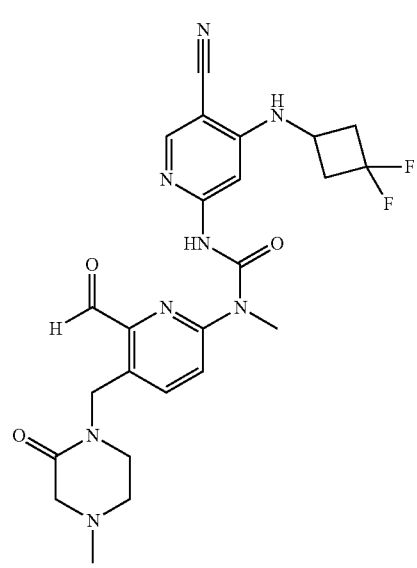
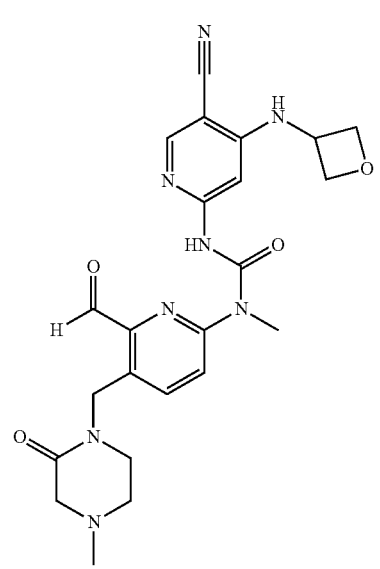

33
-continued
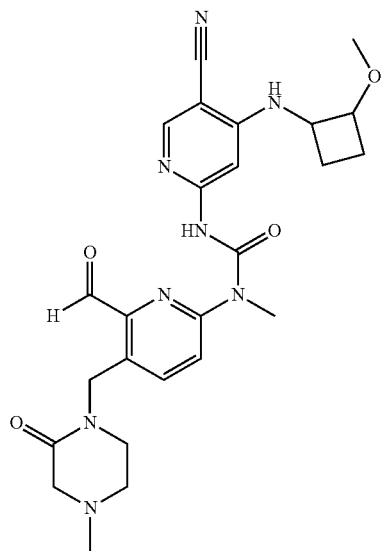
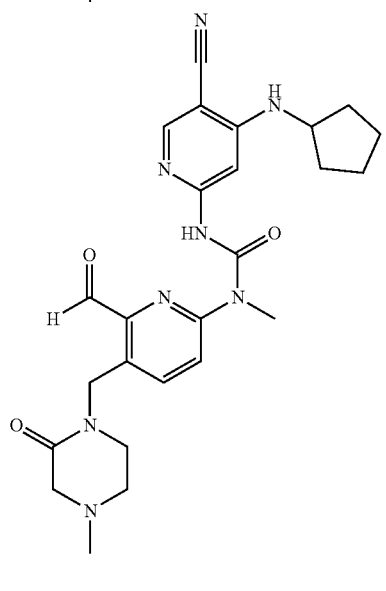
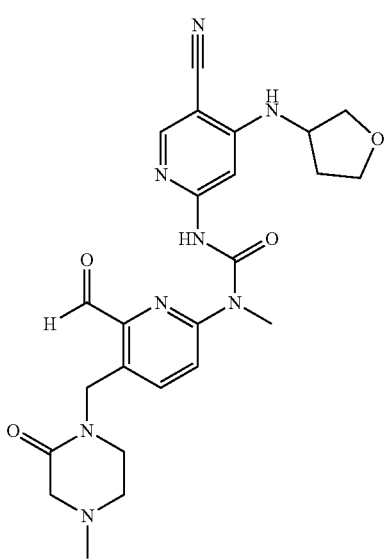
34
-continued
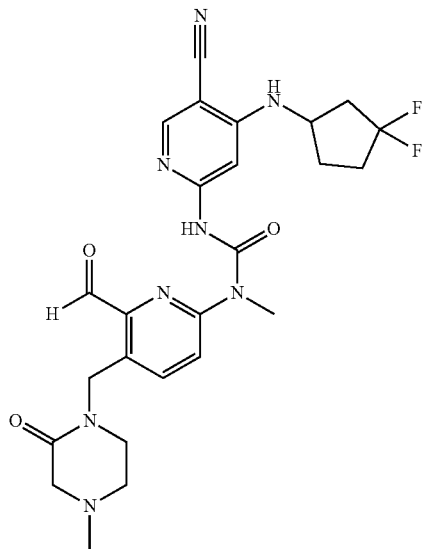
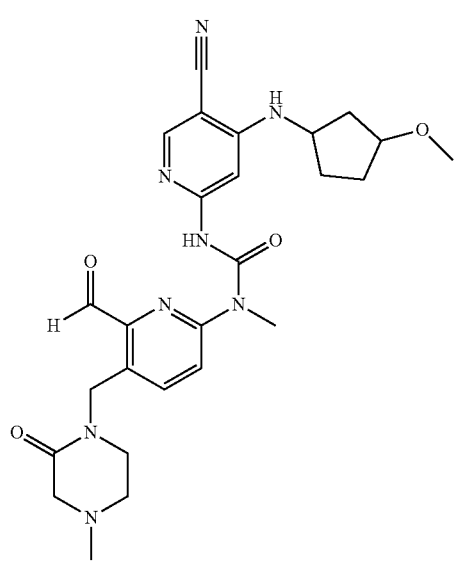
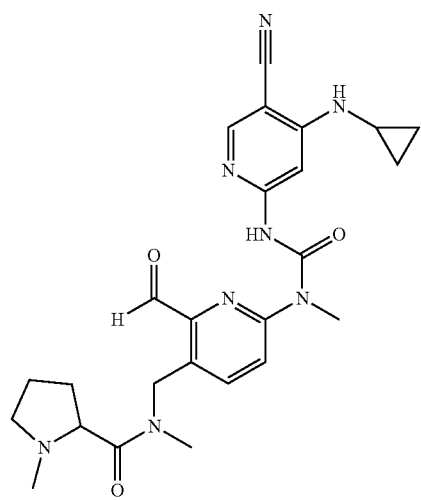

35
-continued
36
-continued
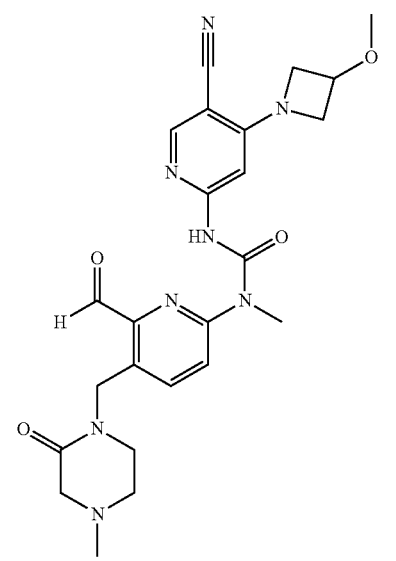
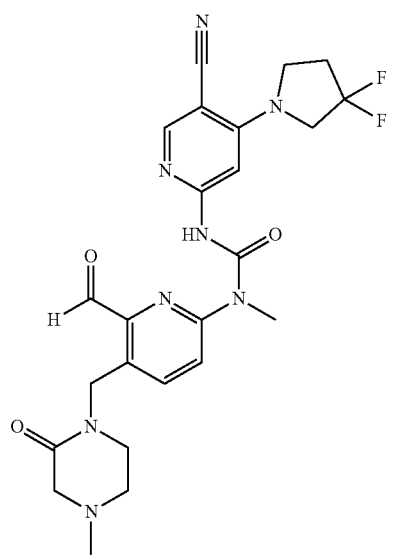

37
-continued
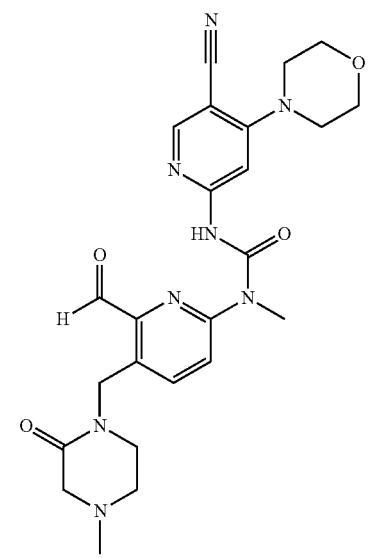
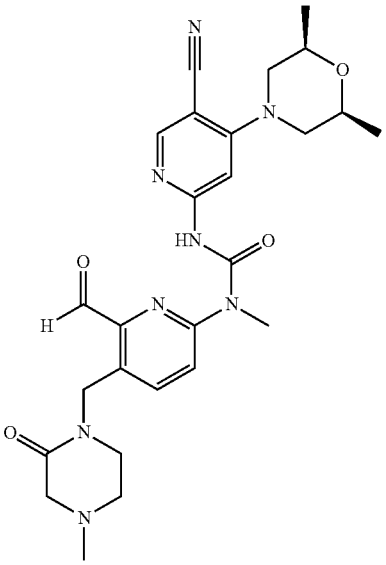
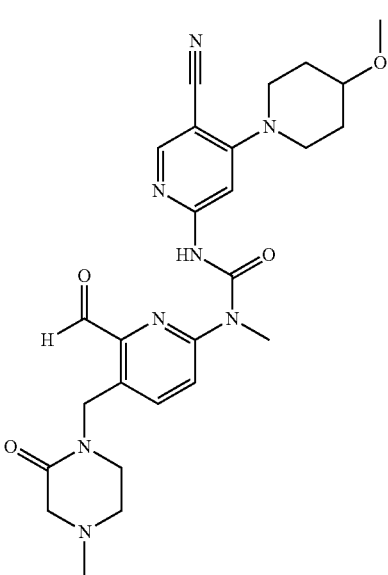
38
-continued
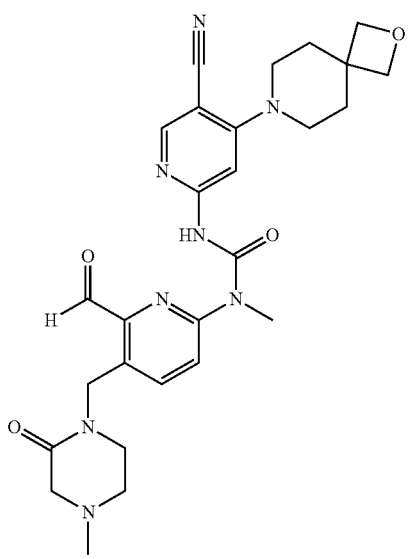
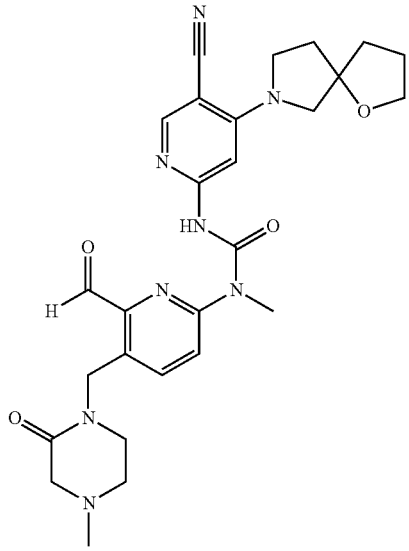
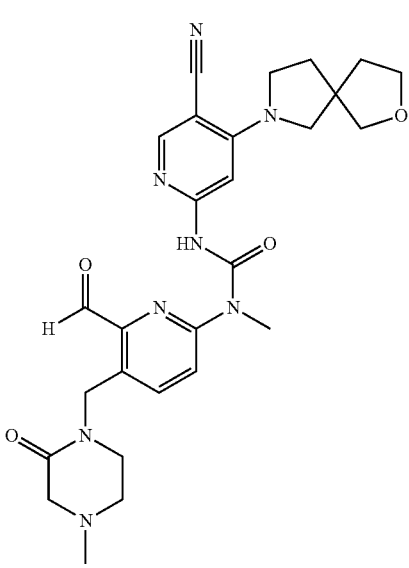

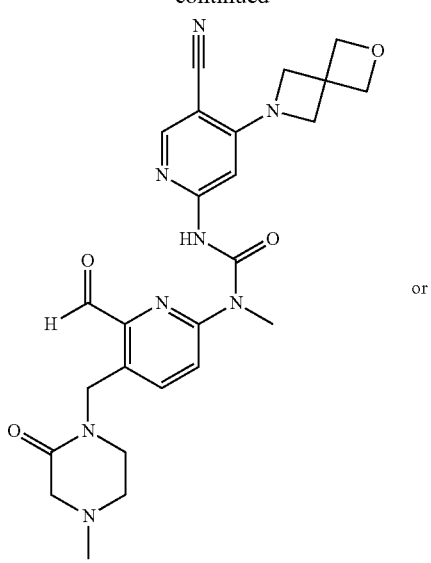

or

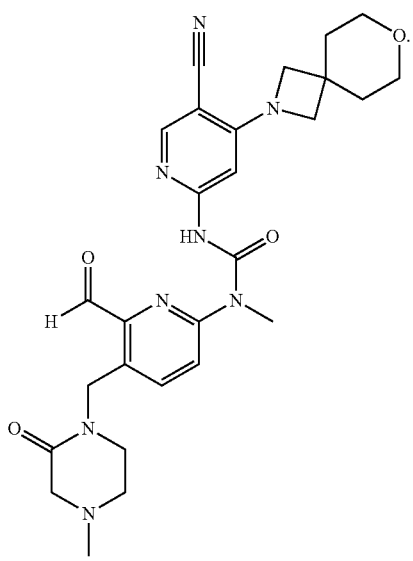

In a further preferred embodiment, the compound of the formula (I), the stereoisomer or pharmaceutically acceptable salt thereof, the compound has the compound structure of the following formula (IIb):

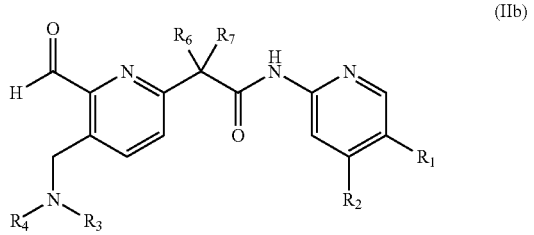

(IIb)

wherein, $R_1$ is selected from the group consisting of deuterium, halogen, cyano, methyl, ethynyl, cyclopropyl, cyclopentyl, oxa-cyclobutyl, aza-cyclohexyl, morpholinyl, $C_{5-6}$ aryl, 5-6 membered heteroaryl, methoxy, ethoxy, tert-butoxyl, amino, methylamino, dimethylamino, aminoacyl, dimethylaminoacyl, methylthio, sulfonyl and methylsulfonyl, above groups are further optionally substituted by one or more substituents selected from the group consisting of deuterium, fluorine, chlorine, methyl, isopropyl, tert-butyl, cyclopropyl, cyclopentyl, oxa-cyclobutyl, aza-cyclohexyl, morpholinyl, methoxy, ethoxy, tert-butoxyl, hydroxy, amino, methylamino and dimethylamino, above groups are further more optionally substituted by one or more substituents selected from the group consisting of deuterium, fluorine, chlorine, cyclopropyl, cyclopentyl, oxa-cyclobutyl, hydroxy, methoxy and amino;

$R_6$ and $R_7$ are each independently selected from the group consisting of hydrogen, deuterium, halogen, $C_{1-4}$ alkyl, $C_{3-8}$ cycloalkyl, 3-8 membered heterocyclyl, —S—$R_9$ and —O—$R_{10}$, or, $R_6$ and $R_7$, together with the carbon atom directly attached thereto, form a C(O), $C_{3-6}$ cycloalkyl or 3-6 membered heterocyclyl, above groups are further more optionally substituted by one or more substituents selected from the group consisting of deuterium, halogen, cyano, $C_{1-4}$ alkyl, $C_{3-8}$ cycloalkyl, 3-8 membered heterocyclyl, —S—$R_9$, —O—$R_{10}$ and —$NR_{12}R_{13}$;

$R_2$, $R_3$, $R_4$, $R_5$, $R_9$, $R_{10}$, $R_{11}$, $R_{12}$, $R_{13}$ and r are defined as the compound of formula (I).

In a further preferred embodiment, in the compound of formula (I), the stereoisomer or pharmaceutically acceptable salt thereof, $R_1$ is cyano or ethynyl, said ethynyl is optionally further substituted by one or more substituents selected from the group consisting of deuterium, fluorine, chlorine, methyl, isopropyl, tert-butyl, cyclopropyl, cyclopentyl, oxa-cyclobutyl, aza-cyclohexyl, morpholinyl, methoxy, ethoxy, tert-butoxyl, hydroxy, trifluoromethyl, difluoromethyl, trideuteriomethyl, cyclopropylmethyl, methoxy, amino, methylamino and dimethylamino;

$R_3$ is selected from the group consisting of hydrogen, deuterium, methyl, hydroxymethyl, methoxymethyl, methoxyethyl, cyclopropyl, cyclopropylmethyl, trifluoromethyl and trideuteriomethyl, $R_4$ is —C(O)$R_{11}$ or —C(O)$NR_{12}R_{13}$, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino, or, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino.

In the most preferred embodiment, the compound of formula (I), the stereoisomer or pharmaceutically acceptable salt thereof includes, but is not limited to, the following compounds:
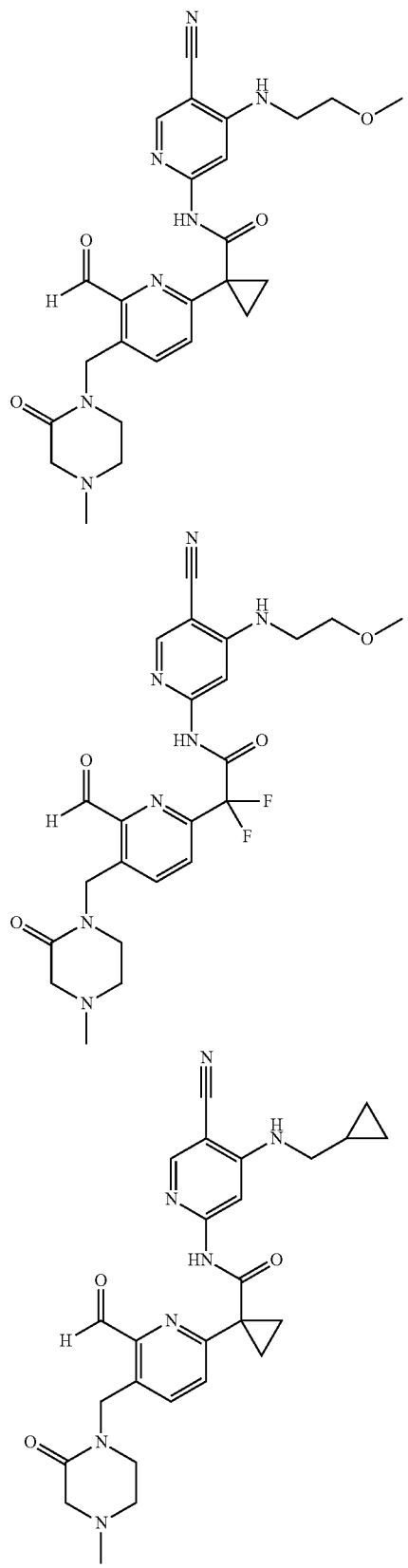
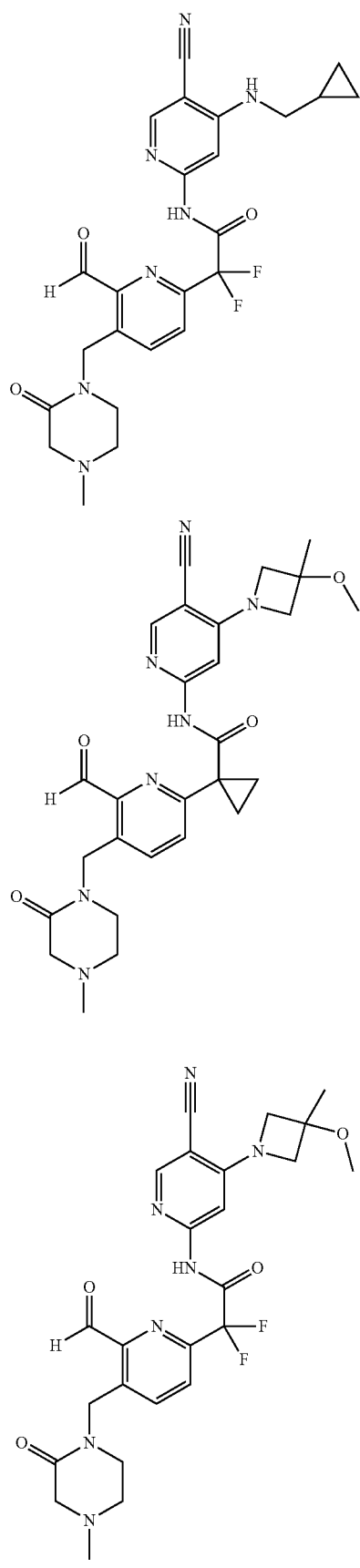

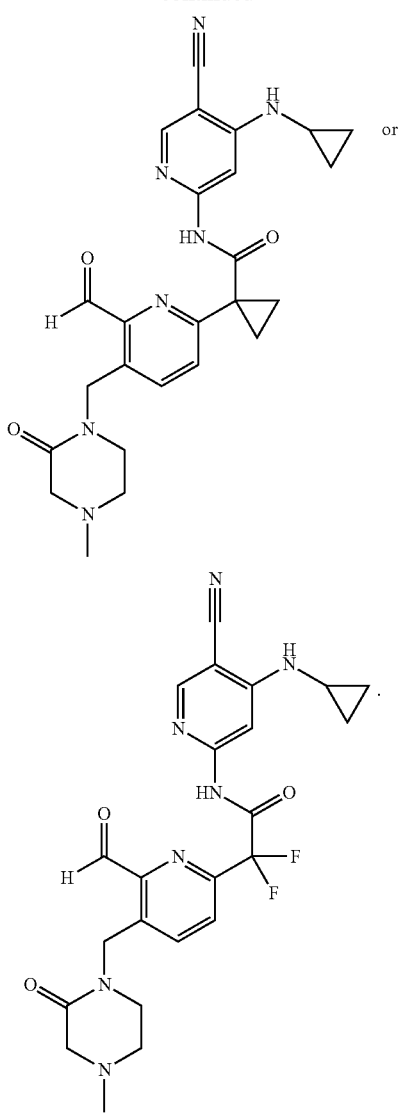

The second aspect of the invention provides a process for preparing the above compound of formula (I), the stereoisomer or pharmaceutically acceptable salt thereof, which comprises the following steps when X is —C(R₆R₇)— and Y is —C(O)—:

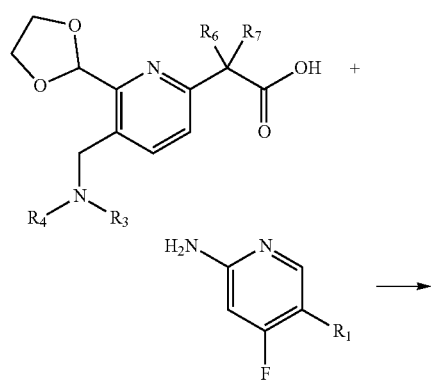

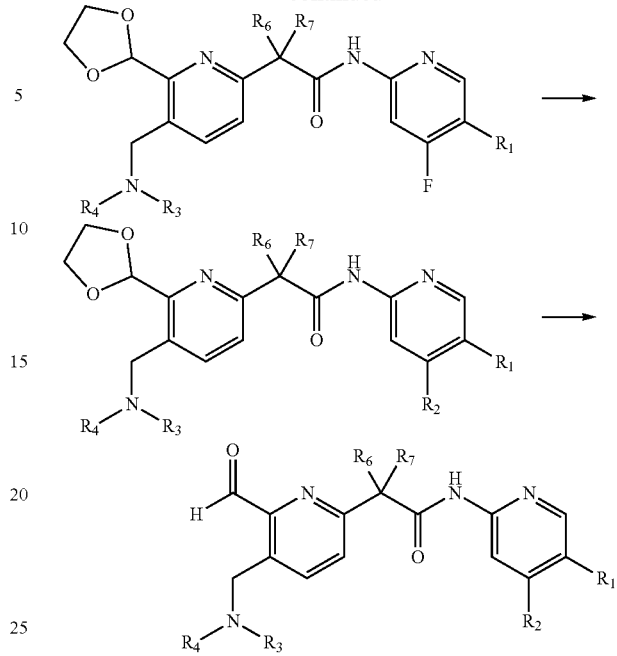

or, comprises the following steps when X is —N(R₅)— and Y is —C(O)—:

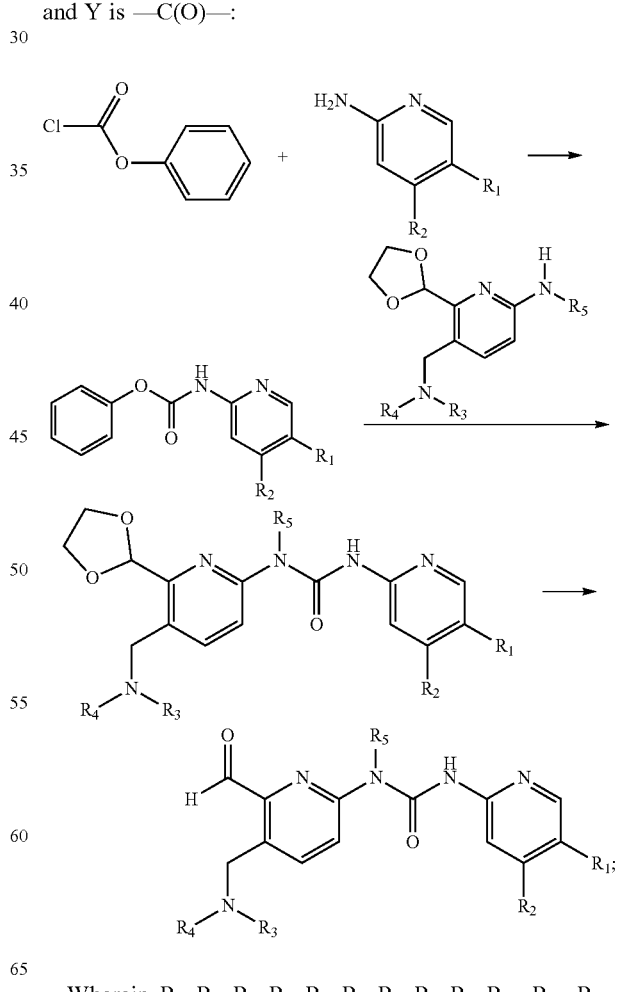

Wherein, R₁, R₂, R₃, R₄, R₅, R₆, R₇, R₈, R₉, R₁₀, R₁₁, R₁₂, R₁₃ and r are defined as the compound of formula (I).

The third aspect of the present invention provides a pharmaceutical composition comprising the above compound of formula (I), the stereoisomer or pharmaceutically acceptable salt thereof, and pharmaceutically acceptable carrier.

The fourth aspect of the present invention provides use of the above compound of formula (I), the stereoisomer or pharmaceutically acceptable salt thereof or the aforementioned pharmaceutical composition for preparing a medicament as an FGFR4 inhibitor.

The fifth aspect of the present invention provides uses of the above compound of formula (I), the stereoisomer or pharmaceutically acceptable salt thereof, or a pharmaceutical composition thereof, in the manufacturing of medicament for treating cancer; preferably, the said cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

The sixth aspect of the present invention provides uses of the above compound of formula (I), the stereoisomer or pharmaceutically acceptable salt thereof, or a pharmaceutical composition thereof as a medicament for treating cancer; preferably, the said cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

The seventh aspect of the present invention relates to a method for treating cancer, comprising administrating the above compound of formula (I), the stereoisomer or pharmaceutically acceptable salt thereof, or the pharmaceutical composition thereof to a patient in need thereof; preferably, said cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

It is to be understood that within the scope of the present invention, the above various technical features of the present invention and the technical features specifically described hereinafter (as in the examples) may be combined with each other to constitute a new or preferred technical solution. Due to space limitations, they will not be described one by one.

DETAILED DESCRIPTION OF THE INVENTION

Based on a long-term and in-depth study, the inventors have developed for the first time an FGFR4 inhibitor with a structure of the formula (I), the series of compounds have very strong inhibitory effects on FGFR4 kinase activity and very high selectivity, and could be widely used for preparing a medicament for treating cancer, especially prostate cancer, liver cancer, pancreatic cancer, esophageal cancer, stomach cancer, lung cancer, breast cancer, ovarian cancer, colon cancer, skin cancer, glioblastoma or rhabdomyosarcoma. These compounds are expected to be developed into a new generation medicaments of FGFR4 inhibitor. On such basis, the present invention has been completed.

Detailed description: Unless otherwise stated, the following terms used in the specification and claims have the following meanings.

"Alkyl" refers to a straight or branched saturated aliphatic hydrocarbon group, for example, "$C_{1-8}$ alkyl" refers to a straight or branched alkyl having 1 to 8 carbon atoms, including but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl and various branched isomers thereof and so on.

The alkyl can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"Cycloalkyl" refers to a saturated or partially unsaturated monocyclic or polycyclic hydrocarbon substituent, for example, "$C_{3-10}$ cycloalkyl" refers to a cycloalkyl having 3-10 carbon atoms, which may be a monocyclic cycloalky and a polycyclic cycloalkyl, wherein, monocyclic cycloalkyl includes, but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and the like;

and polycyclic cycloalkyl includes spiro, fused, and bridged cycloalkyls. "Spirocycloalkyl" refers to a polycyclic group that shares a carbon atom (called a spiro atom) between the monocyclic rings. These groups may contain one or more double bonds, but none of the rings have a fully conjugated π-electron system. The spirocycloalkyl may be a monospirocycloalkyl, a bispirocycloalkyl or a polyspirocycloalkyl according to the number of common spiro atoms between the rings, spirocycloalkyl includes, but is not limited to:

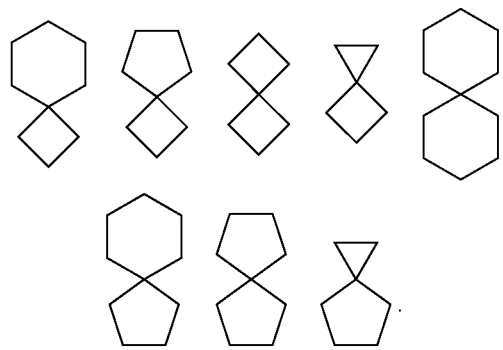

"Fused cycloalkyl" refers to an all-carbon polycyclic group in which each ring shares an adjacent pair of carbon atoms with other rings in the system, wherein one or more of the rings may contain one or more double bonds, but none of the rings have a fully conjugated π-electron system.

Depending on the number of rings, it may be bicyclic, tricyclic, tetracyclic or polycyclic, fused cycloalkyl includes but is not limited to:

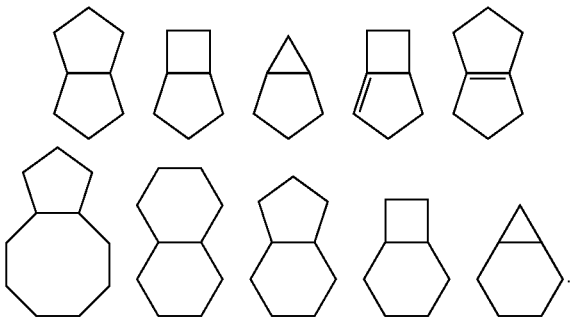

"Bridged cycloalkyl" refers to an all-carbon polycyclic group in which any two rings share two carbon atoms that are not directly bonded, which may contain one or more double bonds, but none of the rings have a fully conjugated n-electron system. Depending on the number of rings, it may be bicyclic, tricyclic, tetracyclic or polycyclic, bridged cycloalkyl includes but is not limited to: Depending on the number of rings, it may be bicyclic, tricyclic, tetracyclic or polycyclic, fused cycloalkyl includes but is not limited to:

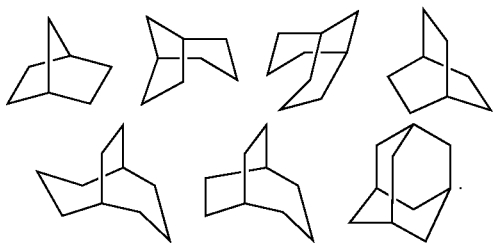

The ring of the cycloalkyl may be fused to a ring of aryl heteroaryl or heteroycloalkyl, wherein the ring attached to the parent structure is a cycloalkyl, includes, but is not limited to indanyl, tetrahydronaphthyl, benzocycloheptyl and the likes.

The cycloalkyl can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—$S(O)_rR_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —$C_{0-8}$—N($R_{12}$)—C(O)$R_{11}$ and —$C_{0-8}$—N($R_{12}$)—C(O)O$R_{10}$.

"Heterocyclyl" refers to a saturated or partially unsaturated monocyclic or polycyclic cyclic hydrocarbon substituent wherein one or more of the ring atoms are heteroatoms selected from nitrogen, oxygen or $S(O)_r$ (wherein r is an integer of 0, 1, 2), but excluding ring moiety of —O—O—, —O—S— or —S—S—, and the remaining ring atoms are carbon atoms. For example, "5-10 membered heterocyclyl" refers to a cyclic group containing 5 to 10 ring atoms, and "3-10 membered heterocyclyl" refers to a cyclic group containing 3 to 10 ring atoms.

Monocyclic heterocyclyl includes, but is not limited to pyrrolidinyl, piperidinyl, piperazinyl, morpholinyl, thiomorpholinyl, homopiperazinyl and the likes.

and polycyclic heterocyclyl includes spiro, fused, and bridged heterocyclyls. "Spiroheterocyclyl" refers to a polycyclic heterocyclyl that shares a carbon atom (called a spiro atom) between the monocyclic rings, wherein one or more of the ring atoms are heteroatoms selected from nitrogen, oxygen or $S(O)_r$ (wherein r is an integer of 0, 1, 2), and the remaining ring atoms are carbon atoms. These groups may contain one or more double bonds, but none of the rings have a fully conjugated π-electron system. The spiroheterocyclyl may be a monospiroheterocyclyl, a bispiroheterocyclyl or a polyspiroheterocyclyl according to the number of common spiro atoms between the rings, spiroheterocyclyl includes but is not limited to:

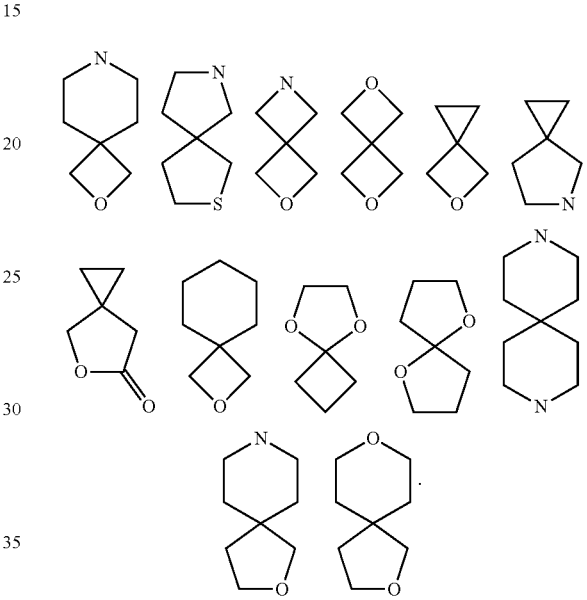

"Fused heterocyclyl" refers to a polycyclic heterocyclyl in which each ring shares an adjacent pair of carbon atoms with other rings in the system, wherein one or more of the rings may contain one or more double bonds, but none of the rings have a fully conjugated π-electron system, wherein one or more of the ring atoms are heteroatoms selected from nitrogen, oxygen or $S(O)_r$ (wherein r is an integer of 0, 1, 2), and the remaining ring atoms are carbon atoms. Depending on the number of rings, it may be bicyclic, tricyclic, tetracyclic or polycyclic, fused heterocyclyl includes, but is not limited to:

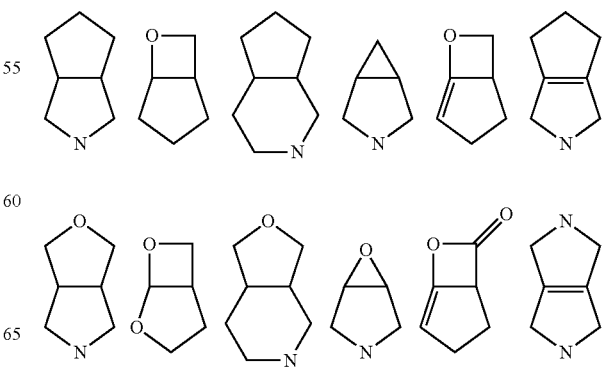

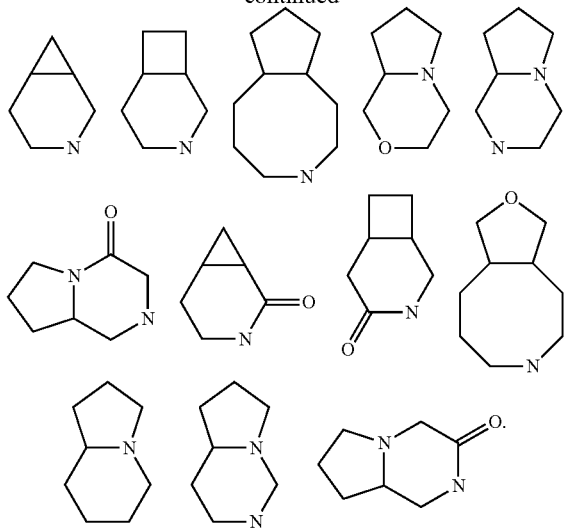

"Bridged heterocyclyl" refers to a polycyclic heterocyclyl in which any two rings share two carbon atoms that are not directly bonded, which may contain one or more double bonds, but none of the rings have a fully conjugated pi-electron system, wherein one or more of the ring atoms are heteroatoms selected from nitrogen, oxygen or $S(O)_r$ (wherein r is an integer of 0, 1, 2), and the remaining ring atoms are carbon atoms. Depending on the number of rings, it may be bicyclic, tricyclic, tetracyclic or polycyclic, bridged heterocyclyl includes, but is not limited to:

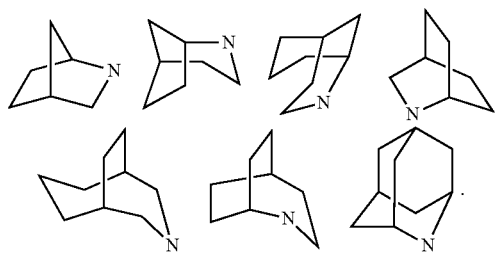

The ring of the heterocyclyl may be fused to a ring of aryl, heteroaryl or cycloalkyl wherein the ring attached to the parent structure is a heterocyclyl, includes, but is not limited to:

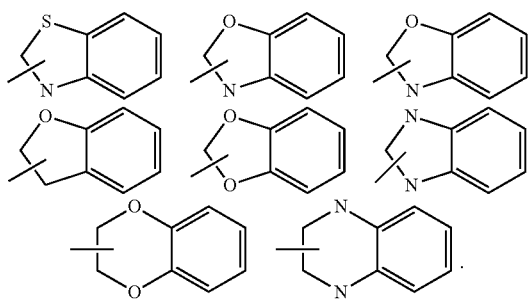

The heterocyclyl can be substituted or unsubstituted and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—$S(O)_rR_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —$C_{0-8}$—N($R_{12}$)—C(O)$R_{11}$ and —$C_{0-8}$—N($R_{12}$)—C(O)O$R_{10}$.

"Aryl" refers to an all-carbon monocyclic or fused polycyclic (ie, a ring that shares a pair of adjacent carbon atoms) group, and a polycyclic group having a conjugated π-electron system (i.e., a ring with adjacent pairs of carbon atoms), for example, "$C_{5-10}$ aryl" refers to an all-carbon aryl having 5-10 carbons, and "5-10 membered aryl" refers to an all-carbon aryl having 5-10 carbons, including but not limited to phenyl and naphthyl. The aryl ring may be fused to a ring of heteroaryl, heterocyclyl or cycloalkyl, wherein the ring attached to the parent structure is an aryl ring, includes, but is not limited to:

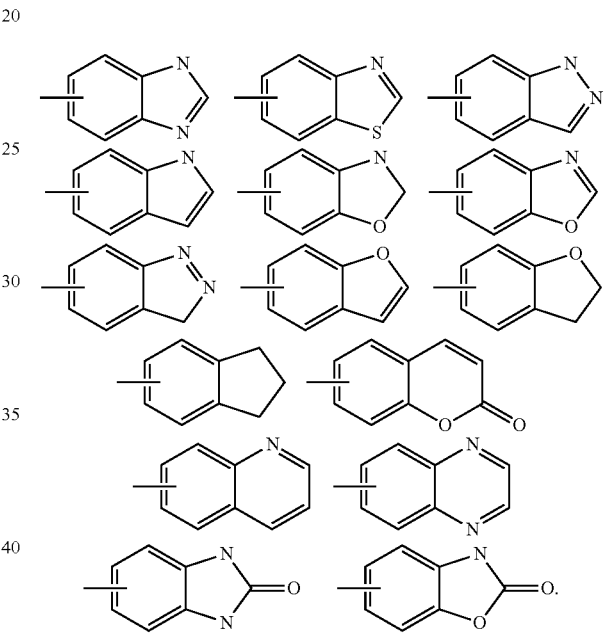

The aryl can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl $C_{2-8}$ alkynyl, $C_{3-10}$ cycloalkyl, 3-10 membered heterocyclyl, $C_{5-10}$ aryl, 5-10 membered heteroaryl, —$C_{0-8}$—$S(O)_rR_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —$C_{0-8}$—N($R_{12}$)—C(O)$R_{11}$ and —$C_{0-8}$—N($R_{12}$)—C(O)O$R_{10}$.

"Heteroaryl" refers to a heteroaromatic system containing 1 to 4 heteroatoms including a hetero atom selected from nitrogen, oxygen or S(O)r (wherein r is an integer of 0, 1, 2), for example, 5-7 membered heteroaryl refers to a heteroaromatic system containing 5 to 7 ring atoms, and 5-10 membered heteroaryl refers to a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl group or the like. The heteroaryl ring may be fused to a ring of aryl, heterocyclyl or cycloalkyl wherein the ring attached to the parent structure is a heteroaryl ring, includes, but is not limited to:

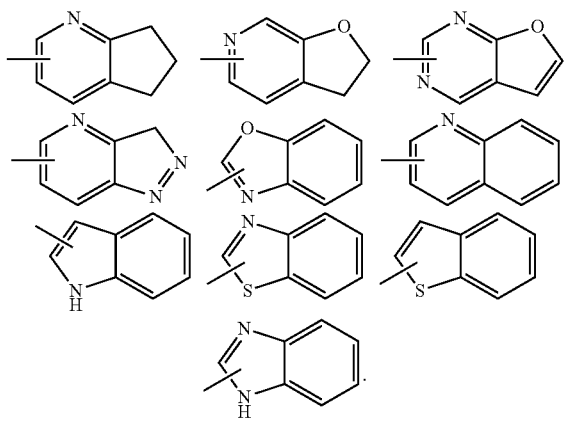

The heteroaryl can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"Alkenyl" refers to an alkyl group as defined above consisting of at least two carbon atoms and at least one carbon-carbon double bond, for example, $C_{2-8}$ alkenyl refers to a straight or branched alkenyl containing 2 to 8 carbons. Alkenyl includes, but is not limited to vinyl, 1-propenyl, 2-propenyl, 1-, 2- or 3-butenyl, and the likes.

The alkenyl can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"Alkynyl" refers to an alkyl group as defined above consisting of at least two carbon atoms and at least one carbon-carbon triple bond, for example, $C_{2-8}$ alkynyl refers to a straight or branched alkynyl containing 2 to 8 carbons. Alkynyl includes, but is not limited to ethynyl, 1-propynyl, 2-propynyl, 1-, 2- or 3-butynyl, and the likes.

The alkynyl can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"Alkoxy" refers to $-O$-(alkyl), wherein alkyl is as defined above, for example, "$C_{1-8}$ alkoxy" refers to an alkyloxy containing 1 to 8 carbons. Alkoxy includes, but is not limited to methoxy, ethoxy, propoxy, butoxy, and the likes.

The alkyloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"Cycloalkyloxy" refers to $-O$-(unsubstituted cycloalkyl), wherein cycloalkyl is as defined above, for example, "$C_{3-10}$ cycloalkyloxy" refers to a cycloalkyloxy containing 3 to 10 carbon atoms. Cycloalkyloxy includes, but is not limited to, cyclopropoxy, cyclobutyloxy, cyclopentyloxy, cyclohexyloxy and the likes.

The cycloalkyloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{13}$, $-C_{0-8}-O-C(O)Ru$, $-C_{0-8}-NR_{12}R_{13}$, $-C_{0-8}-C(O)NR_{12}R_{13}$, $-C_{0-8}-N(R_{12})-C(O)Ru$ and $-C_{0-8}-N(R_{12})-C(O)OR_{10}$.

"3-10 membered heterocyclyloxy" refers to $-O$-(unsubstituted 3-10 membered heterocyclyl), wherein 3-10 membered heterocyclyl is as defined above, 3-10 membered heterocyclyloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"$C_{5-10}$ aryloxy" refers to $-O$-(unsubstituted $C_{5-10}$ aryl), wherein $C_{5-10}$ aryl is as defined above, $C_{5-10}$ aryloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"5-10 membered heteroaryloxy" refers to $-O$-(unsubstituted 5-10 membered heteroaryl), wherein 5-10 membered heteroaryl is as defined above, 5-10 membered heteroaryloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-C_{0-8}-N(R_{12})-C(O)R_{11}$ and $-C_{0-8}-N(R_{12})-C(O)OR_{10}$.

"$C_{1-8}$ alkanoyl" refers to a monovalent group obtained by removing hydroxyl from $C_{1-8}$ alkyl acid, is also generally referred to as "$C_{0-7}-C(O)-$", for example, "$C_1-C(O)-$"

refers to acetyl; "$C_2$—C(O)—" refers to propionyl; and "$C_3$—C(O)—" refers to butyryl or isobutyryl.

"—$C_{0-8}$—S(O)$_r$R$_9$" means that the sulfur atom in —S(O)$_r$R$_9$ is bonded to $C_{0-8}$ alkyl, wherein $C_0$ alkyl means a bond, and $C_{1-8}$ alkyl is as defined above.

"—$C_{0-8}$—O—R$_{10}$" means that the oxygen atom in —O—R$_{10}$ is bonded to $C_{0-8}$ alkyl, wherein $C_0$ alkyl means a bond, and $C_{1-8}$ alkyl is as defined above.

"—$C_{0-8}$—C(O)OR$_{10}$" means that the carbonyl group in —C(O)OR$_{10}$ is bonded to $C_{0-8}$ alkyl, wherein $C_0$ alkyl means a bond, and $C_{1-8}$ alkyl is as defined above.

"—$C_{0-8}$—C(O)R$_{11}$" means that the carbonyl group in —C(O)R$_{11}$ is bonded to $C_{0-8}$ alkyl, wherein $C_0$ alkyl means a bond, and $C_{1-8}$ alkyl is as defined above.

"—$C_{0-8}$—O—C(O)R$_{13}$" means that the oxygen atom in —O—C(O)R$_{11}$ is bonded to $C_{0-8}$ alkyl, wherein $C_0$ alkyl means a bond, and $C_{1-8}$ alkyl is as defined above.

"—$C_{0-8}$—NR$_{12}$R$_{13}$" means that the nitrogen atom in —NR$_{12}$R$_{13}$ is bonded to $C_{0-8}$ alkyl, wherein $C_0$ alkyl means a bond, and $C_{1-8}$ alkyl is as defined above.

"—$C_{0-8}$—C(O)NR$_{12}$R$_{13}$" means that the carbonyl in —C(O)NR$_{12}$R$_{11}$ is bonded to $C_{0-8}$ alkyl, wherein $C_0$ alkyl means a bond, and $C_{1-8}$ alkyl is as defined above.

"—$C_{0-8}$—N(R$_{12}$)—C(O)R$_{11}$" means that the nitrogen atom in —N(R$_{12}$)—C(O)R$_{11}$ is bonded to $C_{0-8}$ alkyl, wherein $C_0$ alkyl means a bond, and $C_{1-8}$ alkyl is as defined above.

"—$C_{0-8}$—N(R$_{12}$)—C(O)OR$_{10}$" means that the nitrogen atom in —N(R$_{12}$)—C(O)OR$_{10}$ is bonded to $C_{0-8}$ alkyl, wherein $C_0$ alkyl means a bond, and $C_{1-8}$ alkyl is as defined above.

"$C_{1-8}$ haloalkyl" refers to a alkyl group having 1 to 8 carbon atoms, wherein any hydrogen atom on which is optionally substituted with F, Cl, Br or I, and includes, but is not limited to difluoromethyl, dichloromethyl, dibromomethyl, trifluoromethyl, trichloromethyl, tribromomethyl, and the likes.

"$C_{1-8}$ haloalkoxy" refers to an alkoxy having 1 to 8 carbon atoms, wherein any hydrogen atom on which is optionally substituted with F, Cl, Br or I, and includes, but is not limited to difluoromethoxy, dichloromethoxy, dibromomethoxy, trifluoromethoxy, trichloromethoxy, tribromomethoxy, and the likes.

"Halogen" refers to F, Cl, Br or I. "$H_2O$" refers to water. "THF" refers to tetrahydrofuran. "E A/EtOAc" refers to ethyl acetate. "MeOH" refers to methanol. "EtOH" refers to ethanol. "DMSO" refers to dimethyl sulfoxide. "DMF" refers to N,N-dimethylformamide. "DIPEA" refers to diisopropylethylamine. "PE" refers to petroleum ether. "$CH_2C_2$" refers to dichloromethane. "$Et_3N$" refers to triethylamine. "HOAc" refers to acetic acid. "$NaHCO_3$" refers to sodium bicarbonate. "$Na_2SO_4$" refers to sodium sulfate. "$K_2CO_3$" refers to potassium carbonate. "CuI" refers to cuprous iodide. "$Pd_2(dba)_3$" refers to tris(dibenzylideneacetone)dipalladium. "brett-phos" refers to dicyclohexyl [3,6-dimethoxy-2',4',6'-triisopropyl[1,1'-biphenyl]-2-yl]phosphine. "NBS" refers to N-bromosuccinimide. "NIS" refers to N-iodosuccinimide. "AIBN" refers to azobisisobutyronitrile. "$MeNH_2$" refers to methylamine. "$NaBH(OAc)_3$" refers to sodium borohydride acetate. "LDA" refers to lithium diisopropylamide. "$NH_4Cl$" refers to ammonium chloride. "LiOH" refers to lithium hydroxide. "$Na_2S_2O_3$" refers to sodium thiosulfate. "LiHMDS" refers to lithium hexamethyldisilazide. "EDCI" refers to 1-ethyl-(3-dimethylaminopropyl) carbodiimide hydrochloride.

"Optional" or "optionally" means that the event or environment subsequently described may, but need not, occur, including where the event or environment occurs or does not occur. For example, "heterocyclyl optionally substituted by alkyl" means that an alkyl group may be, but is not necessarily, present, and the description includes the case where the heterocyclyl is substituted with an alkyl and the case where the heterocyclyl is not substituted with an alkyl.

"Substituted" means that one or more hydrogen atoms in a group are each independently substituted with a corresponding number of substituents. It goes without saying that a substituent is only in its possible chemical position, and those skilled in the art will be able to determine (by experiment or theory) possible or impossible substitution without undue efforts. For example, it may be unstable that an amino group or a hydroxyl group having a free hydrogen is attached with a carbon atom having an unsaturated bond (such as an olefin).

"Pharmaceutical composition" refers to a mixture comprising one or more of the compounds described herein, or a physiologically/pharmaceutically acceptable salt or prodrug thereof, and other chemical components, for example physiological/pharmaceutically acceptable carriers and excipients. The purpose of the pharmaceutical composition is to promote the administration to an organism, which facilitates the absorption of the active ingredient thereby exerting biological activities.

The present invention will be further described in detail below in conjunction with the embodiment which is not intended to limit the present invention. The present invention is also not limited to the contents of the embodiments.

The structure of the compound of the present invention is determined by nuclear magnetic resonance (NMR) or/and liquid chromatography-mass spectrometry (LC-MS). The NMR chemical shift (δ) is given in parts per million (ppm). The NMR is measured by a Bruker AVANCE-400 nuclear magnetic apparatus, and the solvent is deuterated dimethyl sulfoxide (DMSO-$d_6$), deuterated methanol (CD$_3$OD) and deuterated chloroform (CDCl$_3$), and the internal standard is tetramethylsilane (TMS).

The measurement of LC-MS is performed by using an Agilent 6120 mass spectrometer. The measurement of HPLC is performed by using an Agilent 1200 DAD high pressure liquid chromatograph (Sunfire C18 150×4.6 mm column) and a Waters 2695-2996 high pressure liquid chromatograph (Gimini C18 150×4.6 mm column).

The thin layer chromatography silica gel plate is Yantai Yellow Sea HSGF254 or Qingdao GF254 silica gel plate. The specification of TLC is 0.15 mm-0.20 mm, and the specification for thin layer chromatography separation and purification is 0.4 mm-0.5 mm. 200-300 mesh silica gel (Yantai Huanghai silica gel) as a carrier is generally used in column chromatography.

The starting materials in the examples of the present invention are known and commercially available or can be prepared according to methods known in the art.

Unless otherwise stated, all reactions of the present invention are carried out under continuous magnetic stirring in dry nitrogen or argon atmosphere, the solvent is a dry solvent, and the unit of the reaction temperature is degrees Celsius (° C.).

I. Preparation of Intermediates

1. Preparation of 1-((2-(1,3-dioxolan-2-yl)-6-(methylamino)pyridin-3-yl)methyl)-4-methylpiperazin-2-one

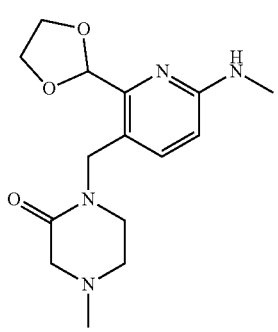 [SMILES: CNc1ccc(CN2CCN(C)CC2=O)c(C2OCCO2)n1]

Step 1: Synthesis of 3,6-dibromo-2-(dibromomethyl)pyridine

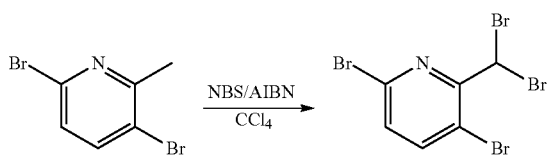

3,6-dibromo-2-methylpyridine (10.0 g, 39.86 mmol) was dissolved in tetrachloromethane (100 mL), and then NBS (14.189 g, 79.71 mmol) and AIBN (1.307 g, 7.97 mmol) were added. The mixture was heated to reflux for reaction overnight. After the reaction was completed, dichloromethane was added for dilution, and the reaction solution was successively washed with a saturated aqueous solution of sodium bicarbonate, water, and a saturated salt solution, dried over anhydrous sodium sulfate, filtered, concentrated, and separated by column chromatography [petroleum ether:ethyl acetate=5:1] to obtain 3,6-dibromo-2-(dibromomethyl) pyridine (15.0 g, yield: 92%). ESI-MS 410.0 [M+H]$^+$.

Step 2: Synthesis of 3,6-dibromopicolinaldehyde

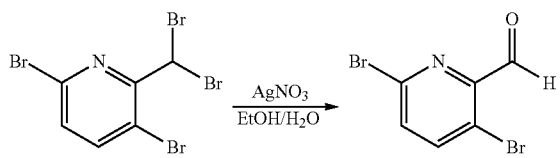

3,6-dibromo-2-(dibromomethyl)pyridine (20.0 g, 48.94 mmol) was dissolved in a mixed solvent of ethanol-water (200 mL/50 mL), then silver nitrate (16.63 g, 97.87 mmol) was added. The mixture was heated to 80° C. for reaction overnight. When the reaction was completed, the reaction solution was filtered, concentrated and then separated by column chromatography [petroleum ether:ethyl acetate=5:1] to obtain 3,6-dibromopicolinaldehyde (11.0 g, yield: 85%). ESI-MS 266.0 [M+H]$^+$.

Step 3: Synthesis of 3,6-dibromo-2-(1,3-dioxolan-2-yl)pyridine

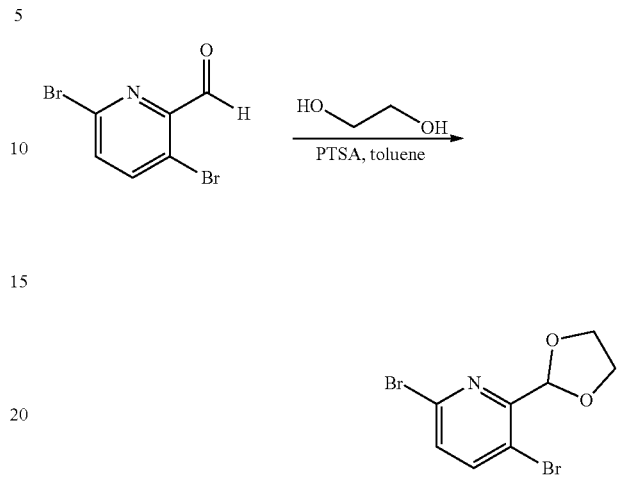

3,6-dibromopicolinaldehyde (10.0 g, 37.75 mmol) was dissolved in toluene (100 mL), and then glycol ethelene (5.85 g, 94.38 mmol) and para-toluenesulfonic acid (3.23 g, 18.88 mmol) were added. The mixture was reacted at 110° C. overnight with a water segregator. When the reaction was completed, the reaction solution was concentrated to obtain crude product 3,6-dibromo-2-(1,3-dioxolan-2-yl)pyridine, which was directly used in the next reaction. ESI-MS 310.0 [M+H]$^+$.

Step 4: Synthesis of 5-bromo-6-(1,3-dioxolan-2-yl)-N-methyl pyridin-2-amine

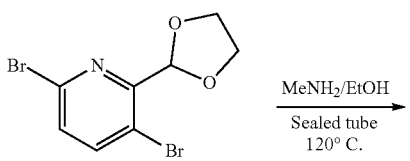

3,6-dibromo-2-(1,3-dioxolan-2-yl)pyridine (8.0 g, 25.89 mmol) was dissolved in MeNH$_2$/EtOH (70 mL, 70 M), then the mixture was transferred to a sealed system for reaction at 120° C. overnight. When the reaction was completed, the reaction solution was concentrated and separated by column chromatography [petroleum ether:ethyl acetate=2:1] to obtain 5-bromo-6-(1,3-dioxolan-2-yl)-N-methyl pyridin-2-amine (4.72 g, yield: 70%). ESI-MS 259.2, 261.2 [M+H]$^+$.

Step 5: Synthesis of 2-(1,3-dioxolan-2-yl)-6-(methyl amino)nicotinaldehyde

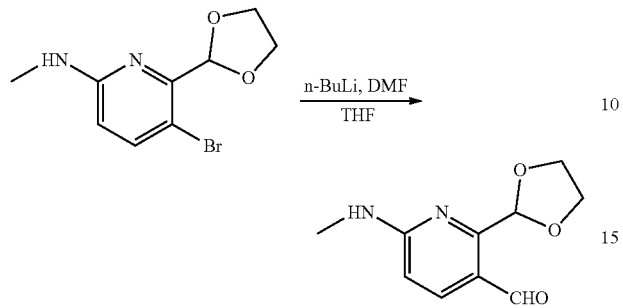

5-bromo-6-(1,3-dioxolan-2-yl)-N-methyl pyridin-2-amine (4.72 g, 18.22 mmol) was dissolved in dry THF (100 mL). After the reaction solution cooled down to −78° C., N-butyllithium (28.5 mL, 1.6 M, 45.54 mmol) was added dropwise, and the mixture was reacted at maintained low temperature for 2 hours. Then DMF (13.3 g, 182.17 mmol) was added, and the mixture was heated to room temperature slowly and reacted overnight. After the reaction was completed, saturated ammonium chloride aqueous solution was added to quench the reaction, and the reaction solution was extracted with dichloromethane for 3 times. The organic phase was combined, dried over, filtered, concentrated, and then separated by column chromatography [petroleum ether: ethyl acetate=2:1] to obtain 2-(1,3-dioxolan-2-yl)-6-(methyl amino)nicotinaldehyde (2.0 g, yield: 53%). ESI-MS 209.2 [M+H]$^+$.

Step 6: Synthesis of 1-((2-(1,3-dioxolan-2-yl)-6-(methylamino)pyridin-3-yl)methyl)-4-methylpiperazin-2-one

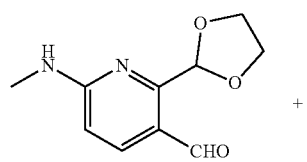 +

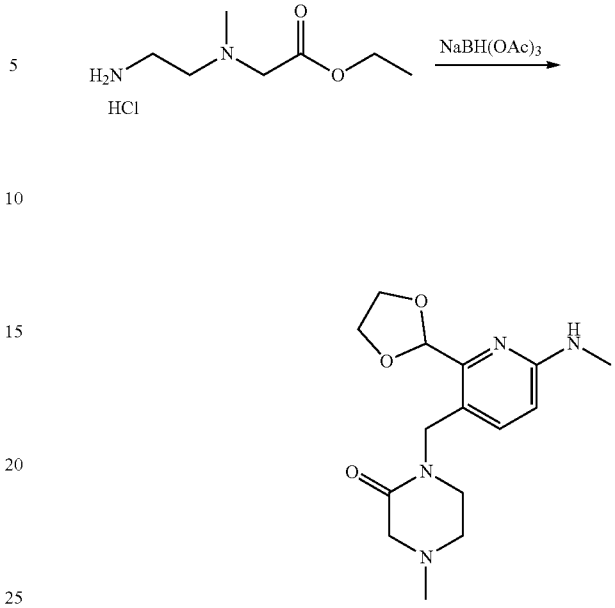

2-(1,3-dioxolan-2-yl)-6-(methylamino)nicotinaldehyde (600 mg, 2.88 mmol) and ethyl N-(2-aminoethyl)-N-methyl glycinate hydrochloric acid (1.847 g, 11.53 mmol) were dissolved in 1,2-dichloroethane (100 mL), and then DIPEA (1.859 g, 14.41 mmol), MgSO$_4$ (3.47 g, 28.82 mmol) and NaBH(OAc)$_3$ (916 mg, 4.32 mmol) were added. The mixture was reacted at room temperature overnight. After the reaction completed, a saturated NaHCO$_3$ aqueous solution was added to quench the reaction, and the reaction solution was extracted with dichloromethane for 3 times. The organic phase was combined, dried over anhydrous Na$_2$SO$_4$, filtered, concentrated, and then separated by column chromatography [dichloromethane:methanol=10:1] to obtain 1-((2-(1,3-dioxolan-2-yl)-6-(methylamino)pyridin-3-yl)methyl)-4-methylpiperain-2-one (602 mg, yield: 68%). ESI-MS 307.4 [M+H]$^+$.

Intermediates 2-5 were were prepared according to the synthesis method of Intermediate 1:

| Intermediate No. | Compound structure | Compound name | MS: m/z [M + 1]$^+$ |
|---|---|---|---|
| 2 | 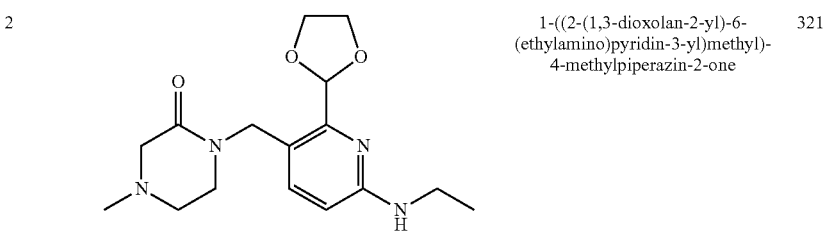 | 1-((2-(1,3-dioxolan-2-yl)-6-(ethylamino)pyridin-3-yl)methyl)-4-methylpiperazin-2-one | 321 |

| Intermediate No. | Compound structure | Compound name | MS: m/z [M + 1]+ |
|---|---|---|---|
| 3 | 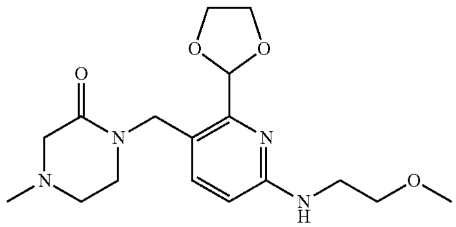 | 1-((2-(1,3-dioxolan-2-yl)-6-((2-methoxyethyl)amino)pyridin-3-yl)methyl)-4-methylpiperazin-2-one | 351 |
| 4 | 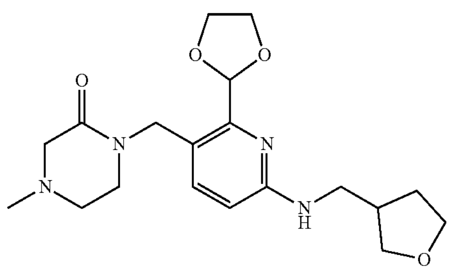 [SMILES: CN1CCN(Cc2ccc(NCC3CCOC3)nc2C2OCCO2)C(=O)C1] | 1-((2-(1,3-dioxolan-2-yl)-6-(((tetrahydrofuran-3-yl)methyl)amino)pyridin-3-yl)methyl)-4-methylpiperazin-2-one | 377 |
| 5 | 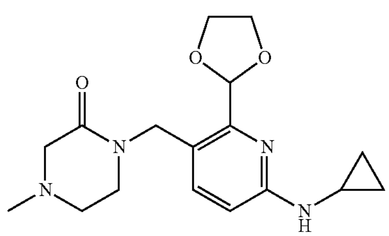 [SMILES: CN1CCN(Cc2ccc(NC3CC3)nc2C2OCCO2)C(=O)C1] | 1-((6-(cyclopropylamino)-2-(1,3-dioxolan-2-yl)pyridin-3-yl)methyl)-4-methylpiperazin-2-one | 333 |

6. Preparation of 6-amino-4-(3-methoxypyrrolidin-1-yl)nicotinonitrile

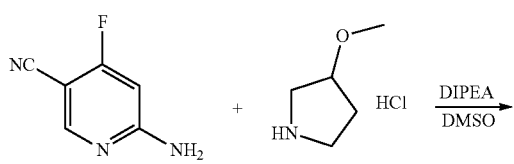

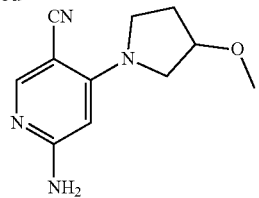

6-amino-4-fluoronicotinonitrile (200 mg, 1.46 mmol) was dissolved in DMSO (10 mL), and then 3-methoxypyrrolidine hydrochloride (603 mg, 4.38 mmol) and DIPEA (942 mg, 7.30 mmol) were added. The mixture solution was heated to 80° C., and stirred overnight. When the reaction was completed, dichloromethane was added to dilute the reaction solution, the mixture solution was successively washed with water and a saturated salt solution, the organic phase was dried over anhydrous sodium sulfate. The organic phase was filtered, concentrated, and then separated by flash silica column chromatography [$CH_2Cl_2$/MeOH 10:1] to obtain 6-amino-4-(3-methoxypyrrolidin-1-yl)nicotinonitrile (270 mg, yield: 85%). ESI-MS 219.2 [M+H]$^+$.

Intermediates 7-52 were prepared according to the synthesis method of Intermediate 6:

| Intermediate No. | Compound structure | Compound name | MS: m/z [M + 1]$^+$ |
|---|---|---|---|
| 7 | 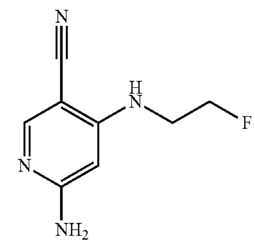 [SMILES: N#Cc1cnc(N)cc1NCCF] | 6-amino-4-((2-fluoroethyl)amino)nicotinonitrile | 181 |
| 8 | 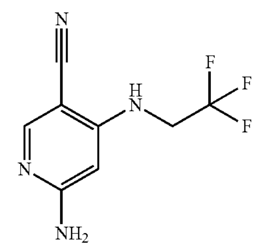 [SMILES: N#Cc1cnc(N)cc1NCC(F)(F)F] | 6-amino-4-((2,2,2-trifluoroethyl)amino)nicotinonitrile | 217 |
| 9 | 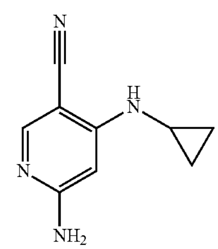 [SMILES: N#Cc1cnc(N)cc1NC1CC1] | 6-amino-4-(cyclopropylamino)nicotinonitrile | 175 |
| 10 | 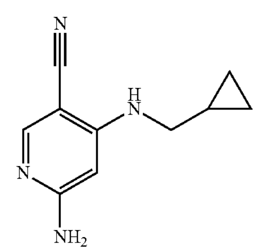 [SMILES: N#Cc1cnc(N)cc1NCC1CC1] | 6-amino-4-((cyclopropylmethyl)amino)nicotinonitrile | 189 |
| 11 | 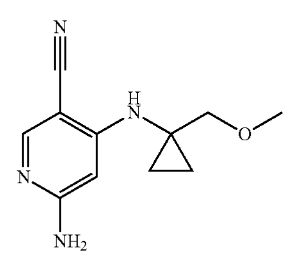 [SMILES: COCC1(Nc2cc(N)ncc2C#N)CC1] | 6-amino-4-((1-(methoxymethyl)cyclopropyl)amino)nicotinonitrile | 219 |

-continued

| Intermediate No. | Compound structure | Compound name | MS: m/z [M + 1]+ |
|---|---|---|---|
| 12 | 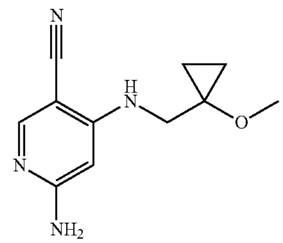 [SMILES: COC1(CNc2cc(N)ncc2C#N)CC1] | 6-amino-4-(((1-methoxycyclopropyl)methyl)amino)nicotinonitrile | 219 |
| 13 | 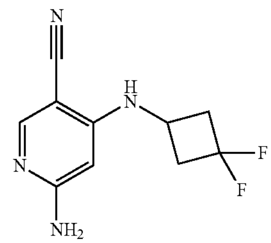 [SMILES: N#Cc1cnc(N)cc1NC1CC(F)(F)C1] | 6-amino-4-((3,3-difluorocyclobutyl)amino)nicotinonitrile | 225 |
| 14 | 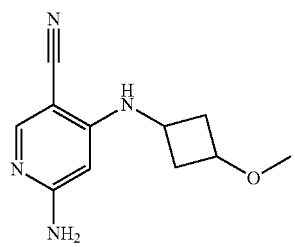 [SMILES: COC1CC(Nc2cc(N)ncc2C#N)C1] | 6-amino-4-((3-methoxycyclobutyl)amino)nicotinonitrile | 219 |
| 15 | 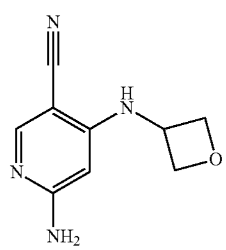 [SMILES: N#Cc1cnc(N)cc1NC1COC1] | 6-amino-4-(oxetan-3-ylamino)nicotinonitrile | 191 |
| 16 | 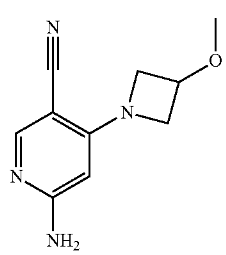 | 6-amino-4-(3-methoxyazetidin-1-yl)nicotinonitrile | 205 |
| 17 | 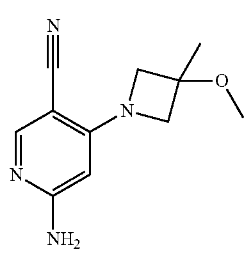 [SMILES: COC1(C)CN(c2cc(N)ncc2C#N)C1] | 6-amino-4-(3-methoxy-3-methylazetidin-1-yl)nicotinonitrile | 219 |

| Intermediate No. | Compound structure | Compound name | MS: m/z [M + 1]⁺ |
|---|---|---|---|
| 18 | 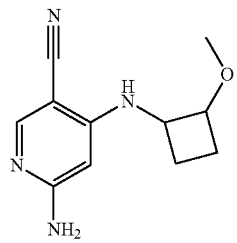 [SMILES: COC1CCC1Nc1cc(N)ncc1C#N] | 6-amino-4-((2-methoxycyclobutyl)amino)nicotinonitrile | 219 |
| 19 | 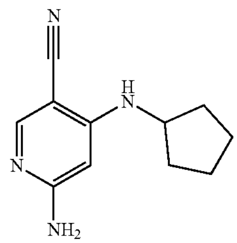 [SMILES: N#Cc1cnc(N)cc1NC1CCCC1] | 6-amino-4-(cyclopentylamino)nicotinonitrile | 203 |
| 20 | 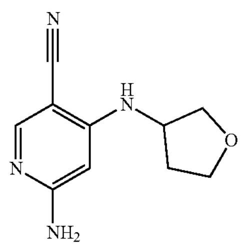 [SMILES: N#Cc1cnc(N)cc1NC1CCOC1] | 6-amino-4-((tetrahydrofuran-3-yl)amino)nicotinonitrile | 205 |
| 21 | 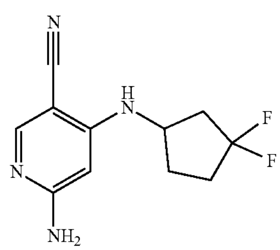 [SMILES: N#Cc1cnc(N)cc1NC1CCC(F)(F)C1] | 6-amino-4-((3,3-difluorocyclopentyl)amino)nicotinonitrile | 239 |
| 22 | 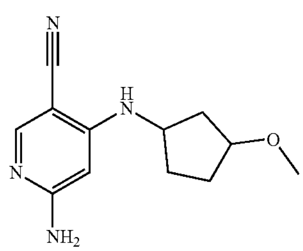 [SMILES: COC1CCC(Nc2cc(N)ncc2C#N)C1] | 6-amino-4-((3-methoxycyclopentyl)amino)nicotinonitrile | 233 |
| 23 | 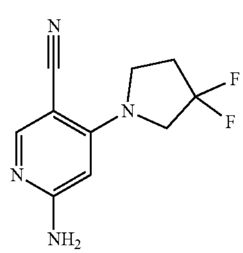 [SMILES: N#Cc1cnc(N)cc1N1CCC(F)(F)C1] | 6-amino-4-(3,3-difluoropyrrolidin-1-yl)nicotinonitrile | 225 |

-continued

| Intermediate No. | Compound structure | Compound name | MS: m/z [M + 1]+ |
|---|---|---|---|
| 24 | 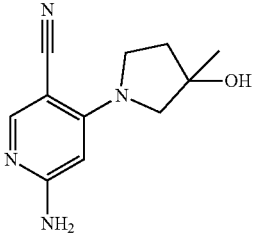 [SMILES: CC1(O)CCN(c2cc(N)ncc2C#N)C1] | 6-amino-4-(3-hydroxy-3-methylpyrrolidin-1-yl)nicotinonitrile | 219 |
| 25 | 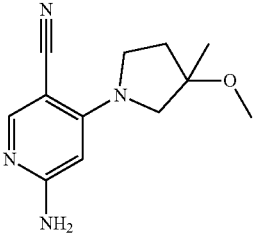 [SMILES: COC1(C)CCN(c2cc(N)ncc2C#N)C1] | 6-amino-4-(3-methoxy-3-methylpyrrolidin-1-yl)nicotinonitrile | 233 |
| 26 | 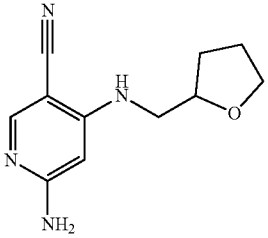 [SMILES: N#Cc1cnc(N)cc1NCC1CCCO1] | 6-amino-4-(((tetrahydrofuran-2-yl)methyl)amino)nicotinonitrile | 219 |
| 27 | 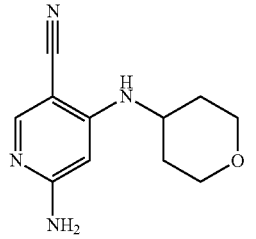 | 6-amino-4-((tetrahydro-2H-pyran-4-yl)amino)nicotinonitrile | 219 |
| 28 | 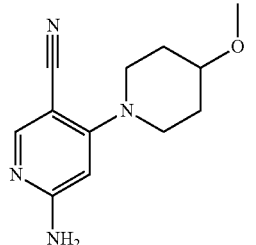 | 6-amino-4-(4-methoxypiperidin-1-yl)nicotinonitrile | 233 |
| 29 | 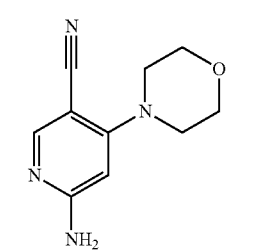 | 6-amino-4-morpholinonicotinonitrile | 205 |

-continued

| Intermediate No. | Compound structure | Compound name | MS: m/z [M + 1]+ |
|---|---|---|---|
| 30 | 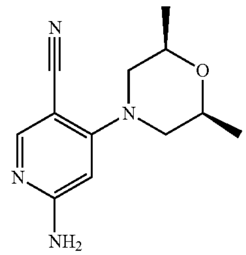 [SMILES: C[C@@H]1CN(c2cc(N)ncc2C#N)C[C@H](C)O1] | 6-amino-4-((2S,6R)-2,6-dimethylmorpholino)nicotinonitrile | 233 |
| 31 | 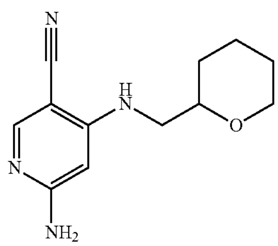 [SMILES: N#Cc1cnc(N)cc1NCC1CCCCO1] | 6-amino-4-(((tetrahydro-2H-pyran-2-yl)methyl)amino)nicotinonitrile | 233 |
| 32 | 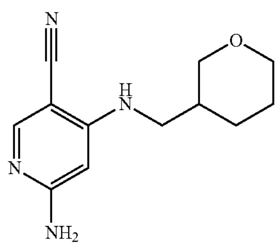 [SMILES: N#Cc1cnc(N)cc1NCC1CCCOC1] | 6-amino-4-(((tetrahydro-2H-pyran-3-yl)methyl)amino)nicotinonitrile | 233 |
| 33 | 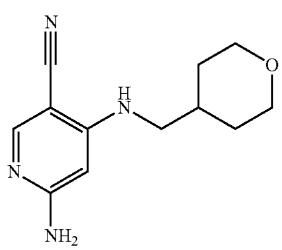 [SMILES: N#Cc1cnc(N)cc1NCC1CCOCC1] | 6-amino-4-(((tetrahydro-2H-pyran-4-yl)methyl)amino)nicotinonitrile | 233 |
| 34 | 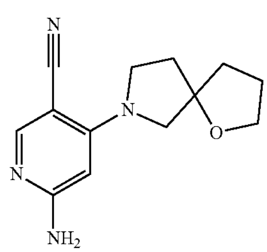 [SMILES: N#Cc1cnc(N)cc1N1CCC2(CCCO2)C1] | 6-amino-4-(1-oxa-7-azaspiro[4.4]nonan-7-yl)nicotinonitrile | 245 |
| 35 | 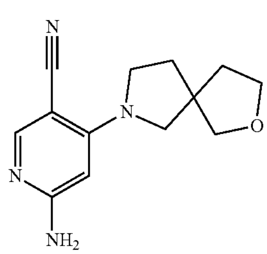 [SMILES: N#Cc1cnc(N)cc1N1CCC2(CCOC2)C1] | 6-amino-4-(2-oxa-7-azaspiro[4.4]nonan-7-yl)nicotinonitrile | 245 |

-continued

| Intermediate No. | Compound structure | Compound name | MS: m/z [M + 1]+ |
|---|---|---|---|
| 36 | 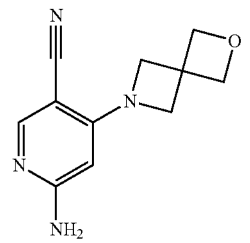 [SMILES: N#Cc1cnc(N)cc1N1CC2(COC2)C1] | 6-amino-4-(2-oxa-6-azaspiro[3.3]heptan-6-yl)nicotinonitrile | 217 |
| 37 | 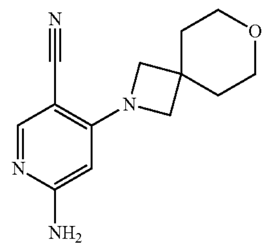 [SMILES: N#Cc1cnc(N)cc1N1CC2(CCOCC2)C1] | 6-amino-4-(7-oxa-2-azaspiro[3.5]nonan-2-yl)nicotinonitrile | 245 |
| 38 | 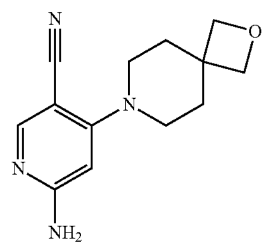 [SMILES: N#Cc1cnc(N)cc1N1CCC2(CC1)COC2] | 6-amino-4-(2-oxa-7-azaspiro[3.5]nonan-7-yl)nicotinonitrile | 245 |
| 39 | 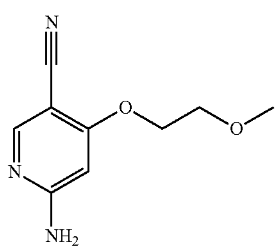 | 6-amino-4-(2-methoxyethoxy)nicotinonitrile | 194 |
| 40 | 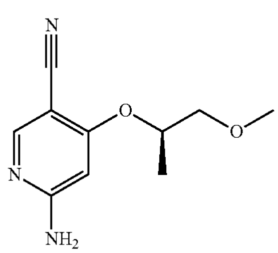 | (R)-6-amino-4-((1-methoxypropan-2-yl)oxy)nicotinonitrile | 208 |
| 41 | 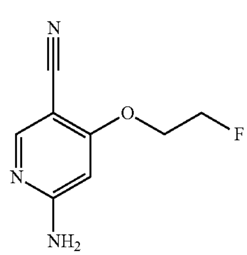 [SMILES: N#Cc1cnc(N)cc1OCCF] | 6-amino-4-(2-fluoroethoxy)nicotinonitrile | 182 |

-continued

| Intermediate No. | Compound structure | Compound name | MS: m/z [M + 1]+ |
|---|---|---|---|
| 42 | 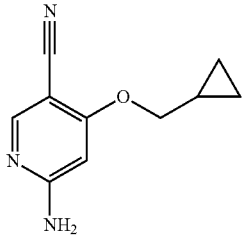 [SMILES: N#Cc1cnc(N)cc1OCC1CC1] | 6-amino-4-(cyclopropylmethoxy) nicotinonitrile | 190 |
| 43 | 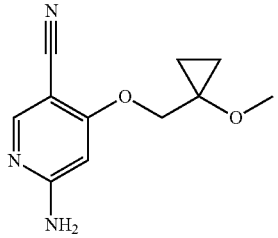 [SMILES: COC1(COc2cc(N)ncc2C#N)CC1] | 6-amino-4-((1-methoxycyclopropyl) methoxy)nicotinonitrile | 220 |
| 44 | 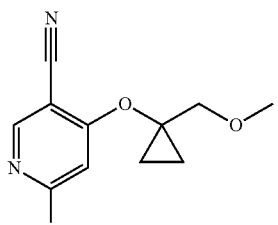 | 6-amino-4-(1-(methoxymethyl) cyclopropoxy)nicotinonitrile | 220 |
| 45 | 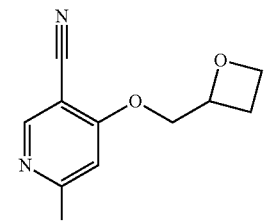 | 6-amino-4-(oxetan-2-ylmethoxy) nicotinonitrile | 206 |
| 46 | 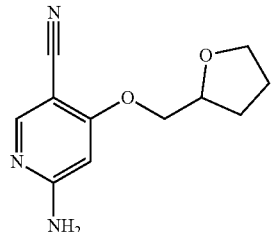 | 6-amino-4-((tetrahydrofuran-2-yl)methoxy)nicotinonitrile | 220 |
| 47 | 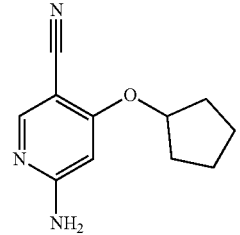 [SMILES: N#Cc1cnc(N)cc1OC1CCCC1] | 6-amino-4-(cyclopentyloxy) nicotinonitrile | 204 |

-continued

| Intermediate No. | Compound structure | Compound name | MS: m/z [M + 1]+ |
|---|---|---|---|
| 48 | 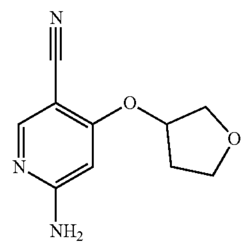 [SMILES: N#Cc1cnc(N)cc1OC1CCOC1] | 6-amino-4-((tetrahydrofuran-3-yl)oxy)nicotinonitrile | 206 |
| 49 | 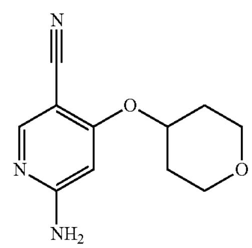 [SMILES: N#Cc1cnc(N)cc1OC1CCOCC1] | 6-amino-4-((tetrahydro-2H-pyran-4-yl)oxy)nicotinonitrile | 220 |
| 50 | 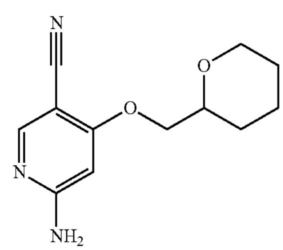 [SMILES: N#Cc1cnc(N)cc1OCC1CCCCO1] | 6-amino-4-((tetrahydro-2H-pyran-2-yl)methoxy)nicotinonitrile | 234 |
| 51 | 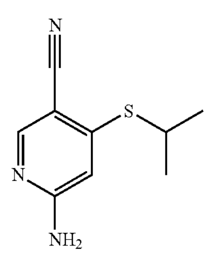 | 6-amino-4-(isopropylthio)nicotinonitrile | 194 |
| 52 | 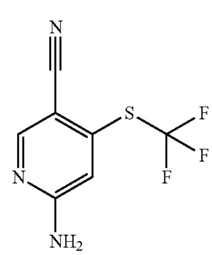 [SMILES: N#Cc1cnc(N)cc1SC(F)(F)F] | 6-amino-4-((thifluoromethyl)thio)nicotinonitrile | 220 |

53. Preparation of N⁴-cylopropyl-5-iodopyridin-2,4-diamine

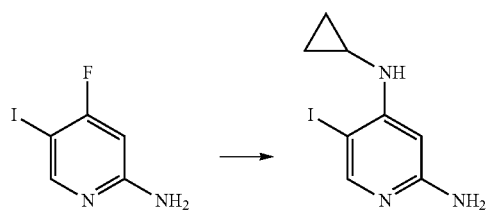

4-fluoro-5-iodopyridin-2-amine (1.4 g, 5.88 mmol) was dissolved in cyclopropylamine (20 mL), and the mixture was reacted for 96 hours under an external temperature at 80° C., the reaction solution was concentrated, and then separated by column chromatography [eluent: CH₂Cl₂~CH₂Cl₂/MeOH (20:1)] to obtain N⁴-cyclopropyl-5-iodopyridin-2,4-diamine (1.38 g, yield: 85%). MS m/z (ESI): 276.2 [M+H]⁺.

Intermediates 56-58 were prepared according to the synthesis method of Intermediate 53:

| Intermediate No. | Compound structure | Compound name | MS: m/z [M + 1]⁺ |
|---|---|---|---|
| 56 | 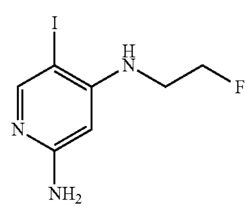 [SMILES: Nc1cc(NCCF)c(I)cn1] | N⁴-(2-fluoroethyl)-5-iodopyridin-2,4-diamine | 282 |
| 57 | 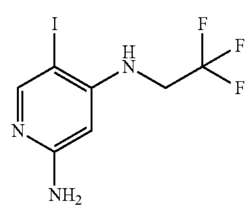 [SMILES: Nc1cc(NCC(F)(F)F)c(I)cn1] | 5-iodo-N⁴-(2,2,2-trifluoroethyl)pyridin-2,4-diamine | 318 |
| 58 | 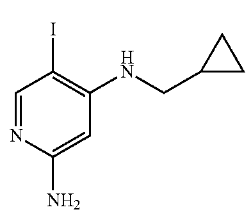 [SMILES: Nc1cc(NCC2CC2)c(I)cn1] | N⁴-(cyclopropylmethyl)-5-iodopyridin-2,4-diamine | 290 |

II. Preparation of Specific Examples

Example 1: Preparation of 3-(5-cyano-4-(cyclopropylamino)pyridin-2-yl)-1-(6-formyl-5-((4-methyl-2-oxopiperazin-1-yl)methyl)pyridin-2-yl)-1-methylurea

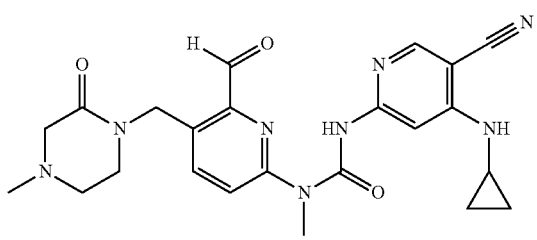 [SMILES: CN1CCN(Cc2ccc(N(C)C(=O)Nc3cc(NC4CC4)c(C#N)cn3)nc2C=O)C(=O)C1]

Step 1: Synthesis of phenyl(5-cyano-4-(cyclopropylamino)pyridin-2-yl)carbamate

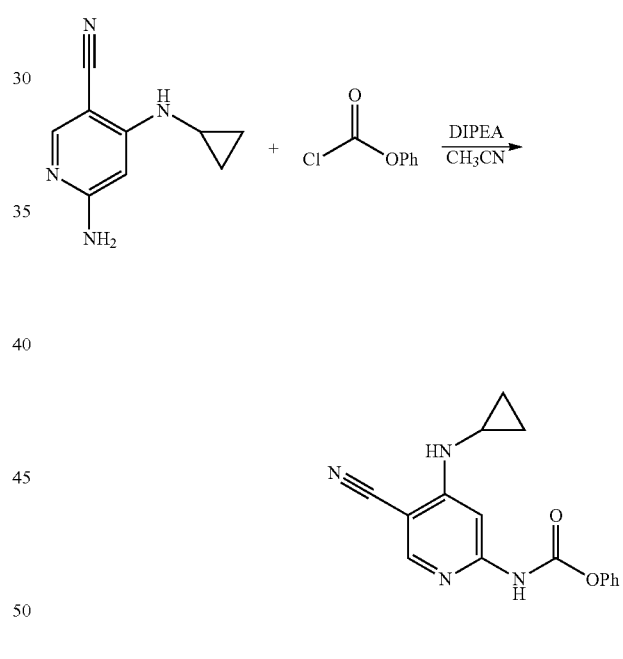

6-amino-4-(cyclopropylamino)nicotinonitrile (100 mg, 0.574 mmol) was dissolved in dry acetonitrile (10 mL), then DIPEA (222 mg, 1.722 mmol) was added, and then phenyl chloroformate (180 mg, 1.148 mmol) was added to the solution dropwise. The mixture was stirred for 1 hour at room temperature. When the reaction was completed, dichloromethane was added for dilution, and then the reaction solution was successively washed with water and a saturated sodium chloride. The organic phase was dried over anhydrous sodium sulfate, filtered, concentrated, and separated by flash silica column chromatography [petroleum ether:ethyl acetate 1:1] to obtain phenyl(5-cyano-4-(cyclopropylamino)pyridin-2-yl)carbamate (120 mg, yield: 71%). ESI-MS 295.3 [M+H]⁺.

Step 2: Synthesis of 1-(6-(1,3-dioxolan-2-yl)-5-((4-methyl-2-oxopiperazin-1-yl)methyl)pyridin-2-yl)-3-(5-cyano-4-(cyclopropylamino)pyridin-2-yl)-1-methylurea Step 3: Synthesis of 3-(5-cyano-4-(cyclopropylamino)pyridin-2-yl)-1-(6-formyl-5-((4-methyl-2-oxopiperazin-1-yl)methyl)pyridin-2-yl)-1-methylurea

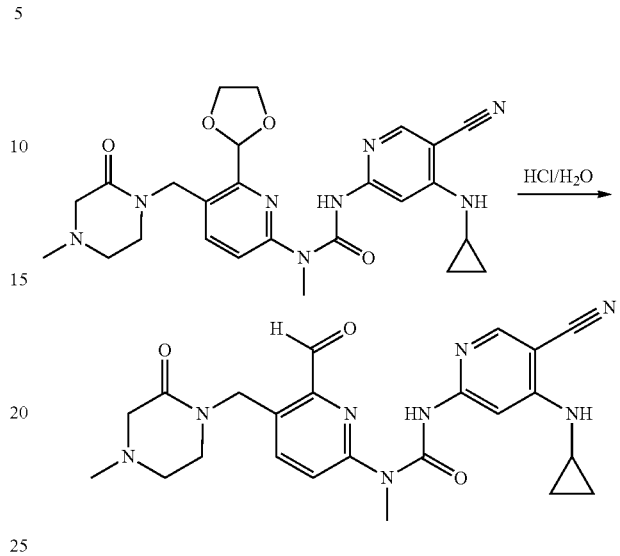

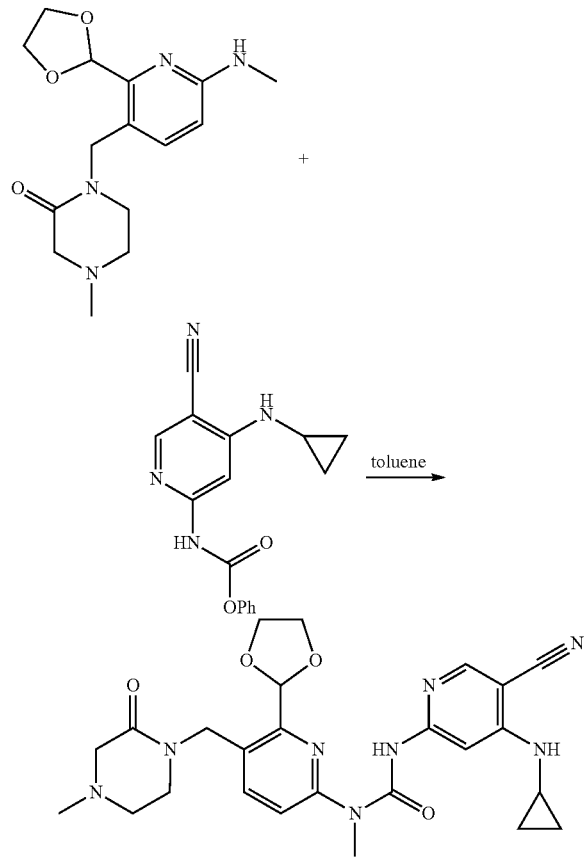

1-((2-(1,3-dioxolan-2-yl)-6-(methylamino)pyridin-3-yl)methyl)-4-methylpiperazin-2-one (40 mg, 0.131 mmol) and phenyl(5-cyano-4-(cyclopropylamino)pyridin-2-yl)carbamate (38 mg, 0.131 mmol) were dissolved in dry toluene (10 mL). The mixture was heated to 120° C. with microwave and reacted for 5 hours. When the reaction was completed, the reaction solution was concentrated and separated by PTLC [dichloromethane:methanol=10:1] to obtain crude product 1-(6-(1,3-dioxolan-2-yl)-5-((4-methyl-2-oxopiperazin-1-yl)methyl)pyridin-2-yl)-3-(5-cyano-4-(cyclopropylamino)pyridin-2-yl)-1-methylurea (14 mg, yield: 21%). ESI-MS 507.6 [M+H]+.

1-(6-(1,3-dioxolan-2-yl)-5-((4-methyl-2-oxopiperazin-1-yl)methyl)pyridin-2-yl)-3-(5-cyano-4-(cyclopropylamino)pyridin-2-yl)-1-methyurea (14 mg, 0.028 mmol) was dissolved in a mixed solvent of THF/H$_2$O (10 mL, 4:1), and then 3 drops of concentrated hydrochloric acid was added. The mixture was stirred overnight for reaction at room temperature. When the reaction was completed, a saturated sodium bicarbonate was added to neutralize the reaction solution to weak alkaline, then the reaction solution was extracted with dichloromethane for 3 times, the organic phase was combined, successively washed with water and a saturated salt solution, and dried over anhydrous sodium sulfate. The organic phase was filtered, concentrated and separated by PTLC [dichloromethane:methanol=10:1] to obtain 3-(5-cyan o-4-(cyclopropylamino) pyridin-2-yl)-1-(6-formyl-5-((4-methyl-2-oxopiperazin-1-yl)methyl)pyrid in-2-yl)-1-methylurea (8 mg, yield: 62%). ESI-MS 463.4 [M+H]+.

$^1$H NMR (400 MHz, CDCl$_3$) δ 13.03 (s, 1H), 10.26 (s, 1H), 8.17 (s, 1H), 7.98 (d, J=8.7 Hz, 1H), 7.91 (s, 1H), 7.30 (d, J=8.7 Hz, 1H), 5.30 (d, J=3.3 Hz, 1H), 5.11 (s, 2H), 3.53 (s, 3H), 3.49 (s, 1H), 3.47-3.42 (m, 1H), 3.30-3.26 (m, 2H), 2.82-2.74 (m, 2H), 2.70-251 (m, 1H), 2.43 (s, 31-), 0.99-0.94 (m, 211), 0.69-0.65 (m, 21-).

Examples 2-51 were prepared according to the synthesis method of Example 1:

| Example No. | Compound structure | Compound name | MS: m/z [M + 1]+ |
|---|---|---|---|
| 2 | 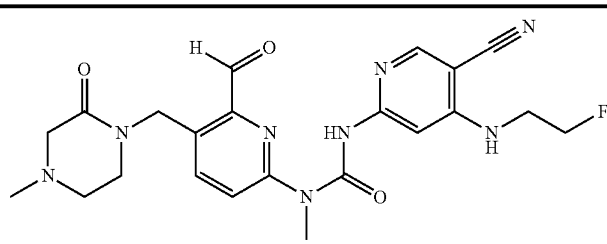 | 3-(5-cyano-4-((2-fluoroethyl)amino)pyridin-2-yl)-1-(6-formyl-5-((4-methyl-2-oxopiperazin-1-yl)methyl)pyridin-2-yl)-1-methylurea | 469 |

-continued

| Example No. | Compound structure | Compound name | MS: m/z [M + 1]+ |
|---|---|---|---|
| 3 | 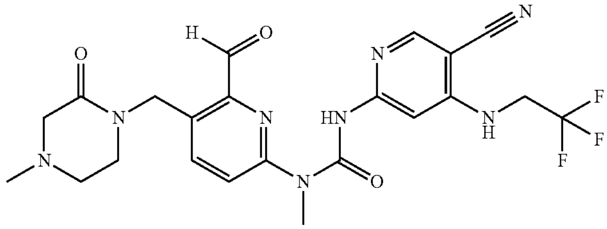 [SMILES: CN1CCN(Cc2ccc(N(C)C(=O)Nc3cc(NCC(F)(F)F)c(C#N)cn3)nc2C=O)C(=O)C1] | 3-(5-cyano-4-((2,2,2-trifluomethyl)amino) pyridin-2-yl)-1-(6-formyl-5-((4-methyl-2-oxopiperazin-1-yl)methyl)pyridin-2-yl)-1-methylurea | 505 |
| 4 | 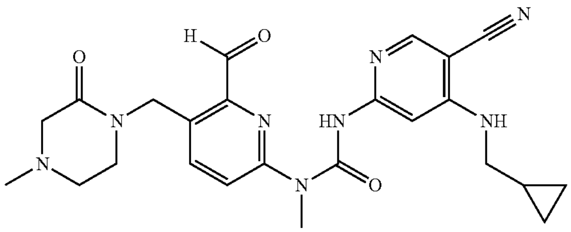 [SMILES: CN1CCN(Cc2ccc(N(C)C(=O)Nc3cc(NCC4CC4)c(C#N)cn3)nc2C=O)C(=O)C1] | 3-(5-cyano-4-((cyclopropylmethyl)amino) pyridin-2-yl)-1-(6-formyl-5-((4-methyl-2-oxopiperazin-1-yl)methyl)pyridin-2-yl)-1-methylurea | 477 |
| 5 | 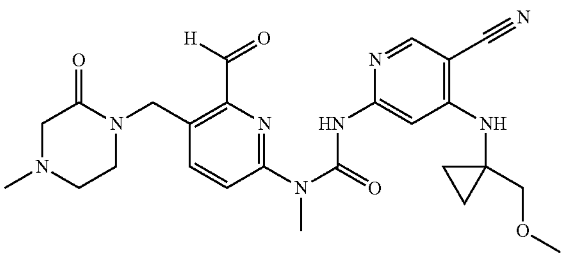 | 3-(5-cyano-4-((1-(methoxymethyl) cyclopropyl)amino)pyridin-2-yl)-1-(6-formyl-5-((4-methyl-2-oxopiperazin-1-yl)methyl) pyridin-2-yl)-1-methylurea | 507 |
| 6 | 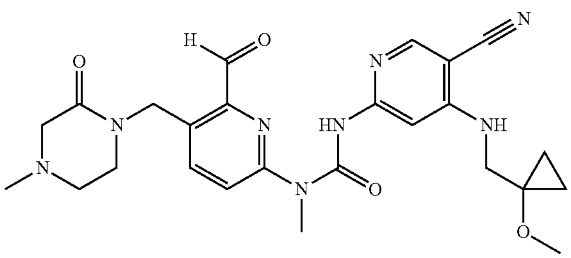 [SMILES: COC1(CNc2cc(NC(=O)N(C)c3ccc(CN4CCN(C)CC4=O)c(C=O)n3)ncc2C#N)CC1] | 3-(5-cyano-4-(((1-methoxycyclopropyl) methyl)amino)pyridin-2-yl)-1-(6-formyl-5-((4-methyl-2-oxopiperazin-1-yl)methyl) pyridin-2-yl)-1-methylurea | 507 |
| 7 | 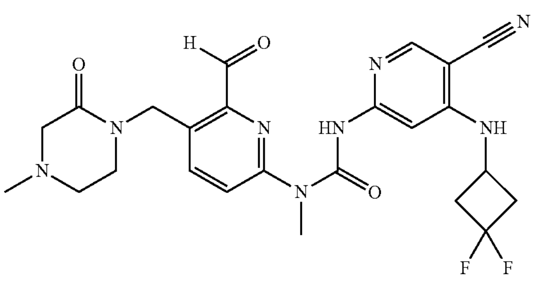 [SMILES: CN1CCN(Cc2ccc(N(C)C(=O)Nc3cc(NC4CC(F)(F)C4)c(C#N)cn3)nc2C=O)C(=O)C1] | 3-(5-cyano-4-((3,3-difluorocyclobutyl) amino)pyridin-2-yl)-1-(6-formyl-5-((4-methyl-2-oxopiperazin-1-yl)methyl)pyridin-2-yl)-1-methylurea | 513 |
| 8 | 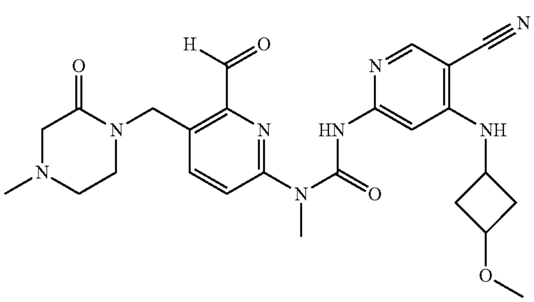 | 3-(5-cyano-4-((3-methoxycyclobutyl) amino)pyridin-2-yl)-1-(6-formyl-5-((4-methyl-2-oxopiperazin-1-yl)methyl)pyridin-2-yl)-1-methylurea | 507 |

-continued

| Example No. | Compound structure | Compound name | MS: m/z [M + 1]+ |
|---|---|---|---|
| 9 | 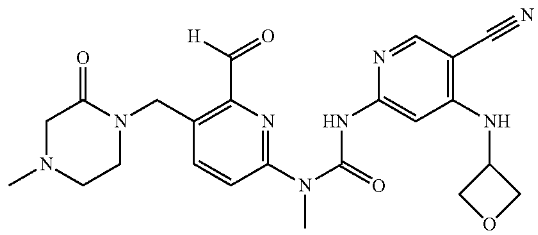 [SMILES: CN1CCN(Cc2ccc(N(C)C(=O)Nc3cc(NC4COC4)c(C#N)cn3)nc2C=O)C(=O)C1] | 3-(5-cyano-4-(oxetan-3-ylamino)pyridin-2-yl)-1-(6-formyl-5-((4-methyl-2-oxopiperazin-1-yl)methyl)pyridin-2-yl)-1-methylurea | 479 |
| 10 | 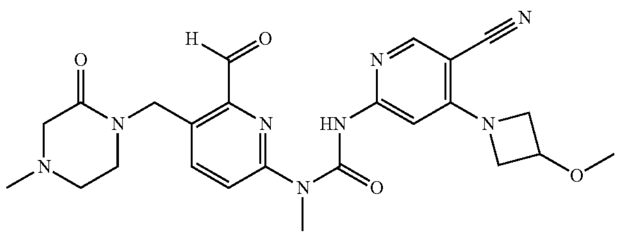 | 3-(5-cyano-4-(3-methoxyazetidin-1-yl)pyridin-2-yl)-1-(6-formyl-5-((4-methyl-2-oxopiperazin-1-yl)methyl)pyridin-2-yl)-1-methylurea | 493 |
| 11 | 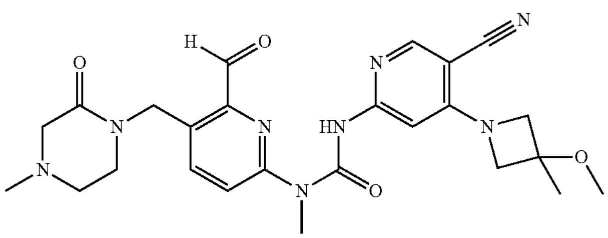 | 3-(5-cyano-4-(3-methoxy-3-methylazetidin-1-yl)pyridin-2-yl)-1-(6-formyl-5-((4-methyl-2-oxopiperazin-1-yl)methyl)pyridin-2-yl)-1-methylurea | 507 |
| 12 | 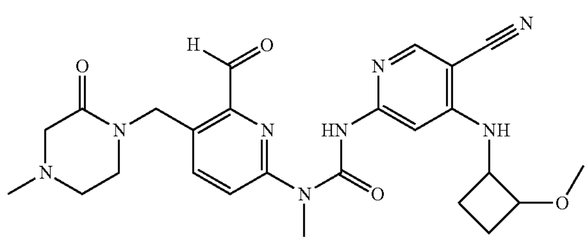 | 3-(5-cyano-4-((2-methoxycyclobutyl)amino)pyridin-2-yl)-1-(6-formyl-5-((4-methyl-2-oxopiperazin-1-yl)methyl)pyridin-2-yl)-1-methylurea | 507 |
| 13 | 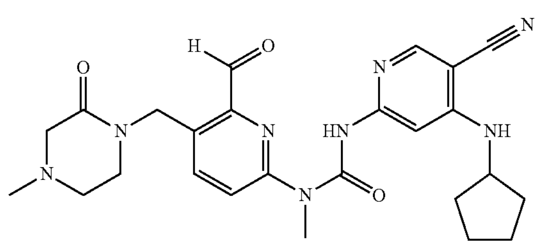 [SMILES: CN1CCN(Cc2ccc(N(C)C(=O)Nc3cc(NC4CCCC4)c(C#N)cn3)nc2C=O)C(=O)C1] | 3-(5-cyano-4-(cyclopentylamino)pyridin-2-yl)-1-(6-formyl-5-((4-methyl-2-oxopiperazin-1-yl)methyl)pyridin-2-yl)-1-methylurea | 491 |
| 14 | 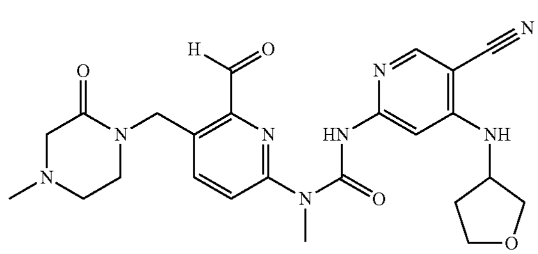 [SMILES: CN1CCN(Cc2ccc(N(C)C(=O)Nc3cc(NC4CCOC4)c(C#N)cn3)nc2C=O)C(=O)C1] | 3-(5-cyano-4-((tetrahydrofuran-3-yl)amino)pyridin-2-yl)-1-(6-formyl-5-((4-methyl-2-oxopiperazin-1-yl)methyl)pyridin-2-yl)-1-methylurea | 493 |

| Example No. | Compound structure | Compound name | MS: m/z [M + 1]+ |
|---|---|---|---|
| 15 | 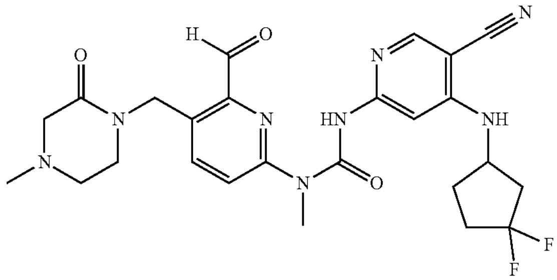 [SMILES: CN1CCN(Cc2ccc(N(C)C(=O)Nc3cc(NC4CCC(F)(F)C4)c(C#N)cn3)nc2C=O)C(=O)C1] | 3-(5-cyano-4-((3,3-difluorocyclopentyl) amino)pyridin-2-yl)-1-(6-formyl-5-((4-methyl-2-oxopiperazin-1-yl)methyl) pyridin-2-yl)-1-methylurea | 527 |
| 16 | 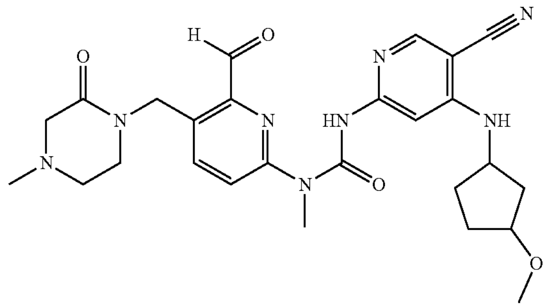 [SMILES: COC1CCC(Nc2cc(NC(=O)N(C)c3ccc(CN4CCN(C)CC4=O)c(C=O)n3)ncc2C#N)C1] | 3-(5-cyano-4-((3-methoxycyclopentyl) amino)pyridin-2-yl)-1-(6-formyl-5-((4-methyl-2-oxopiperazin-1-yl)methyl)pyridin-2-yl)-1-methylurea | 521 |
| 17 | 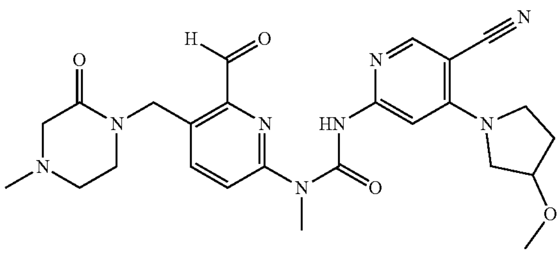 [SMILES: COC1CCN(c2cc(NC(=O)N(C)c3ccc(CN4CCN(C)CC4=O)c(C=O)n3)ncc2C#N)C1] | 3-(5-cyano-4-(3-methoxypyrrolidin-1-yl) pyridin-2-yl)-1-(6-formyl-5-((4-methyl-2-oxopiperazin-1-yl)methyl)pyridin-2-yl)-1-methylurea | 507 |
| 18 | 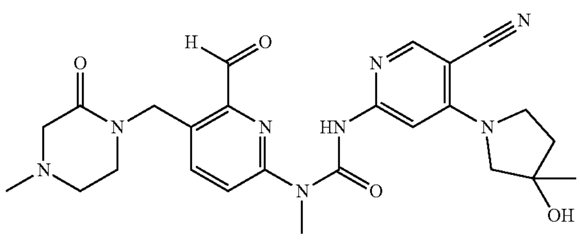 | 3-(5-cyano-4-(3-hydroxy-3-methylpyrrolidin-1-yl)pyridin-2-yl)-1-(6-formyl-5-((4-methyl-2-oxopiperazin-1-yl)methyl) pyridin-2-yl)-1-methylurea | 507 |
| 19 | 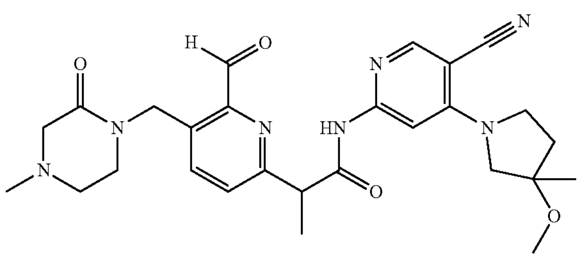 | 3-(5-cyano-4-(3-methoxy-3-methylpyrrolidin-1-yl)pyridin-2-yl)-1-(6-formyl-5-((4-methyl-2-oxopiperazin-1-yl)methyl) pyridin-2-yl)-1-methylurea | 521 |
| 20 | 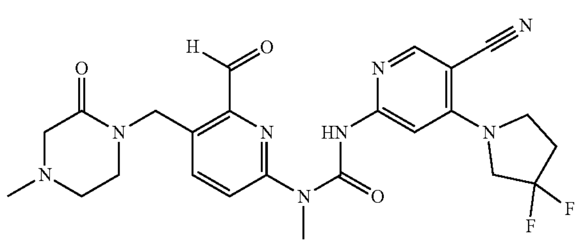 [SMILES: CN1CCN(Cc2ccc(N(C)C(=O)Nc3cc(N4CCC(F)(F)C4)c(C#N)cn3)nc2C=O)C(=O)C1] | 3-(5-cyano-4-(3,3-difluoropyrrolidin-1-yl)pyridin-2-yl)-1-(6-formyl-5-((4-methyl-2-oxopiperazin-1-yl)methyl)pyridin-2-yl)-1-methylurea | 513 |

| Example No. | Compound structure | Compound name | MS: m/z [M + 1]+ |
|---|---|---|---|
| 21 | 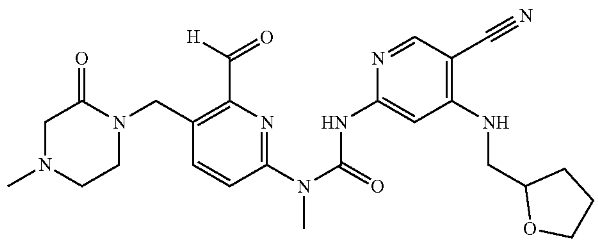 [SMILES: CN1CCN(Cc2ccc(N(C)C(=O)Nc3cc(NCC4CCCO4)c(C#N)cn3)nc2C=O)C(=O)C1] | 3-(5-cyano-4-(((tetrahydrofuran-2-yl)methyl)amino)pyridin-2-yl)-1-(6-formyl-5-((4-methyl-2-oxopiperazin-1-yl)methyl)pyridin-2-yl)-1-methylurea | 507 |
| 22 | 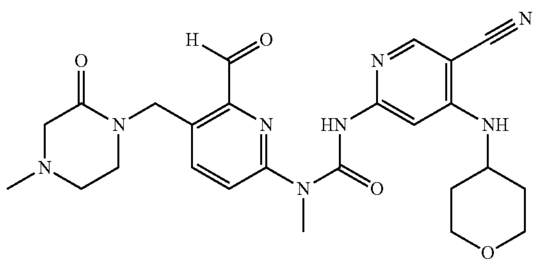 [SMILES: CN1CCN(Cc2ccc(N(C)C(=O)Nc3cc(NC4CCOCC4)c(C#N)cn3)nc2C=O)C(=O)C1] | 3-(5-cyano-4-((tetrahydro-2H-pyran-4-yl)amino)pyridin-2-yl)-1-(6-formyl-5-((4-methyl-2-oxopiperazin-1-yl)methyl)pyridin-2-yl)-1-methylurea | 507 |
| 23 | 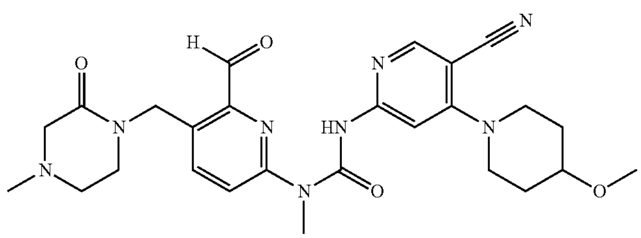 | 3-(5-cyano-4-(4-methoxypiperidin-1-yl)pyridin-2-yl)-1-(6-formyl-5-((4-methyl-2-oxopiperazin-1-yl)methyl)pyridin-2-yl)-1-methylurea | 521 |
| 24 | 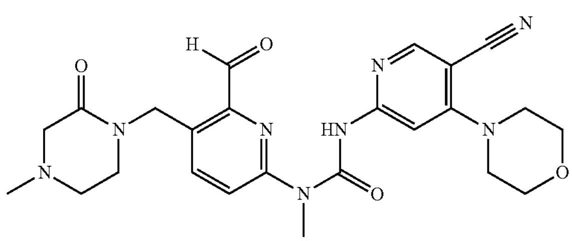 [SMILES: CN1CCN(Cc2ccc(N(C)C(=O)Nc3cc(N4CCOCC4)c(C#N)cn3)nc2C=O)C(=O)C1] | 3-(5-cyano-4-morpholinopyridin-2-yl)-1-(6-formyl-5-((4-methyl-2-oxopiperazin-1-yl)methyl)pyridin-2-yl)-1-methylurea | 493 |
| 25 | 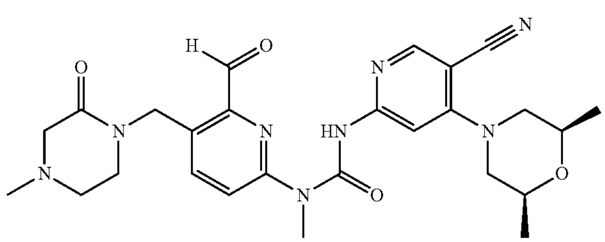 | 3-(5-cyano-4-((2S,6R)-2,6-dimethylmorpholino)pyridin-2-yl)-1-(6-formyl-5-((4-methyl-2-oxopiperazin-1-yl)methyl)pyridin-2-yl)-1-methylurea | 521 |
| 26 | 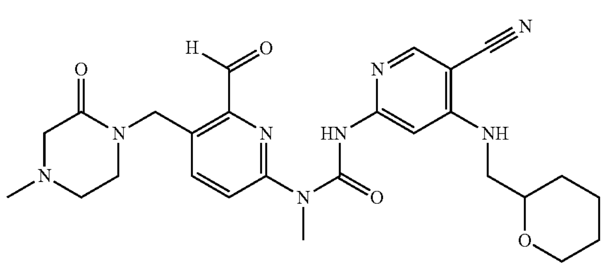 [SMILES: CN1CCN(Cc2ccc(N(C)C(=O)Nc3cc(NCC4CCCCO4)c(C#N)cn3)nc2C=O)C(=O)C1] | 3-(5-cyano-4-(((tetrahydro-2H-pyran-2-yl)methyl)amino)pyridin-2-yl)-1-(6-formyl-5-((4-methyl-2-oxopiperazin-1-yl)methyl)pyridin-2-yl)-1-methylurea | 521 |

-continued

| Example No. | Compound structure | Compound name | MS: m/z [M + 1]+ |
|---|---|---|---|
| 27 | 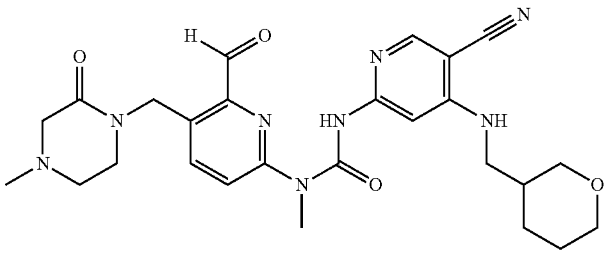 [SMILES: CN1CCN(Cc2ccc(N(C)C(=O)Nc3cc(NCC4CCCOC4)c(C#N)cn3)nc2C=O)C(=O)C1] | 3-(5-cyano-4-(((tetrahydro-2H-pyran-3-yl)methyl)amino)pyridin-2-yl)-1-(6-formyl-5-((4-methyl-2-oxopiperazin-1-yl)methyl)pyridin-2-yl)-1-methylurea | 521 |
| 28 | 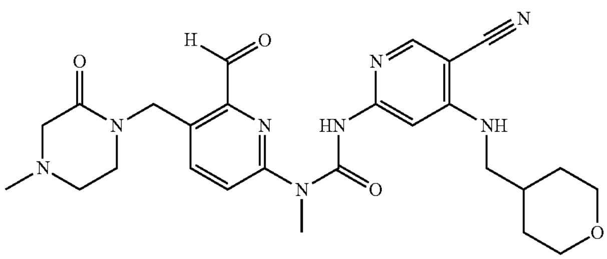 [SMILES: CN1CCN(Cc2ccc(N(C)C(=O)Nc3cc(NCC4CCOCC4)c(C#N)cn3)nc2C=O)C(=O)C1] | 3-(5-cyano-4-(((tetrahydro-2H-pyran-4-yl)methyl)amino)pyridin-2-yl)-1-(6-formyl-5-((4-methyl-2-oxopiperazin-1-yl)methyl)pyridin-2-yl)-1-methylurea | 521 |
| 29 | 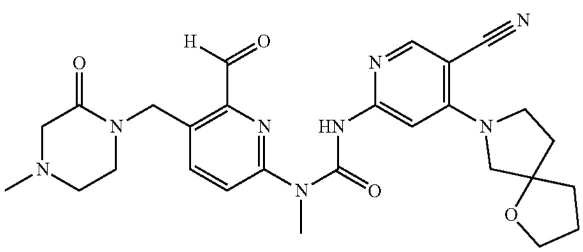 [SMILES: CN1CCN(Cc2ccc(N(C)C(=O)Nc3cc(N4CCC5(CCCO5)C4)c(C#N)cn3)nc2C=O)C(=O)C1] | 3-(5-cyano-4-(1-oxa-7-azaspiro[4.4]nonan-7-yl)pyridin-2-yl)-1-(6-formyl-5-((4-methyl-2-oxopiperazin-1-yl)methyl)pyridin-2-yl)-1-methylurea | 533 |
| 30 | 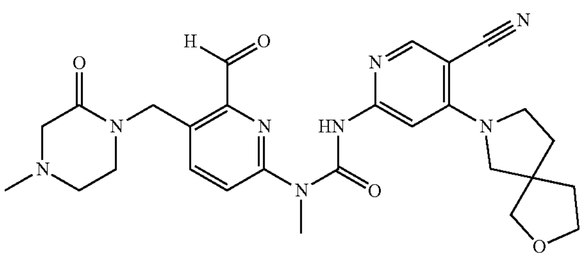 [SMILES: CN1CCN(Cc2ccc(N(C)C(=O)Nc3cc(N4CCC5(CCOC5)C4)c(C#N)cn3)nc2C=O)C(=O)C1] | 3-(5-cyano-4-(2-oxa-7-azaspiro[4.4]nonan-7-yl)pyridin-2-yl)-1-(6-formyl-5-((4-methyl-2-oxopiperazin-1-yl)methyl)pyridin-2-yl)-1-methylurea | 533 |
| 31 | 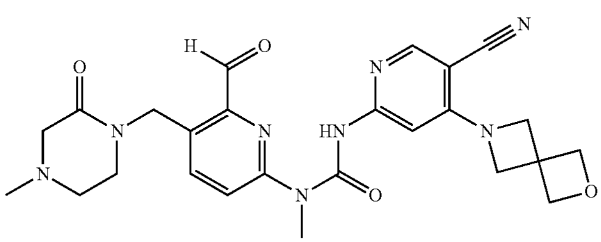 [SMILES: CN1CCN(Cc2ccc(N(C)C(=O)Nc3cc(N4CC5(COC5)C4)c(C#N)cn3)nc2C=O)C(=O)C1] | 3-(5-cyano-4-(2-oxa-6-azaspiro[3.3]heptan-6-yl)pyridin-2-yl)-1-(6-formyl-5-((4-methyl-2-oxopiperazin-1-yl)methyl)pyridin-2-yl)-1-methylurea | 505 |
| 32 | 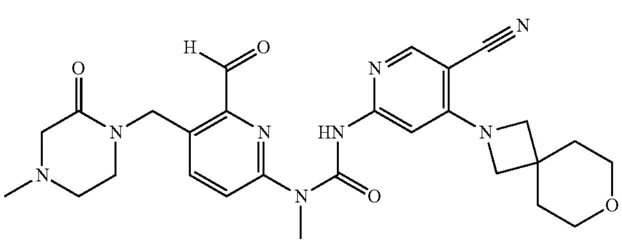 [SMILES: CN1CCN(Cc2ccc(N(C)C(=O)Nc3cc(N4CC5(CCOCC5)C4)c(C#N)cn3)nc2C=O)C(=O)C1] | 3-(5-cyano-4-(7-oxa-2-azaspiro[3.5]nonan-2-yl)pyridin-2-yl)-1-(6-formyl-5-((4-methyl-2-oxopiperazin-1-yl)methyl)pyridin-2-yl)-1-methylurea | 533 |

| Example No. | Compound structure | Compound name | MS: m/z [M + 1]+ |
|---|---|---|---|
| 33 | 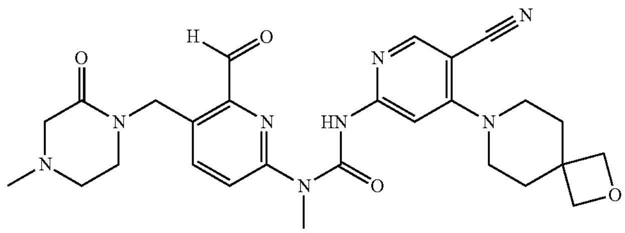 [SMILES: CN1CCN(Cc2ccc(N(C)C(=O)Nc3cc(N4CCC5(CC4)COC5)c(C#N)cn3)nc2C=O)C(=O)C1] | 3-(5-cyano-4-(2-oxa-7-azaspiro[3.5]nonan-7-yl)pyridin-2-yl)-1-(6-formyl-5-((4-methyl-2-oxopiperazin-1-yl)methyl)pyridin-2-yl)-1-methylurea | 533 |
| 34 | 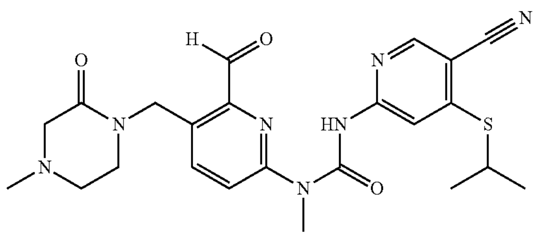 [SMILES: CC(C)Sc1cc(NC(=O)N(C)c2ccc(CN3CCN(C)CC3=O)c(C=O)n2)ncc1C#N] | 3-(5-cyano-4-(isopropylthio)pyridin-2-yl)-1-(6-formyl-5-((4-methyl-2-oxopiperazin-1-yl)methyl)pyridin-2-yl)-1-methylurea | 482 |
| 35 | 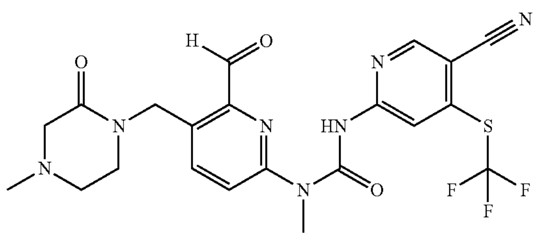 [SMILES: CN1CCN(Cc2ccc(N(C)C(=O)Nc3cc(SC(F)(F)F)c(C#N)cn3)nc2C=O)C(=O)C1] | 3-(5-cyano-4-((trifluoromethyl)thio)pyridin-2-yl)-1-(6-formyl-5-((4-methyl-2-oxopiperazin-1-yl)methyl)pyridin-2-yl)-1-methylurea | 508 |
| 36 | 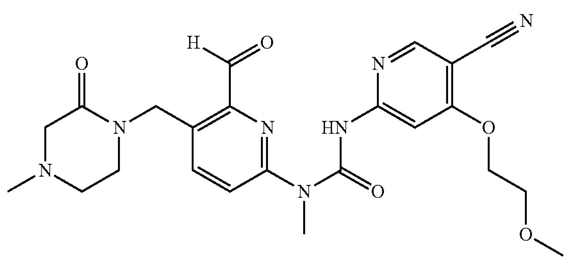 | 3-(5-cyano-4-(2-methoxyethoxy)pyridin-2-yl)-1-(6-formyl-5-((4-methyl-2-oxopiperazin-1-yl)methyl)pyridin-2-yl)-1-methylurea | 482 |
| 37 | 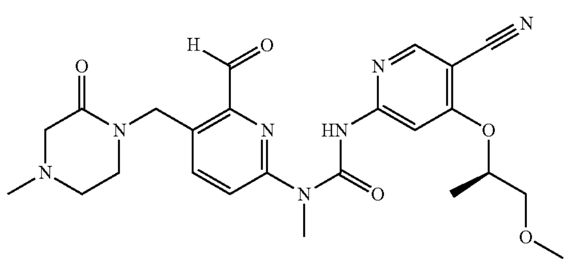 | (R)-3-(5-cyano-4-((1-methoxypropan-2-yl)oxy)pyridin-2-yl)-1-(6-formyl-5-((4-methyl-2-oxopiperazin-1-yl)methyl)pyridin-2-yl)-1-methylurea | 496 |
| 38 | 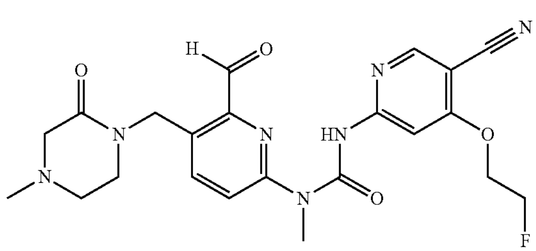 [SMILES: CN1CCN(Cc2ccc(N(C)C(=O)Nc3cc(OCCF)c(C#N)cn3)nc2C=O)C(=O)C1] | 3-(5-cyano-4-(2-fluoroethoxy)pyridin-2-yl)-1-(6-formyl-5-((4-methyl-2-oxopiperazin-1-yl)methyl)pyridin-2-yl)-1-methylurea | 470 |

-continued

| Example No. | Compound structure | Compound name | MS: m/z [M + 1]+ |
|---|---|---|---|
| 39 | 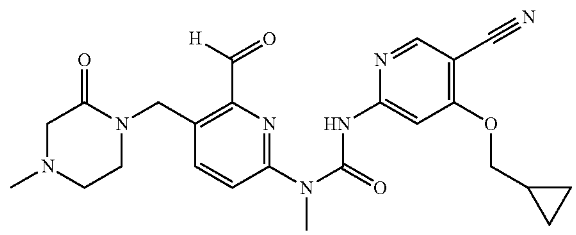 [SMILES: CN1CCN(Cc2ccc(N(C)C(=O)Nc3cc(OCC4CC4)c(C#N)cn3)nc2C=O)C(=O)C1] | 3-(5-cyano-4-(cyclopropylmethoxy)pyridin-2-yl)-1-(6-formyl-5-((4-methyl-2-oxopiperazin-1-yl)methyl)pyridin-2-yl)-1-methylurea | 478 |
| 40 | 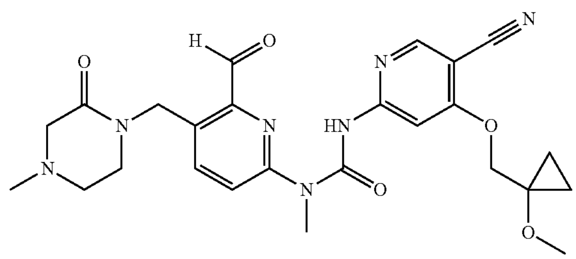 [SMILES: COC1(COc2cc(NC(=O)N(C)c3ccc(CN4CCN(C)CC4=O)c(C=O)n3)ncc2C#N)CC1] | 3-(5-cyano-4-((1-methoxycyclopropyl)methoxy)pyridin-2-yl)-1-(6-formyl-5-((4-methyl-2-oxopiperazin-1-yl)methyl)pyridin-2-yl)-1-methylurea | 508 |
| 41 | 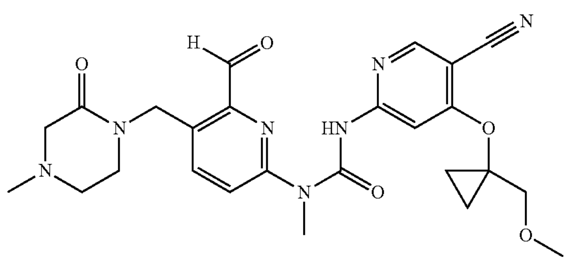 | 3-(5-cyano-4-(1-(methoxymethyl)cyclopropoxy)pyridin-2-yl)-1-(6-formyl-5-((4-methyl-2-oxopiperazin-1-yl)methyl)pyridin-2-yl)-1-methylurea | 508 |
| 42 | 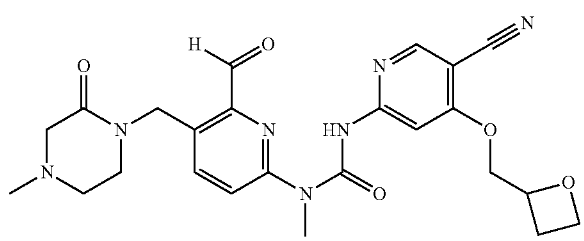 [SMILES: CN1CCN(Cc2ccc(N(C)C(=O)Nc3cc(OCC4CCO4)c(C#N)cn3)nc2C=O)C(=O)C1] | 3-(5-cyano-4-(oxetan-2-ylmethoxy)pyridin-2-yl)-1-(6-formyl-5-((4-methyl-2-oxopiperazin-1-yl)methyl)pyridin-2-yl)-1-methylurea | 494 |
| 43 | 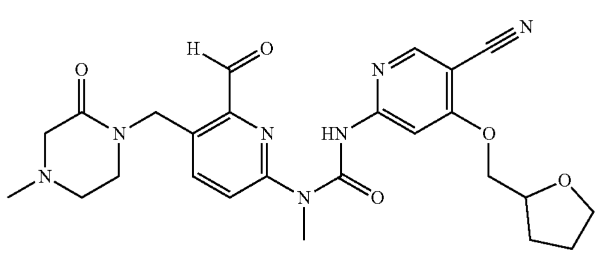 [SMILES: CN1CCN(Cc2ccc(N(C)C(=O)Nc3cc(OCC4CCCO4)c(C#N)cn3)nc2C=O)C(=O)C1] | 3-(5-cyano-4-((tetrahydrofuran-2-yl)methoxy)pyridin-2-yl)-1-(6-formyl-5-((4-methyl-2-oxopiperazin-1-yl)methyl)pyridin-2-yl)-1-methylurea | 508 |
| 44 | 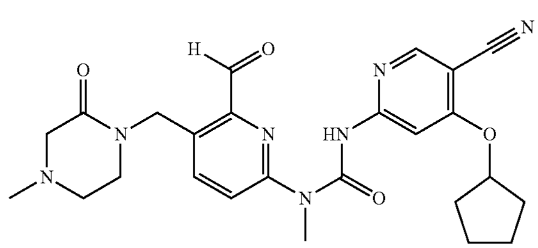 [SMILES: CN1CCN(Cc2ccc(N(C)C(=O)Nc3cc(OC4CCCC4)c(C#N)cn3)nc2C=O)C(=O)C1] | 3-(5-cyano-4-(cyclopentyloxy)pyridin-2-yl)-1-(6-formyl-5-((4-methyl-2-oxopiperazin-1-yl)methyl)pyridin-2-yl)-1-methylurea | 492 |

-continued

| Example No. | Compound structure | Compound name | MS: m/z [M + 1]+ |
|---|---|---|---|
| 45 | 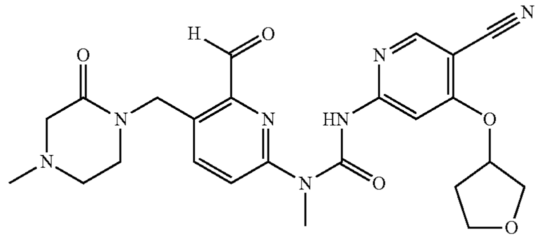 [SMILES: CN1CCN(Cc2ccc(N(C)C(=O)Nc3cc(OC4CCOC4)c(C#N)cn3)nc2C=O)C(=O)C1] | 3-(5-cyano-4-((tetrahydrofuran-3-yl)oxy) pyridin-2-yl)-1-(6-formyl-5-((4-methyl-2-oxopiperazin-1-yl)methyl)pyridin-2-yl)-1-methylurea | 494 |
| 46 | 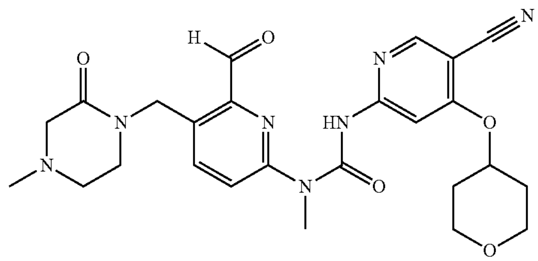 [SMILES: CN1CCN(Cc2ccc(N(C)C(=O)Nc3cc(OC4CCOCC4)c(C#N)cn3)nc2C=O)C(=O)C1] | 3-(5-cyano-4-((tetrahydro-2H-pyran-4-yl) oxy)pyridin-2-yl)-1-(6-formyl-5-((4-methyl-2-oxopiperazin-1-yl)methyl) pyridin-2-yl)-1-methylurea | 508 |
| 47 | 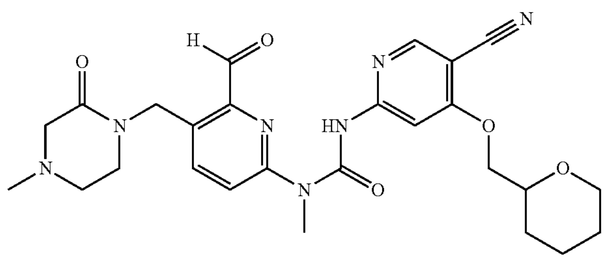 [SMILES: CN1CCN(Cc2ccc(N(C)C(=O)Nc3cc(OCC4CCCCO4)c(C#N)cn3)nc2C=O)C(=O)C1] | 3-(5-cyano-4-((tetrahydro-2H-pyran-2-yl) methoxy)pyridin-2-yl)-1-(6-formyl-5-((4-methyl-2-oxopiperazin-1-yl)methyl) pyridin-2-yl)-1-methylurea | 522 |
| 48 | 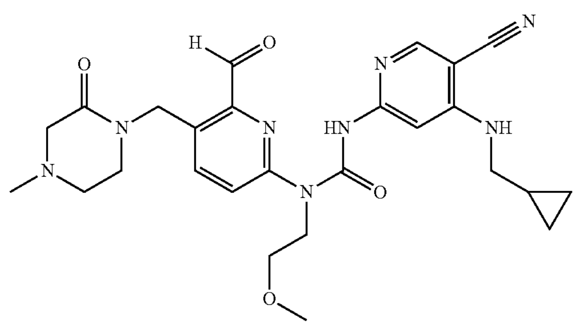 [SMILES: COCCN(C(=O)Nc1cc(NCC2CC2)c(C#N)cn1)c1ccc(CN2CCN(C)CC2=O)c(C=O)n1] | 3-(5-cyano-4-((cyclopropylmethyl)amino) pyridin-2-yl)-1-(6-formyl-5-((4-methyl-2-oxopiperazin-1-yl)methyl)pyridin-2-yl)-1-(2-methoxyethyl)urea | 521 |
| 49 | 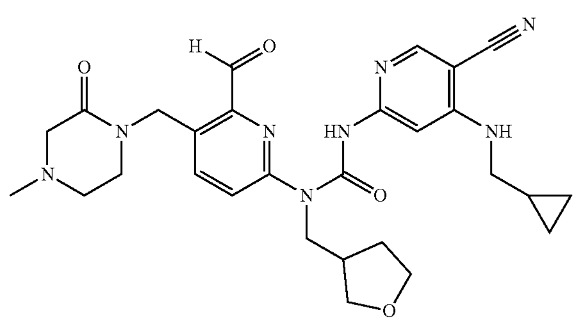 [SMILES: CN1CCN(Cc2ccc(N(CC3CCOC3)C(=O)Nc3cc(NCC4CC4)c(C#N)cn3)nc2C=O)C(=O)C1] | 3-(5-cyano-4-((cyclopropylmethyl)amino) pyridin-2-yl)-1-(6-formyl-5-((4-methyl-2-oxopiperazin-1-yl)methyl)pyridin-2-yl)-1-((tetrahydrofuran-3-yl)methyl)urea | 547 |

| Example No. | Compound structure | Compound name | MS: m/z [M + 1]+ |
|---|---|---|---|
| 50 | 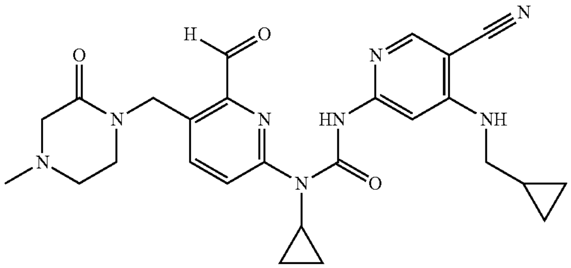 [SMILES: CN1CCN(Cc2ccc(N(C(=O)Nc3cc(NCC4CC4)c(C#N)cn3)C3CC3)nc2C=O)C(=O)C1] | 3-(5-cyano-4-((cyclopropylmethyl)amino) pyridin-2-yl)-1-cyclopropyl-1-(6-formyl-5-((4-methyl-2-oxopiperazin-1-yl) methyl)pyridin-2-yl)urea | 503 |
| 51 | 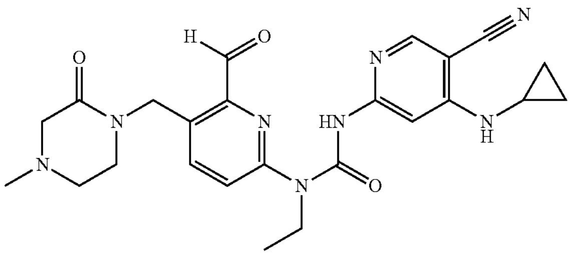 [SMILES: CCN(C(=O)Nc1cc(NC2CC2)c(C#N)cn1)c1ccc(CN2CCN(C)CC2=O)c(C=O)n1] | 3-(5-cyano-4-(cyclopropylamino)pyridin-2-yl)-1-ethyl-1-(6-formyl-5-((4-methyl-2-oxopiperazin-1-yl)methyl)pyridin-2-yl)urea | 477 |

Example 52: Preparation of N-(5-cyano-4-(cyclopropylamino)pyridin-2-yl)-1-(6-formylpyridin-2-yl) cyclopropane-1-carboxamide

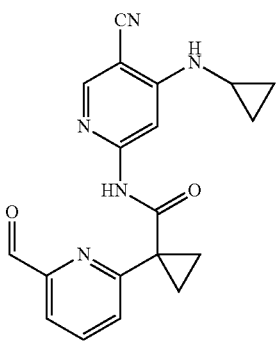 [SMILES: N#Cc1cnc(NC(=O)C2(c3cccc(C=O)n3)CC2)cc1NC1CC1]

Step 1: Synthesis of 1-(6-(1,3-dioxolan-2-yl)pyridin-2-yl)cyclopropane-1-carboxamide

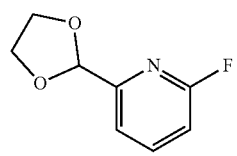

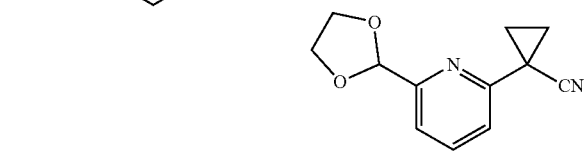

Cyclopropanecarbonitrile (800 mg, 11.9 mmol) was dissolved in tetrahydrofuran (50 m L), and then a solution of potassium bis (trimethylsilyl) amide in atetrahydrofuran (14.3 m L, 14.3 mmol) was added at room temperature. The mixture solution was stirred for 20 minutes, then 2-(1,3-dioxolan-2-yl)-6-fluoropyridin (4.02 g, 23.8 mmol) was added. The mixture was stirred for 16 hours at 70° C. The reaction solution was concentrated and then separated by column chromatographyseparation [eluent: PE~PE/EtOAc (3:1)] to obtain 1-(6-(1,3-dioxolan-2-yl)pyridin-2-yl)cyclopropane-1-carboxamide (450 mg, yield 18%). MS m/z (E S): 217.2 [M+H]+.

Step 2: Synthesis of 1-(6-1,3-dioxolan-2-yl)pyridin-2-yl)cyclopropane-1-carboxamide

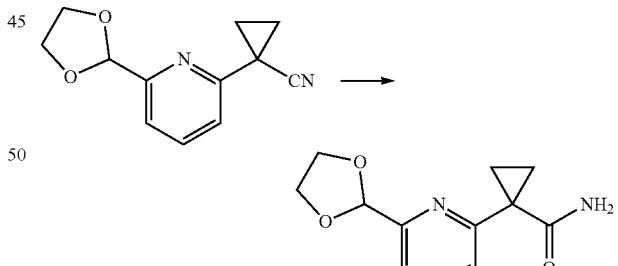

1-(6-(1,3-dioxolan-2-yl)pyridin-2-yl)cyclopropane-1-carbonitrile (450 mg, 2.08 mmol) was dissolved in a mixed solution of methanol and water (50 mL), and sodium hydroxide (333 mg, 8.33 mmol) was added at room temperature. The mixture was stirred for 16 hours under reflux, and then the reaction solution was concentrated and separated by column chromatography [eluent: CH$_2$Cl$_2$~CH$_2$Cl$_2$/MeOH (10:1)] to obtain 1-(6-(1,3-dioxolan-2-yl)pyri din-2-yl) cyclopropane-1-carboxamide (70 mg, yield: 14%). MS m/z (ESI): 235.2 [M+H]+.

Step 3: Synthesis of 1-(6-(1,3-dioxolan-2-yl) pyridin-2-yl)-N-(5-cyano-4-(cyclopropylamino) pyridin-2-yl)cyclopropane-1-carboxamide Step 4: Synthesis of N-(5-cyano-4-(cyclopropylamino) pyridin-2-yl)-1-(6-formyl pyridin-2-yl) cyclopropane-1-carboxamide

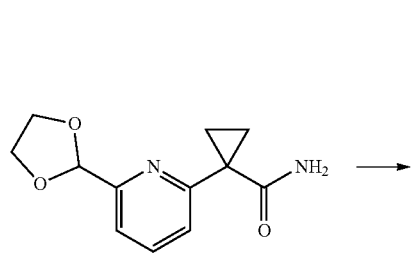

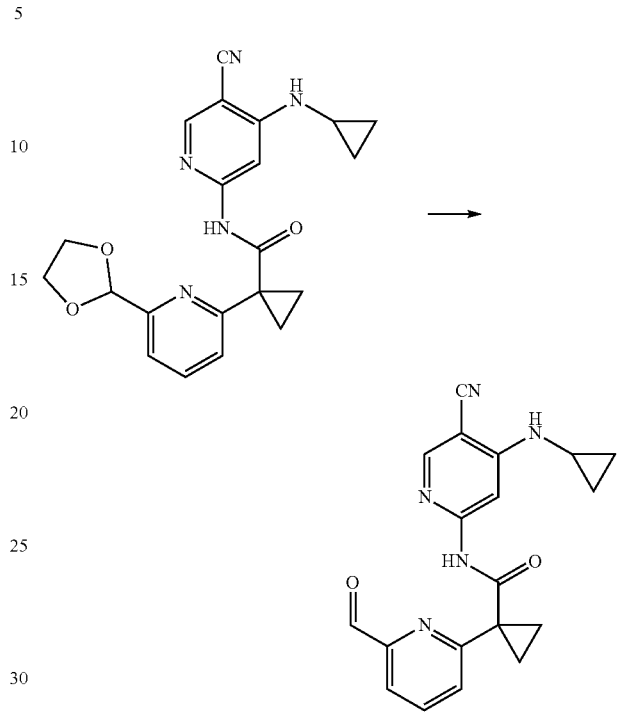

1-(6-(1,3-dioxolan-2-yl)pyridin-2-yl)cyclopropane-1-carboxamide (70 mg, 0.29 mmol), 6-chlorine-4-(cyclopropylamino)nicotinonitrile (69.2 mg, 0.36 mmol), tris (dibenzylideneacetone) dipalladium (27.2 mg, 0.03 mmol), and 4,5-bis(diphenylphosphino)-9,9-dimethylxanthene (17.3 mg, 0.03 mmol) were dissolved in a solution of cesium carbonate (193 mg, 0.59 mmol) in methanol (30 mL). The mixture was heated to 130° C. by microwave under stirring for 2 hours. The reaction solution was concentrated and then separated by column chromatography [eluent: CH$_2$Cl$_2$~CH$_2$Cl$_2$/MeOH (10:1)] to obtain 1-(6-(1,3-dioxolan-2-yl)pyridin-2-yl)-N-(5-cyano-4-(cyclopropylamino) pyridin-2-yl)cyclopropane-1-carboxamide (100 mg, yield: 14%). MS m/z (ESI): 392.0 [M+H]$^+$.

1-(6-(1,3-dioxolan-2-yl)pyridin-2-yl)-N-(5-cyano-4-(cyclopropylamino)pyridin-2-yl)cyclopropane-1-carboxamide (100 mg, 0.25 mmol) was dissolved in a mixture solution (11 mL) of tetrahydrofuran and water (10:1), and concentrated hydrochloric acid (0.3 mL) was added. The mixture was stirred for 4 hours; the reaction solution was washed with a saturated sodium bicarbonate solution (4 mL), and then extracted with dichloromethane (20 mL*3). The organic phase was combined, dried over sodium sulfate, concentrated, and then subjected to TLC separation [eluent: CH$_2$Cl$_2$~CH$_2$Cl$_2$/MeOH (10:1)] to obtain N-(5-cyano-4-(cyclopropylamino)pyridin-2-yl)-1-(6-formylpyridin-2-yl) cyclopropane-1-carboxamide (3 mg, yield: 3%). MS m/z (ESI): 348.3 [M+H]$^+$.

$^1$H NMR (400 MHz, CDCl$_3$): δ (11.21 (s, 1H), 10.19 (s, 1H), 8.11 (s, 1H), 8.07 (s, 1H), 7.92-7.90 (m, 2H), 7.47-7.45 (m, 11H), 3.58-3.50 (m, 1H), 2.65-2.63 (m, 1H), 2.00-1.97 (m, 2H), 1.50-1.47 (m, 2H), 1.03-0.98 (m, 2H), 0.71-0.68 (m, 2H).

Examples 53-55 were prepared according to the synthesis method of Example 52:

| Example No. | Compound structure | Compound name | MS: m/z [M + 1]$^+$ |
|---|---|---|---|
| 53 | 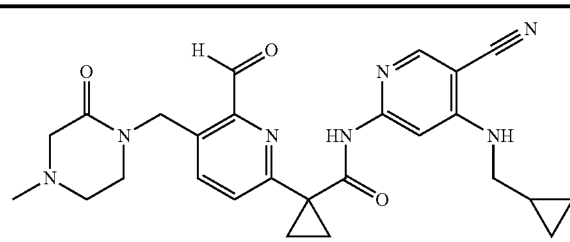 | N-(5-cyano-4-((cyclopropylmethyl)amino)pyridin-2-yl)-1-(6-formyl-5-((4-methyl-2-oxopiperazin-1-yl)methyl)pyridin-2-yl)cyclopropane-1-carboxamide | 488 |

| Example No. | Compound structure | Compound name | MS: m/z [M + 1]+ |
|---|---|---|---|
| 54 | 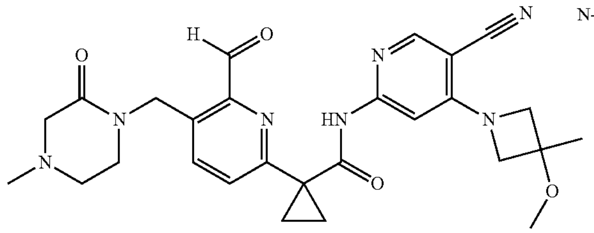 | N-(5-cyano-4-(3-methoxy-3-methylazetidin-1-yl)pyridin-2-yl)-1-(6-formyl-5-((4-methyl-2-oxopiperazin-1-yl)methyl)pyridin-2-yl)cyclopropane-1-carboxamide | 518 |
| 55 | 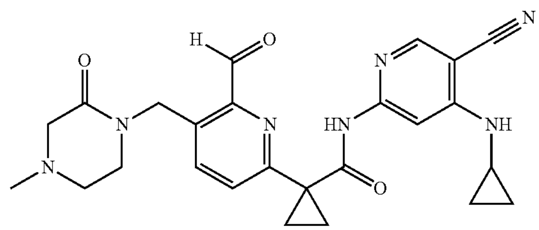 [SMILES: CN1CCN(Cc2ccc(C3(C(=O)Nc4cc(NC5CC5)c(C#N)cn4)CC3)nc2C=O)C(=O)C1] | N-(5-cyano-4-(cyclopropylamino)pyridin-2-yl)-1-(6-formyl-5-((4-methyl-2-oxopiperazin-1-yl)methyl)pyridin-2-yl)cyclopropane-1-carboxamide | 474 |

Example 56: Preparation of 3-(4-(cyclopropylamino)-5-iodopyridin-2-yl)-1-(6-formyl-5-((4-methyl-2-oxopiperazin-1-yl)methyl) pyridin-2-yl)-1-methylurea

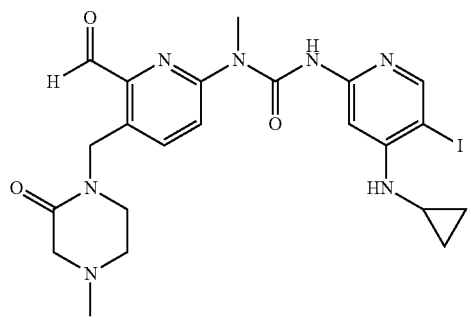 [SMILES: CN1CCN(Cc2ccc(N(C)C(=O)Nc3cc(NC4CC4)c(I)cn3)nc2C=O)C(=O)C1]

Step 1: Synthesis of N²-bis (phenoxyoxo)-N⁴-cyclopropyl-5-iodopyridin-2,4-diamine

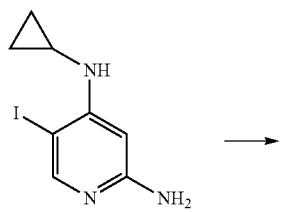

→

-continued

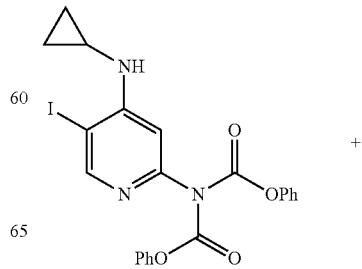

$N^4$-cyclopropyl-5-iodopyridin-2,4-diamine (200 mg, 0.73 mmol) was dissolved in aceton itrilesolution (15 mL), DIPEA (282 mg, 2.19 mmol) and phenyl chloroformate (240 mg, 1.53 mmol) were added under an iced bath, and the mixture was stirred for 2 hours at 0° C. The reaction solution was concentrated, then separated by column chromatography [eluent: $CH_2Cl_2$~$CH_2Cl_2$/MeOH (20:1)] to obtain $N^2$-bis (phenoxyoxo) —$N^4$-cyclopropyl-5-iodopyridin-2,4-diamine (200 mg, yield: 53%). MS m/z (ESI): 516.2 [M+H]+.

Step 2: Synthesis of 1-(6-(1,3-dioxolan-2-yl)-5-((4-methyl-2-oxopiperazin-1-yl)methyl) pyridin-2-yl)-3-(4-(cyclopropylamino)-5-iodopyridin-2-yl)-1-methylurea

+

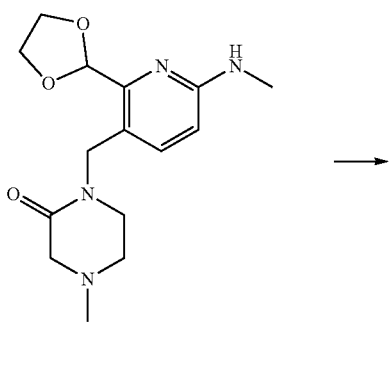

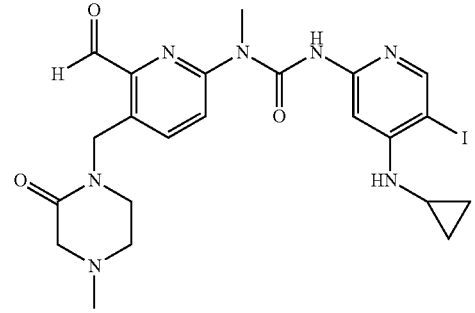

1-(6-(1,3-dioxolan-2-yl)-5-((4-methyl-2-oxopiperazin-1-yl)methyl)pyridin-2-yl)-3-(4-(cyclopropylamino)-5-iodopyridin-2-yl)-1-methylurea (11 mg, 0.02 mmol) was dissolved in a mixture solvent (3 mL) of tetrahydrofuran and water, then 1 drop of concentrated hydrochloric acid was added. The mixture was reacted for 0.5 hour at room temperature, and then sodium bicarbonate was added to adjust the pH to weak alkaline, and then ethyl acetate and water were added. The organic phase was successively washed with water and a saturated salt solution, dried over sodium sulfate, concentrated and separated by PTLC [eluent: $CH_2Cl_2$~$CH_2Cl_2$/MeOH (12:1)] to obtain 3-(4-(cyclopropylamino)-5-iodopyridin-2-yl)-1-(6-formyl-5-((4-methyl-2-oxopiperazin-1-yl)methyl)pyridin-2-yl)-1-methylurea (4 mg, yield: 39%). MS m/z (ESI): 564.2 [M+H]+.

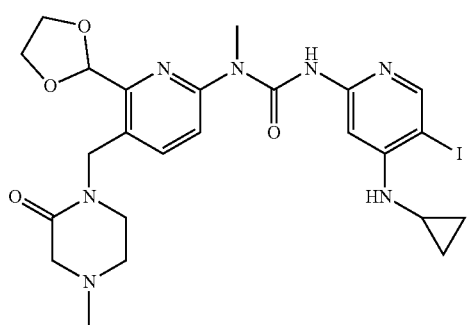

$N^2$-bis(phenoxyoxo)-$N^4$-cyclopropyl-5-iodopyridin-2,4-diamine (50 mg, 0.10 mmol), 1-((2-(1,3-dioxolan-2-yl)-6-(methyl amino)pyridin-3-yl)methyl)-4-methylpiperazin-2-one (30 mg, 0.10 mmol) were dissolved in toluene (4 mL), and the mixture was heated to 120° C. by microwave and stirred for 3 hours. The reaction solution was concentrated, and then separated by column chromatography [eluent: $CH_2C_2$~$CH_2Cl_2$/MeOH (15:1)] to obtain 1-(6-(1,3-dioxolan-2-yl)-5-((4-methyl-2-oxopiperazin-1-yl)methyl)pyridin-2-yl)-3-(4-(cyclopropylamino)-5-iodopyridin-2-yl)-1-methylurea (11 mg, yield: 18%). MS m/z (ESI): 608.2 [M+H]+.

¹H NMR (400 MHz, CDCl₃) δ 12.50 (s, 1H), 10.19 (s, 1H), 8.11 (s, 1H), 7.83 (d, J=8.7 Hz, 1H), 7.79 (s, 1H), 7.21 (d, J=8.5 Hz, 1H), 5.03 (s, 2H), 4.94 (s, 11H), 3.45 (s, 3H), 3.29 (t, J=5.5 Hz, 2H), 3.13 (s, 2H), 2.60 (t, J=5.5 Hz, 2H), 2.54 (s, 1H), 2.29 (s, 3H), 0.87 (d, J=5.5 Hz, 2H), 0.59-0.55 (m, 2H).

Step 3: Synthesis of 3-(4-(cyclopropylamino)-5-iodopyridin-2-yl)-1-(6-formyl-5-((4-methyl-2-oxopiperazin-1-yl) methyl) pyridin-2-yl)-1-methylurea Example 57: Preparation of 3-(4-(cyclopropylamino)-5-(cyclopropylethynyl) pyridin-2-yl)-1-(6-formyl-5-((4-methyl-2-oxopiperazin-1-yl)methyl) pyridin-2-yl)-1-methylurea

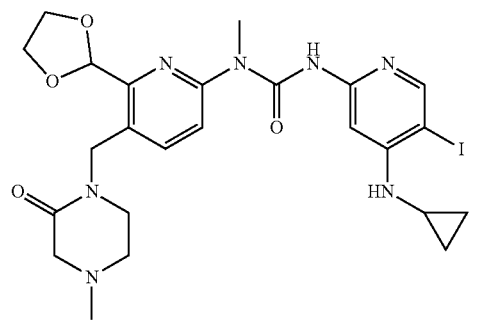

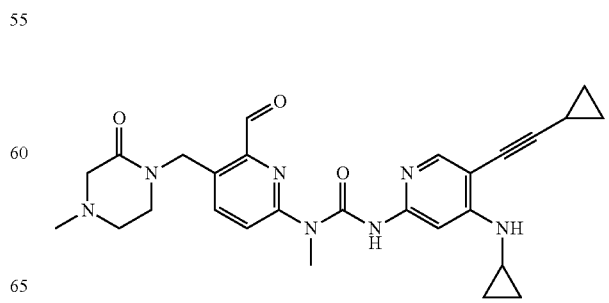

Step 1: Synthesis of 3-(4-(cyclopropylamino)-5-(cyclopropylethynyl)pyridin-2-yl)-1-(6-(dimethoxymethyl)-5-((4-methyl-2-oxopiperazin-1-ylmethyl)pyridin-2-yl)-1-methylurea

Step 2: Synthesis of 3-(4-(cyclopropylamino)-5-(cyclopropylethynyl)pyridin-2-yl)-1-(6-formyl-5-((4-methyl-2-oxopiperazin-1-yl)methyl)pyridin-2-yl)-1-methylurea

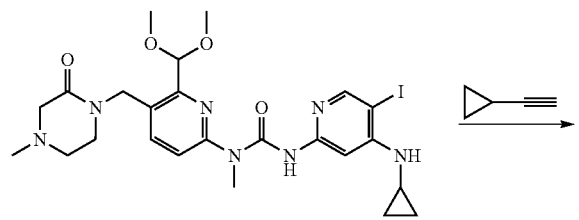

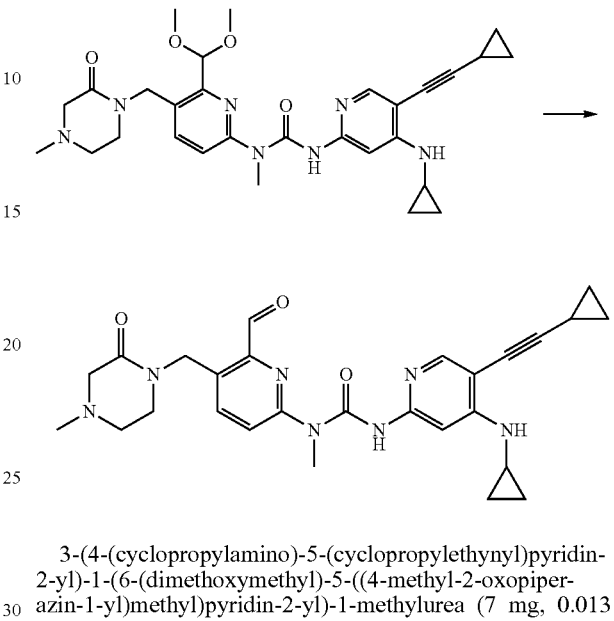

3-(4-(cyclopropylamino)-5-iodopyridin-2-yl)-1-(6-(dimethoxymethyl)-5-((4-methyl-2-oxopiperazin-1-yl)methyl)pyridin-2-yl)-1-methylurea (300 mg, 0.49 mmol), cyclopropyl acetylene (162 mg, 2.45 nmol), CuI (19 mg, 0.01 mmol), Pd(PPh$_3$)$_2$Cl$_2$ (7 mg, 0.01 mmol), and triethylamine (148 mg, 1.47 mmol) were dissolved in tetrahydrofuran (50 mL), and the mixture was heated to 80° C. under a nitrogen atmosphere and reacted for 4 hours. Then the reaction solution was added with ethyl acetate, filtered, and separated by silica gel column chromatography [DCM/MeOH] to obtain 3-(4-(cyclopropylamino)-5-(cyclopropylethynyl)pyridin-2-yl)-1-(6-(dimethoxymethyl)-5-((4-methyl-2-oxopiperazin-1-yl)methyl)pyridin-2-yl)-1-methylurea (152 mg, yield: 56%). MS m/z (ESI): 548 [M+H]$^+$.

3-(4-(cyclopropylamino)-5-(cyclopropylethynyl)pyridin-2-yl)-1-(6-(dimethoxymethyl)-5-((4-methyl-2-oxopiperazin-1-yl)methyl)pyridin-2-yl)-1-methylurea (7 mg, 0.013 mmol) was dissolved in a buffered solution of tetrahydrofuran (10 mL) and water (1 mL), then 2 drops of concentrated hydrochloric acid was added. The mixture was reacted with the monitoring of LCMS; when the reaction was completed, a saturated sodium bicarbonate aqueous solution was added to quench the reaction under an iced bath. The reaction solution was extracted with dichloromethane, dried over sodium sulfate, filtered, concentrated, and then separated by PTLC to obtain 3-(4-(cyclopropylamino)-5-(cyclopropylethynyl)pyridin-2-yl)-1-(6-formyl-5-((4-methyl-2-oxopiperazin-1-yl)methyl)pyridin-2-yl)-1-methylurea (3 mg, yield: 47%). MS m/z (ESI): 502 [M+H]+.

1H NMR (400 MHz, CDCl$_3$) δ 12.22 (s, 1H), 10.19 (s, 1H), 7.83 (s, 1H), 7.82 (d, J=9.0 Hz, 1H), 7.75 (s, 1H), 7.25 (d, J=8.6 Hz, 1H), 5.34 (s, 1H), 5.04 (s, 2H), 3.47 (s, 3H), 3.29 (t, J=5.6 Hz, 2H), 3.13 (s, 2H), 2.59 (t, J=5.5 Hz, 2H), 2.57-2.51 (m, 1H), 2.28 (s, 3H), 1.44-1.41 (m, 1H), 0.85-0.75 (m, 8H).

Examples 58-74 were prepared according to the synthesis method of Example 57:

| Example No. | Compound structure | Compound name | MS: m/z [M + 1]$^+$ |
|---|---|---|---|
| 58 | 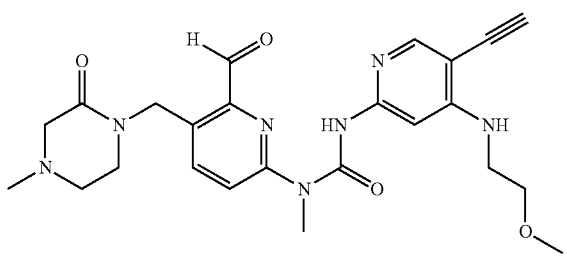 | 3-(5-ethynyl-4-((2-methoxyethyl)amino)pyridin-2-yl)-1-(6-formyl-5-((4-methyl-2-oxopiperazin-1-yl)methyl)pyridin-2-yl)-1-methylurea | 480 |

-continued

| Example No. | Compound structure | Compound name | MS: m/z [M + 1]+ |
|---|---|---|---|
| 59 | 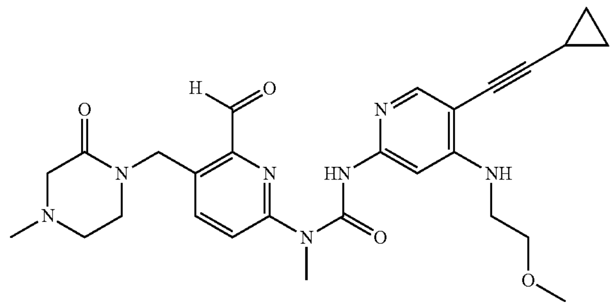 [SMILES: COCCNc1cc(NC(=O)N(C)c2ccc(CN3CCN(C)CC3=O)c(C=O)n2)ncc1C#CC1CC1] | 3-(5-(cyclopropylethynyl)-4-((2-methoxyethyl)amino)pyridin-2-yl)-1-(6-formyl-5-((4-methyl-2-oxopiperazin-1-yl)methyl)pyridin-2-yl)-1-methylurea | 520 |
| 60 | 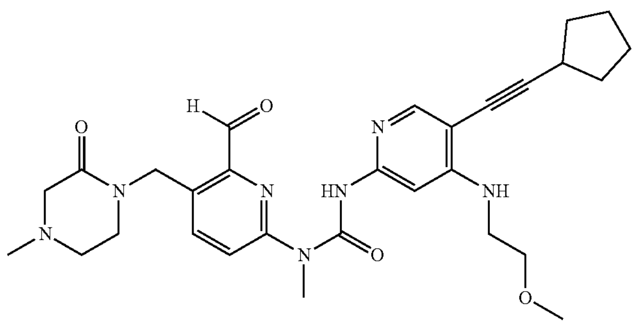 [SMILES: COCCNc1cc(NC(=O)N(C)c2ccc(CN3CCN(C)CC3=O)c(C=O)n2)ncc1C#CC1CCCC1] | 3-(5-(cyclopentylethynyl)-4-((2-methoxyethyl)amino)pyridin-2-yl)-1-(6-formyl-5-((4-methyl-2-oxopiperazin-1-yl)methyl)pyridin-2-yl)-1-methylurea | 548 |
| 61 | 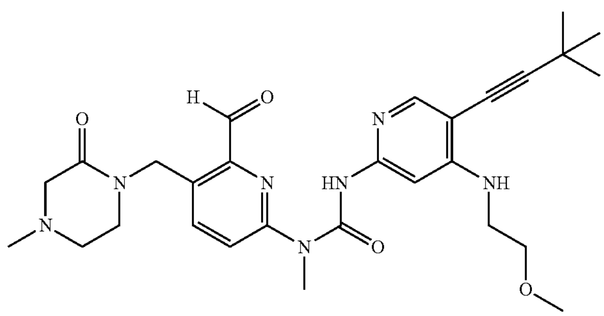 [SMILES: COCCNc1cc(NC(=O)N(C)c2ccc(CN3CCN(C)CC3=O)c(C=O)n2)ncc1C#CC(C)(C)C] | 3-(5-(3,3-dimethylbut-1-yn-1-yl)-4-((2-methoxyethyl)amino)pyridin-2-yl)-1-(6-formyl-5-((4-methyl-2-oxopiperazin-1-yl)methyl)pyridin-2-yl)-1-methylurea | 536 |
| 62 | 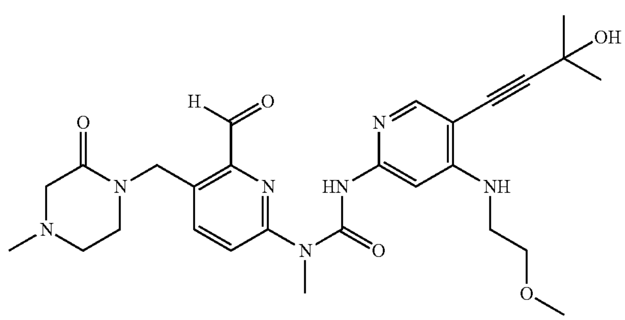 [SMILES: COCCNc1cc(NC(=O)N(C)c2ccc(CN3CCN(C)CC3=O)c(C=O)n2)ncc1C#CC(C)(C)O] | 1-(6-formyl-5-((4-methyl-2-oxopiperazin-1-yl)methyl)pyridin-2-yl)-3-(5-(3-hydroxy-3-methylbut-1-yn-1-yl)-4-((2-methoxyethyl)amino)pyridin-2-yl)-1-methylurea | 538 |
| 63 | 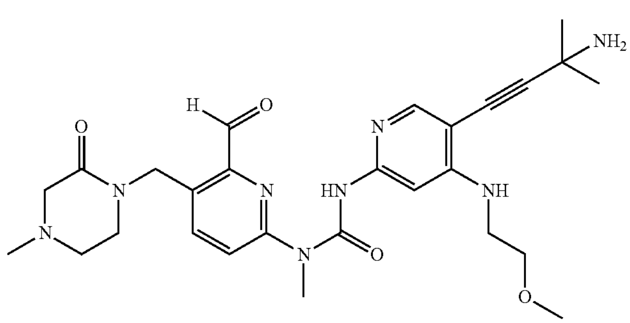 [SMILES: COCCNc1cc(NC(=O)N(C)c2ccc(CN3CCN(C)CC3=O)c(C=O)n2)ncc1C#CC(C)(C)N] | 3-(5-(3-amino-3-methylbut-1-yn-1-yl)-4-((2-methoxyethyl)amino)pyridin-2-yl)-1-(6-formyl-5-((4-methyl-2-oxopiperazin-1-yl)methyl)pyridin-2-yl)-1-methylurea | 537 |

-continued

| Example No. | Compound structure | Compound name | MS: m/z [M + 1]+ |
|---|---|---|---|
| 64 | 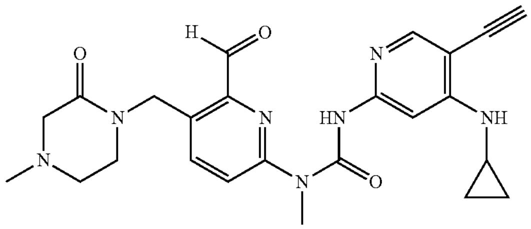 [SMILES: C#Cc1cnc(NC(=O)N(C)c2ccc(CN3CCN(C)CC3=O)c(C=O)n2)cc1NC1CC1] | 3-(4-(cyclopropylamino)-5-ethynylpyridin-2-yl)-1-(6-formyl-5-((4-methyl-2-oxopiperazin-1-yl)methyl)pyridin-2-yl)-1-methylurea | 462 |
| 65 | 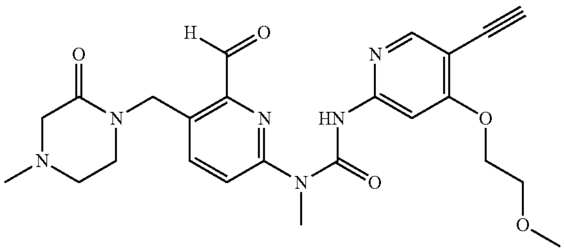 | 3-(5-ethynyl-4-(2-methoxyethoxy)pyridin-2-yl)-1-(6-formyl-5-((4-methyl-2-oxopiperazin-1-yl)methyl)pyridin-2-yl)-1-methylurea | 481 |
| 66 | 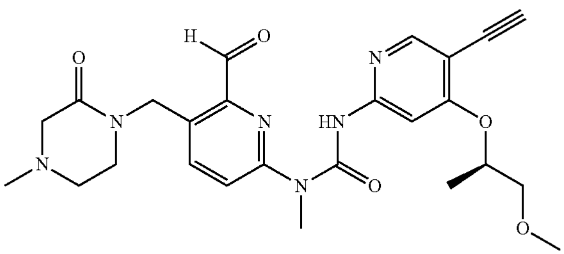 | (R)-3-(5-ethynyl-4-((1-methoxypropan-2-yl)oxy)pyridin-2-yl)-1-(6-formyl-5-((4-methyl-2-oxopiperazin-1-yl)methyl)pyridin-2-yl)-1-methylurea | 495 |
| 67 | 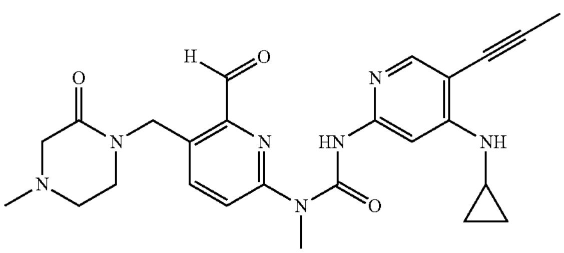 [SMILES: CC#Cc1cnc(NC(=O)N(C)c2ccc(CN3CCN(C)CC3=O)c(C=O)n2)cc1NC1CC1] | 3-(4-(cyclopropylamino)-5-(prop-1-yn-1-yl)pyridin-2-yl)-1-(6-formyl-5-((4-methyl-2-oxopiperazin-1-yl)methyl)pyridin-2-yl)-1-methylurea | 476 |
| 68 | 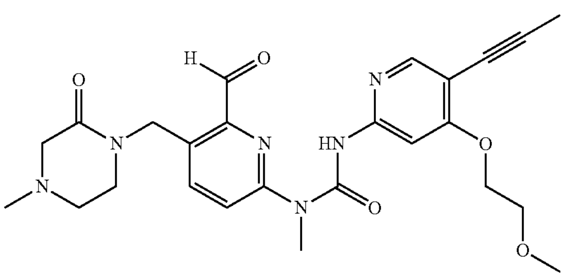 [SMILES: CC#Cc1cnc(NC(=O)N(C)c2ccc(CN3CCN(C)CC3=O)c(C=O)n2)cc1OCCOC] | 1-(6-formyl-5-((4-methyl-2-oxopiperazin-1-yl)methyl)pyridin-2-yl)-3-(4-(2-methoxyethoxy)-5-(prop-1-yn-1-yl)pyridln-2-yl)-1-methylurea | 495 |
| 69 | 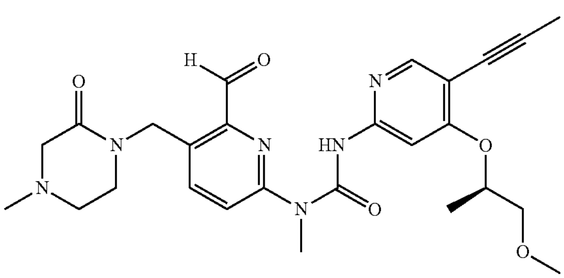 [SMILES: CC#Cc1cnc(NC(=O)N(C)c2ccc(CN3CCN(C)CC3=O)c(C=O)n2)cc1O[C@H](C)COC] | (R)-1-(6-formyl-5-((4-methyl-2-oxopiperazin-1-yl)methyl)pyridin-2-yl)-3-(4-((1-methoxypropan-2-yl)oxy)-5-(prop-1-yn-1-yl)pyridin-2-yl)-1-methylurea | 509 |

-continued

| Example No. | Compound structure | Compound name | MS: m/z [M + 1]+ |
|---|---|---|---|
| 70 | 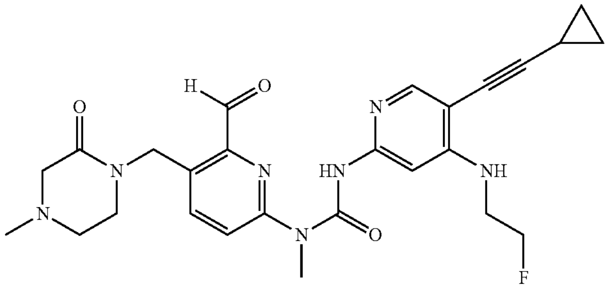 [SMILES: CN1CCN(Cc2ccc(N(C)C(=O)Nc3cc(NCCF)c(C#CC4CC4)cn3)nc2C=O)C(=O)C1] | 3-(5-(cyclopropylethynyl)-4-((2-fluoroethyl) amino)pyridin-2-yl)-1-(6-formyl-5-((4-methyl-2-oxopiperazin-1-yl)methyl) pyridin-2-yl)-1-methylurea | 508 |
| 71 | 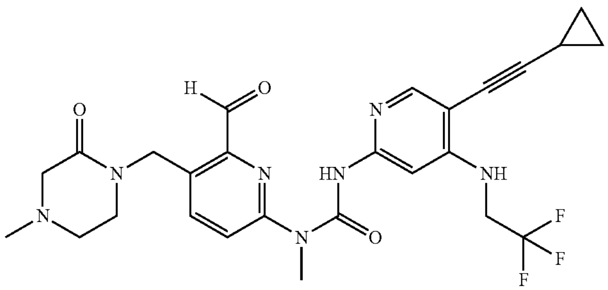 [SMILES: CN1CCN(Cc2ccc(N(C)C(=O)Nc3cc(NCC(F)(F)F)c(C#CC4CC4)cn3)nc2C=O)C(=O)C1] | 3-(5-(cyclopropylethynyl)-4-((2,2,2-trifluoroethyl)amino)pyridin-2-yl)-1-(6-formyl-5-((4-methyl-2-oxopiperazin-1-yl)methyl) pyridin-2-yl)-1-methylurea | 544 |
| 72 | 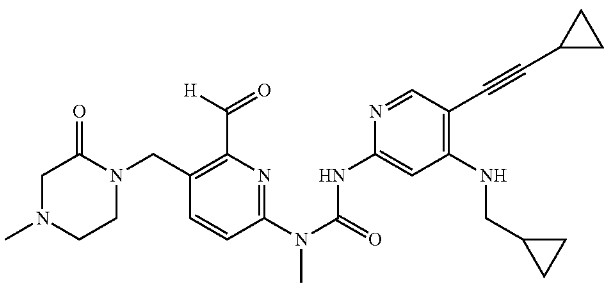 [SMILES: CN1CCN(Cc2ccc(N(C)C(=O)Nc3cc(NCC4CC4)c(C#CC4CC4)cn3)nc2C=O)C(=O)C1] | 3-(5-(cyclopropylethynyl)-4-((cyclopropylmethyl)amino)pyridin-2-yl)-1-(6-formyl-5-((4-methyl-2-oxopiperazin-1-yl)methyl) pyridin-2-yl)-1-methylurea | 516 |
| 73 | 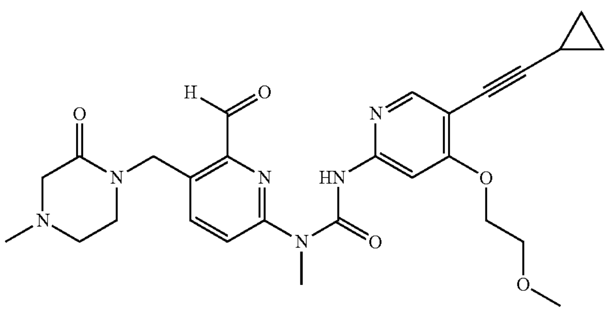 [SMILES: COCCOc1cc(NC(=O)N(C)c2ccc(CN3CCN(C)CC3=O)c(C=O)n2)ncc1C#CC1CC1] | 3-(5-(cyclopropylethynyl)-4-(2-methoxyethoxy) pyridin-2-yl)-1-(6-formyl-5-((4-methyl-2-oxopiperazin-1-yl)methyl)pyridin-2-yl)-1-methylurea | 532 |
| 74 | 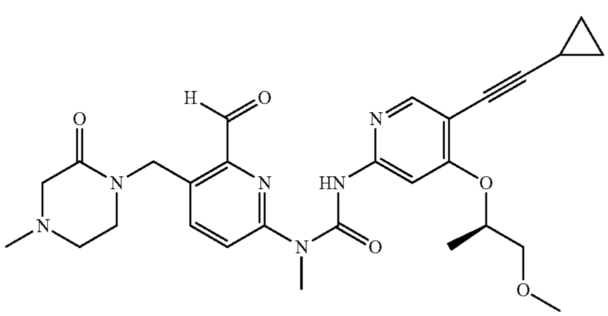 [SMILES: COC[C@@H](C)Oc1cc(NC(=O)N(C)c2ccc(CN3CCN(C)CC3=O)c(C=O)n2)ncc1C#CC1CC1] | (R)-3-(5-(cyclopropylethynyl)-4-((1-methoxypropan-2-yl)oxy)pyridin-2-yl)-1-(6-formyl-5-((4-methyl-2-oxopiperazin-1-yl) methyl)pyridin-2-yl)-1-methylurea | 560 |

Biological Test and Evaluation

I. In Vitro Biochemical Kinase Analysis of FGFR4

FGFR4 Caliper Assay was used in the present invention to determine the inhibitory activities of the compounds against FGFR4. The specific experimental procedure was as follows:
1. The kinase reaction in the present invention was carried out in a 384-well plate, and 12.5 μM of FGFR4, 65 μM of ATP and 1 μM of peptide (5 Fluo Ahx KKKKEEIYFFFG NH2) were respectively added into the following reaction system.
2. A reaction system is a mixture solution of 50 mM HEPES, pH 7.5, 1 mM DTT, 0.02% Tween 20, 0.02% BSA, 0.6% DMSO, 10 mM beta glycerol phosphate and 10 μM sodium orthovanadate and 16 mM $MgCl_2$.
3. The reaction system was incubated at 30° C. for 40 minutes.
4. The reaction was terminated by adding a stop solution (100 mM HEPES, pH 7.5, 5% DMSO, 0.1% Caliper coating reagent, 10 mM EDTA and 0.015% Brij35).
5. The culture plate with the terminated kinase reaction was transferred to the Caliper LC 3000 workstation to read the data, the phosphorylated and unphosphorylated peptides were separated by using the Caliper microfluid migration shift technique, and the analyte was transferred by allowing a constant buffer flow through the chip, the migration of the substrate peptide was monitored by the labeled fluorescent signal, and the kinase activity was calculated by using the amount of the phosphate-based peptide formed.
6. Finally, $IC_{50}$ values were determined by non-linear regression analysis of percent inhibition at different compound concentrations. The test results for the enzymatic activities of the compounds of the specific examples were shown in Table 1.

II. FGFR4 Cell Proliferation Experiment

Cell Titer Glo (CTG) experiment was used in the present invention to evaluate the functional effects of the compounds on cell proliferation. Huh7 hepatocellular carcinoma cells (Catalog No. TChU182) from the Chinese Academy of Sciences cell bank were cultured in DMEM with high glucose (Gibco, cat. No. 1773536), 10% fetal bovine serum (Gibco, 10099-141) at 37° C., in a 5% $CO_2$ incubator. Compound-mediated inhibition of cell proliferation/survival was assessed by quantification of cellular ATP levels using CTG reagent (Promega, #G7573). The specific experimental procedure was as follows:
1. The cells were seeded into a tissue culture medium-treated 96-well plate (Costar #3904) at 3500 cells/well/ 90 μL of fresh medium;
2. 10 μL of medium containing a compound concentration of 10 fold of its final test concentration was added;
3. The dose effect as evaluated by a 5-fold serial dilution of the test compound, starting from 10 μM.
4. After cells incubation for 3 days at 37° C. in a 5% $CO_2$ atmosphere, the effect of the inhibitor on cell proliferation was quantified after adding 50 μL of CTG and testing with luminescence.
5. The concentration of the compound ($EC_{50}$) leading to half maximal growth inhibition and the concentration of compound (Absolute $IC_{50}$) leading to absolute half growth inhibition were determined using a four-parameter curve fit in Graphpad Prism in a plate reader (M1000, Tecan). The test results of cell activities for the compounds of specific examples were shown in Table 1.

TABLE 1

The results of enzymatic activity and cell activity tests

| Example No. | Enzymatic activity FGFR4 $IC_{50}$ (nM) | Cell activity HuH-7 $EC_{50}$ (nM) | Cell activity HuH-7 Absolute $IC_{50}$ (nM) | $^1$H-NMR(400 MHz) |
|---|---|---|---|---|
| 1 | 2.0 | 8.3 | 26.2 | ($CDCl_3$) δ 13.03 (s, 1H), 10.26 (s, 1H), 8.17 (s, 1H), 7.98 (d, J = 8.7 Hz, 1H), 7.91 (s, 1H), 7.30 (d, J = 8.7 Hz, 1H), 5.30 (d, J = 3.3 Hz, 1H), 5.11 (s, 2H), 3.53 (s, 3H), 3.49(s, 1H), 3.47-3.42(m, 1H), 3.30-3.26(m, 2H), 2.82-2.74 (m, 2H), 2.70-2.51 (m, 1H), 2.43(s, 3H), 0.99-0.94 (m, 2H), 0.69-0.65 (m, 2H). |
| 2 | 8.0 | NT | NT | (DMSO-$d_6$) δ 12.48 (s, 1H), 10.09 (s, 1H), 8.28 (s, 1H), 7.78 (d, J = 8.7 Hz, 1H), 7.64 (d, J = 8.7 Hz, 1H), 7.49 (s, 1H), 7.20 (t, J = 5.1 Hz, 1H), 4.91 (s, 2H), 4.67 (t, J = 5.0 Hz, 1H), 4.55 (t, J = 5.0 Hz, 1H), 3.57 (q, J = 5.4 Hz, 1H), 3.54-3.49 (m, 1H), 3.45 (s, 3H), 3.28 (d, J = 5.6 Hz, 2H), 3.06 (s, 2H), 2.62 (t, J = 5.5 Hz, 2H), 2.24 (s, 3H). |
| 4 | 3.8 | 25.6 | 77.4 | ($CDCl_3$) δ 12.96 (s, 1H), 10.25 (s, 1H), 8.16 (s, 1H), 8.07(s, 1H), 7.52 (s, 1H), 7.33 (d, J = 8.6 Hz, 1H), 5.30 (s, 1H), 5.17-5.05 (m, 2H), 3.52 (s, 3H), 3.47-3.30 (m, 2H), 3.18-3.12 (m, 2H), 3.02-2.87 (m, 2H), 2.58 (s, 3H), 1.47-1.42 (m, 2H), 1.17-1.08 (m, 1H), 0.64 (d, J = 7.5 Hz, 2H), 0.32 (d, J = 5.2 Hz, 2H). |
| 7 | 2.8 | 20.4 | 63.2 | ($CDCl_3$) δ 13.13 (s, 1H), 10.25 (s, 1H), 8.21 (s, 1H), 7.95 (d, J = 8.7 Hz, 1H), 7.48 (s, 1H), 7.28 (s, 1H), 5.11 (d, J = 5.2 Hz, 3H), 4.05 (s, 1H), 3.52 (s, 3H), 3.38 (s, 2H), 3.22 (s, 4H), 2.77-2.52 (m, 4H), 2.38 (s, 3H). |

TABLE 1-continued

The results of enzymatic activity and cell activity tests

| | Enzymatic activity | Cell activity | | |
|---|---|---|---|---|
| Example No. | FGFR4 IC$_{50}$ (nM) | HuH-7 EC$_{50}$ (nM) | HuH-7 Absolute IC$_{50}$ (nM) | $^1$H-NMR(400 MHz) |
| 8 | 5.8 | NT | NT | (CDCl$_3$) δ 13.00 (s, 1H), 10.25 (s, 1H), 8.17 (s, 1H), 7.95 (d, J = 8.8 Hz, 1H), 7.48 (s, 1H), 7.29 (d, J = 8.7 Hz, 1H), 5.10 (s, 2H), 5.06 (d, J = 5.8 Hz, 1H), 3.79-3.68 (m, 2H), 3.52 (s, 3H), 3.40 (s, 2H), 3.27 (s, 3H), 3.23 (s, 2H), 2.99-2.92 (m, 2H), 2.71 (s, 2H), 2.39 (s, 3H), 1.94-1.87 (m, 2H). |
| 11 | 6.9 | 82.2 | 177.4 | (CDCl$_3$) δ 12.94 (s, 1H), 10.25 (s, 1H), 8.15 (s, 1H), 7.93 (d, J = 8.7 Hz, 1H), 7.28 (d, J = 8.7 Hz, 1H), 7.20 (s, 1H), 5.10 (s, 2H), 4.25 (d, J = 8.9 Hz, 2H), 4.11 (d, J = 8.9 Hz, 2H), 3.50 (s, 3H), 3.37 (t, J = 5.5 Hz, 2H), 3.29 (s, 3H), 3.20 (s, 2H), 2.68 (t, J = 5.5 Hz, 2H), 2.36 (s, 3H), 1.56 (s, 3H). |
| 14 | 5.7 | 20.1 | 57.4 | (CDCl$_3$) δ 13.01 (s, 1H), 10.18 (s, 1H), 8.12 (s, 1H), 7.87 (s, 1H), 7.52 (s, 1H), 7.23 (s, 1H), 5.03 (s, 2H), 4.98 (d, J = 6.7 Hz, 1H), 4.24 (s, 1H), 3.97 (s, 2H), 3.82 (s, 1H), 3.71 (s, 1H), 3.45 (s, 3H), 3.30 (t, J = 5.5 Hz, 2H), 3.13 (s, 2H), 2.60 (t, J = 5.5 Hz, 2H), 2.35 (dt, J = 14.8, 7.3 Hz, 1H), 2.29 (s, 3H), 1.92-1.85 (m, 1H). |
| 15 | 2.3 | 19.3 | 48.6 | (CDCl$_3$) δ 13.08 (s, 1H), 10.25 (s, 1H), 8.19 (s, 1H), 7.93 (d, J = 8.7 Hz, 1H), 7.57 (s, 1H), 7.29 (d. J = 8.7 Hz, 1H), 5.10 (s, 2H), 5.01 (d, J = 6.8 Hz, 1H), 4.26-4.17 (m, 1H), 3.52 (s, 3H), 3.37 (dd, J = 6.3, 4.7 Hz, 2H), 3.20 (s, 2H), 2.73 (dd, J = 14.0, 8.0 Hz, 1H), 2.67 (dd, J = 6.2, 4.7 Hz, 2H), 2.43 (dt, J = 9.6, 4.8 Hz, 1H), 2.36 (s, 3H), 2.24-2.09 (m, 2H), 1.88-1.83 (m, 2H). |
| 17 | 6.5 | 38.1 | 84.9 | (CDCl$_3$) δ 12.91 (s, 1H), 10.26 (s, 1H), 8.20 (s, 1H), 7.95 (d, J = 8.7 Hz, 1H), 7.46 (s, 1H), 7.29 (d, J = 8.7 Hz, 1H), 5.11 (s, 2H), 4.09 (d, J = 2.5 Hz, 1H), 3.80 (d, J = 14.1 Hz, 4H), 3.51 (s, 3H), 3.41 (d, J = 6.1 Hz, 2H), 3.37 (s, 3H), 3.25 (s, 2H), 2.74 (s, 2H), 2.41 (s, 3H), 2.24-2.20 (m, 2H). |
| 21 | 8.0 | 22.7 | 55.4 | (CDCl$_3$) δ 12.99 (s, 1H), 10.25 (s, 1H), 8.16 (s, 1H), 7.95 (d, J = 8.8 Hz, 1H), 7.55 (s, 1H), 7.29 (d, J = 8.8 Hz, 1H), 5.32 (t, J = 8.8 Hz, 1H), 5.11 (s, 2H), 4.18-4.12 (m, 1H), 3.96-3.90 (m, 1H), 3.84-3.78 (m, 1H), 3.51 (s, 3H), 3.50-3.45 (m, 1H), 3.36 (t, J = 8.8 Hz, 2H), 3.26-3.20 (m, 1H), 3.24 (s, 2H), 2.66 (t, J = 5.6 Hz, 2H), 2.40 (s, 3H), 2.15-2.00 (m, 1H), 1.99-1.91 (m, 2H), 1.70-1.63 (m, 1H). |
| 24 | 52.2 | 1079 | 1798 | (CDCl$_3$) δ 13.09 (s, 1H), 10.19 (s, 1H), 8.21 (s, 1H), 7.90 (s, 1H), 7.72 (s, 1H), 7.24 (s, 1H), 5.05 (s, 2H), 3.81 (s, 4H), 3.44 (s, 7H), 3.31 (d, J = 5.7 Hz, 2H), 3.14 (s, 2H), 2.65 (s, 2H), 2.30 (s, 3H). |
| 30 | NT | 76.8 | 206.5 | (CDCl$_3$) δ 12.86 (s, 1H), 10.19 (s, 1H), 8.14 (s, 1H), 7.86 (d, J = 8.7 Hz, 1H), 7.38 (s, 1H), 7.22 (s, 1H), 5.03 (s, 2H), 3.88 (t, J = 7.2 Hz, 2H), 3.78 (dt, J = 22.8, 8.9 Hz, 2H), 3.69-3.53 (m, 4H), 3.44 (s, 3H), 3.29 (t, J = 5.5 Hz, 2H), 3.12 (s, 2H), 2.60 (t, J = 5.4 Hz, 2H), 2.28 (s, 3H), 2.08-1.83 (m, 4H). |
| 34 | 2.9 | 40.8 | 117.9 | (DMSO-d$_6$) δ 12.71 (s, 1H), 10.10 (s, 1H), 8.62 (s, 1H), 8.18 (s, 1H), 7.79 (d, J = 8.8 Hz, 1H), 7.68 (d, J = 8.7 Hz, 1H), 4.92 (s, 2H), 3.75 (q, J = 6.7 Hz, 1H), 3.47 (s, 3H), 3.29 (t, J = 5.5 Hz, 2H), 3.06 (s, 2H), 2.63 (t, J = 5.5 Hz, 2H), 2.24 (s, 3H), 1.43 (d, J = 6.7 Hz, 6H). |

TABLE 1-continued

The results of enzymatic activity and cell activity tests

| Example No. | Enzymatic activity FGFR4 IC$_{50}$ (nM) | Cell activity | | $^1$H-NMR(400 MHz) |
|---|---|---|---|---|
| | | HuH-7 EC$_{50}$ (nM) | HuH-7 Absolute IC$_{50}$ (nM) | |
| 36 | 17.1 | 190.5 | 409.8 | (CDCl$_3$) δ 13.34 (s, 1H), 10.26 (s, 1H), 8.35 (s, 1H), 7.97 (d, J = 8.7 Hz, 2H), 7.30 (d, J = 8.8 Hz, 1H), 5.11 (s, 2H), 4.35 (t, J = 4.6 Hz, 2H), 3.88-3.79 (m, 2H), 3.52 (s, 3H), 3.48 (s, 3H), 3.45-3.30 (m, 2H), 3.30-3.08 (m, 2H), 2.82-2.56 (m, 2H), 2.47-2.29 (m, 3H). |
| 39 | 3.4 | 48.8 | 100.5 | (CDCl$_3$) δ 13.31 (s, 1H), 10.26 (s, 1H), 8.35 (s, 1H), 8.01 (d, J = 7.5 Hz, 1H), 7.90 (s, 1H), 7.32 (d, J = 8.7 Hz, 1H), 5.11 (s, 2H), 4.05 (d, J = 7.0 Hz, 2H), 3.52 (s, 3H), 3.51-3.37 (m, 2H), 3.36-3.16 (m, 2H), 2.79 (dt, J = 24.7, 13.8 Hz, 2H), 2.45 (s, 3H), 0.88 (t, J = 7.0 Hz, 1H), 0.75-0.63 (m, 2H), 0.42 (q, J = 5.3 Hz, 2H). |
| 51 | 1.4 | 27 | 65 | (CDCl$_3$) δ 12.94 (s, 1H), 10.25 (s, 1H), 8.16 (s, 1H), 7.91 (d, J = 8.6 Hz, 1H), 7.90 (s, 1H), 7.30 (d, J = 8.8 Hz, 1H), 5.28(s, 1H), 5.10 (s, 2H), 4.11 (q, J = 7.0 Hz, 2H), 3.38 (t, J = 5.5 Hz, 2H), 3.21 (s, 2H), 2.67 (t, J = 5.4 Hz, 2H), 2.36 (s, 3H), 1.36 (t, J = 7.0 Hz, 3H), 1.25 (s, 1H), 0.97 (q, J = 6.3 Hz, 2H), 0.69-0.65(m, 2H). |
| 52 | 16.3 | NA | NA | (CDCl$_3$): δ 11.21 (s, 1H), 10.19 (s, 1H), 8.11 (s, 1H), 8.07 (s, 1H), 7.92-7.90 (m, 2H), 7.47-7.45 (m, 1H), 3.58-3.50 (m, 1H), 2.65-2.63 (m, 1H), 2.00-1.97 (m, 2H), 1.50-1.47 (m, 2H), 1.03-0.98 (m, 2H), 0.71-0.68 (m, 2H); |
| 56 | 8.1 | 93 | 223 | (CDCl$_3$) δ 12.50 (s, 1H), 10.19 (s, 1H), 8.11 (s, 1H), 7.83 (d, J = 8.7 Hz, 1H), 7.79 (s, 1H), 7.21 (d, J = 8.5 Hz, 1H), 5.03 (s, 2H), 4.94 (s, 1H), 3.45 (s, 3H), 3.29 (t, J = 5.5 Hz, 2H), 3.13 (s, 2H), 2.60 (t, J = 5.5 Hz, 2H), 2.54 (s, 1H), 2.29 (s, 3H), 0.87 (d, J = 5.5 Hz, 2H), 0.59-0.55 (m, 2H). |
| 57 | NA | NA | NA | (CDCl$_3$) δ 12.22 (s, 1H), 10.19 (s, 1H), 7.83(s, 1H), 7.82 (d, J = 9.0 Hz, 1H), 7.75 (s, 1H), 7.25 (d, J = 8.6 Hz, 1H), 5.34 (s, 1H), 5.04 (s, 2H), 3.47 (s, 3H), 3.29 (t, J = 5.6 Hz, 2H), 3.13 (s, 2H), 2.59 (t, J = 5.5 Hz, 2H), 2.57-2.51 (m, 1H), 2.28 (s, 3H), 1.44-1.41 (m, 1H), 0.85-0.75 (m, 8H). |
| Positive compound | 7.3 | 237.8 | 1008 | (CDCl$_3$) δ 12.92 (s, 1H), 10.24 (s, 1H), 8.17 (d, J = 7.8 Hz, 2H), 7.59 (s, 1H), 7.31 (d, J = 8.6 Hz, 2H), 5.13 (s, 2H), 3.71 (d, J = 6.1 Hz, 2H), 3.65 (t, J = 5.1 Hz, 4H), 3.58-3.46 (m, 9H), 3.09 (s, 3H). |

Note
"NT", i.e., "Not Tested" means that the compound was not tested.
The positive compound was Example 24 of WO2016151499A1.

It can be seen from the enzymatic activity data of the compounds of specific examples that the compounds of the present invention have a strong inhibitory effect on FGFR4 kinase activity. It can be seen from the cell activity data of the compounds of specific examples that the compounds of the present invention have a strong inhibitory effect on the proliferation activity of HuH-7 cells highly expressing FGFR4.

All documents mentioned in the present application are hereby incorporated by reference in their entirety, just as each document is cited separately as a reference. In addition, it should be understood that various modifications and changes may be made by those skilled in the art after reading the above teachings of the present invention and these equivalent forms also fall within the scope defined by the claims appended hereto.

The invention claimed is:

1. A compound of formula (IIIa-3), a stereoisomer or pharmaceutically acceptable salt thereof:

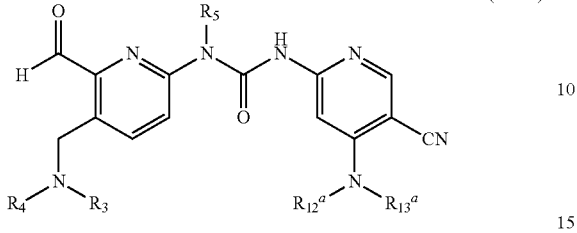

(IIIa-3)

wherein, $R_3$ and $R_4$, together with the nitrogen atom directly attached thereto, form a 5-6 membered heterocyclyl, above groups are further optionally substituted by one or more substituents selected from the group consisting of deuterium, fluorine, methyl, ethyl, isopropyl, cyclopropyl, oxa-cyclobutyl, =O, hydroxy, methoxy, ethoxy, amino and dimethylamino;

$R_5$ is selected from the group consisting of deuterium, $C_{1-4}$ alkyl, $C_{3-8}$ cycloalkyl and 3-8 membered heterocyclyl, above groups are further optionally substituted by one or more substituents selected from the group consisting of deuterium, halogen, cyano, $C_{1-4}$ alkyl, $C_{3-6}$ cycloalkyl, 3-6 membered heterocyclyl and $C_{1-4}$ alkoxy;

$R_{12}^a$ is hydrogen or deuterium, $R_{13}^a$ is selected from (i) $C_{1-8}$ alkyl, said $C_{1-8}$ alkyl is further substituted by one or more substituents selected from the group consisting of $C_{3-8}$ cycloalkyl, $C_{3-8}$ cycloalkyloxy, 3-8 membered heterocyclyl, and 3-8 membered heterocyclyloxy, said $C_{3-8}$ cycloalkyl, or 3-8 membered heterocyclyl is optionally further substituted by one or more substituents selected from the group consisting of deuterium, halogen, $C_{3-8}$ cycloalkyl, 3-8 membered heterocyclyl, hydroxy and $C_{1-4}$ alkoxy, or, (ii) $C_{3-10}$ cycloalkyl or 3-10 membered heterocyclyl, said $C_{3-10}$ cycloalkyl, or 3-10 membered heterocyclyl is optionally further substituted by one or more substituents selected from the group consisting of deuterium, halogen, hydroxy, $C_{1-4}$ alkyl, $C_{1-4}$ alkoxy, $C_{3-8}$ cycloalkyl, $C_{3-8}$ cycloalkyloxy, 3-8 membered heterocyclyl, and 3-8 membered heterocyclyloxy, said $C_{1-4}$ alkyl, $C_{3-8}$ cycloalkyl, or 3-8 membered heterocyclyl is optionally further more substituted by one or more substituents selected from the group consisting of deuterium, halogen, $C_{3-8}$ cycloalkyl, 3-8 membered heterocyclyl, hydroxy and $C_{1-4}$ alkoxy, or, $R_{12}^a$ and $R_{13}^a$, together with the nitrogen atom directly attached thereto, form a 4-10 membered heterocyclyl, above groups are further optionally substituted by one or more substituents selected from the group consisting of deuterium, halogen, hydroxy, $C_{1-4}$ alkyl, $C_{1-4}$ alkoxy, $C_{3-8}$ cycloalkyl, $C_{3-8}$ cycloalkyloxy, 3-8 membered heterocyclyl, and 3-8 membered heterocyclyloxy.

2. The compound of formula (IIIa-3), the stereoisomer or pharmaceutically acceptable salt thereof of claim 1, wherein the compound is selected from the following compounds:

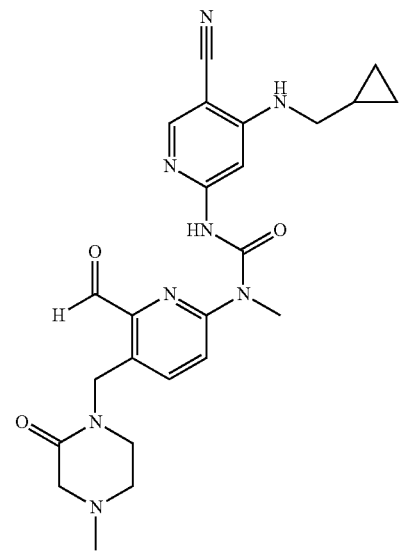 [SMILES: CN1CCN(Cc2ccc(N(C)C(=O)Nc3cc(NCC4CC4)c(C#N)cn3)nc2C=O)C(=O)C1]

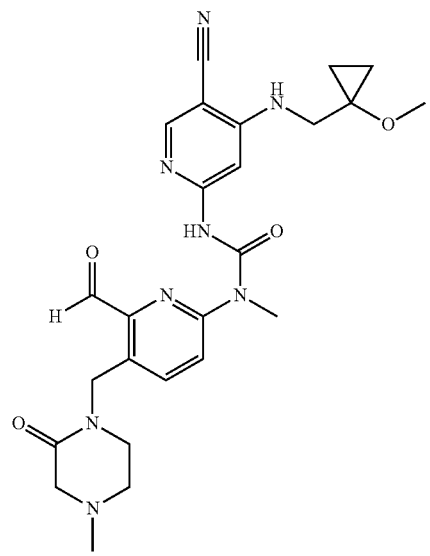

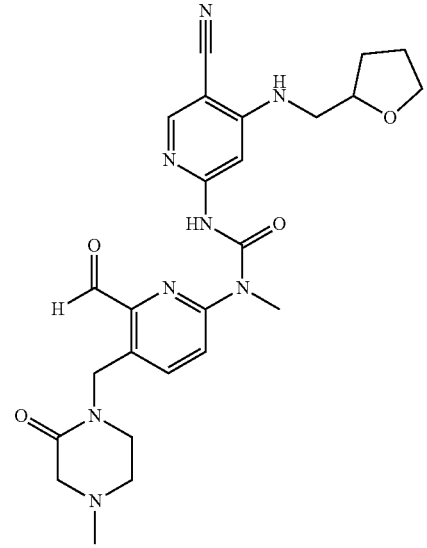

| 121 | 122 |
|---|---|
| -continued | -continued |
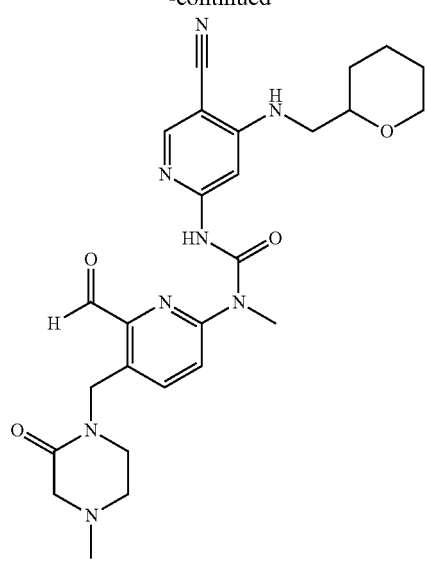
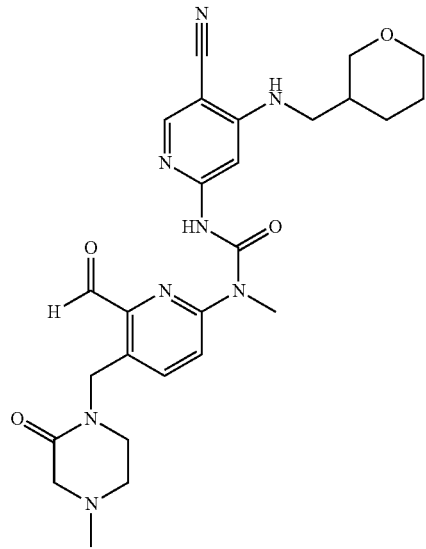
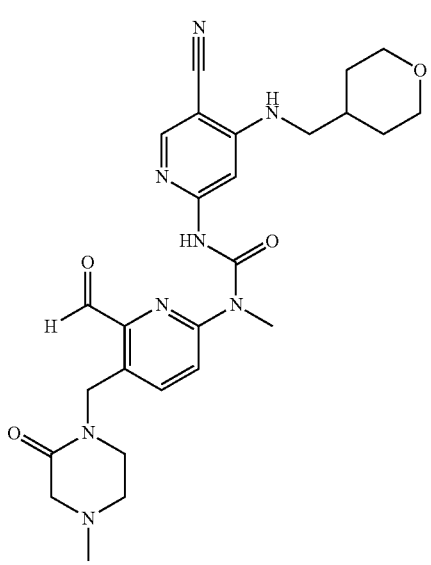

123
-continued
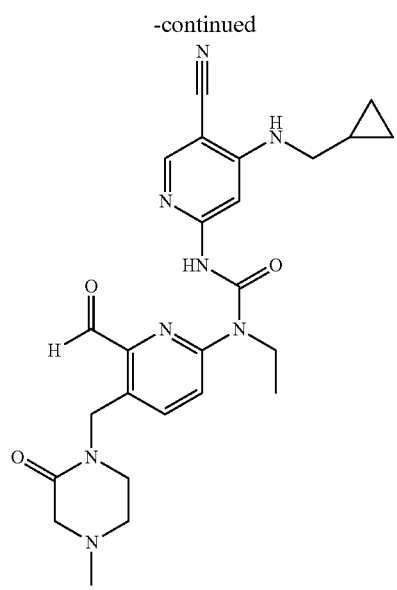
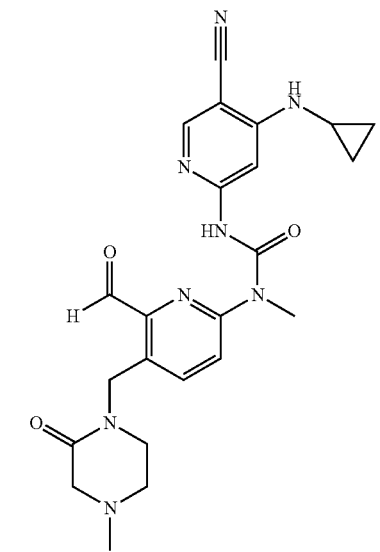
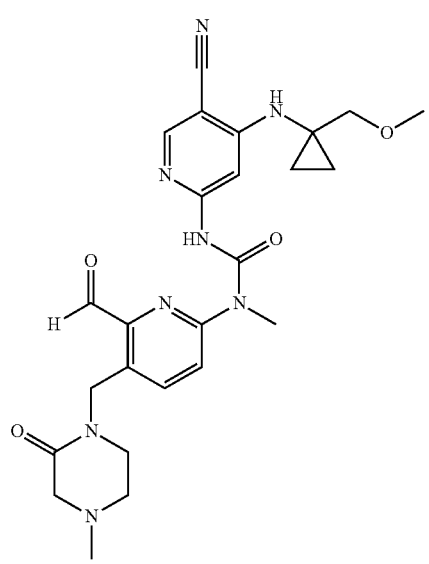
124
-continued
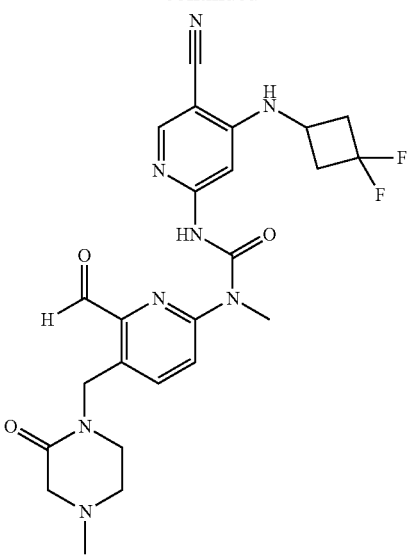
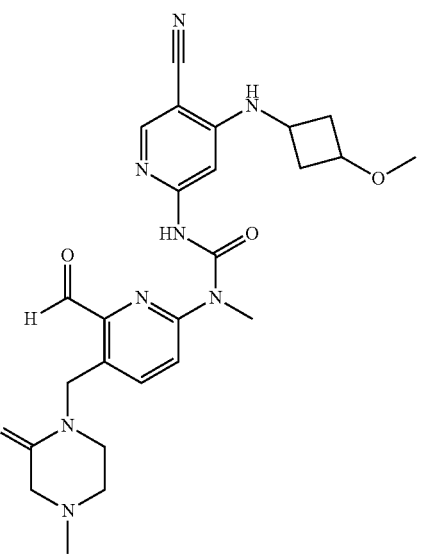

125
-continued

126
-continued

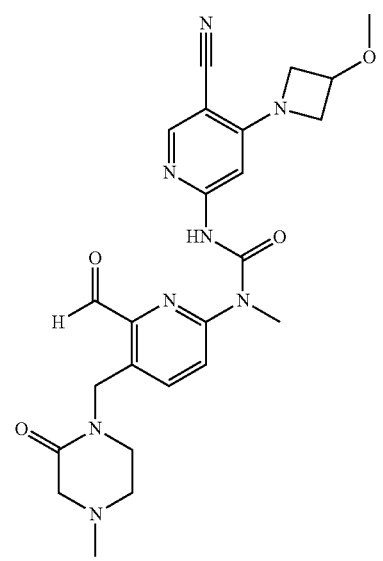
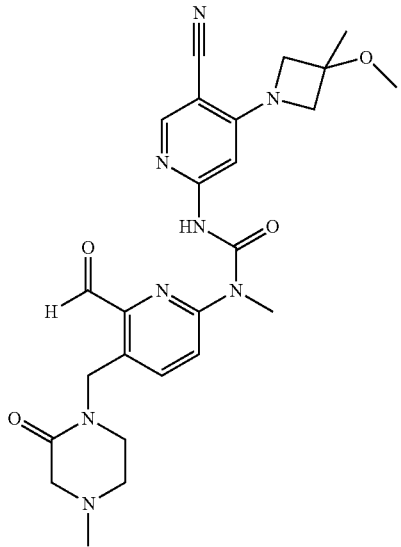
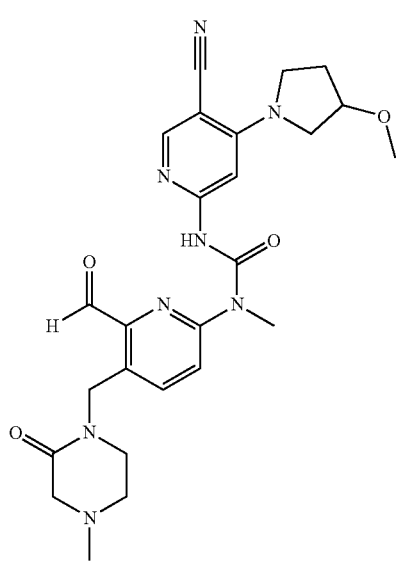
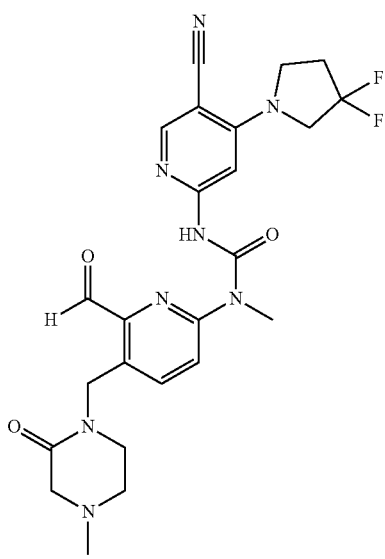
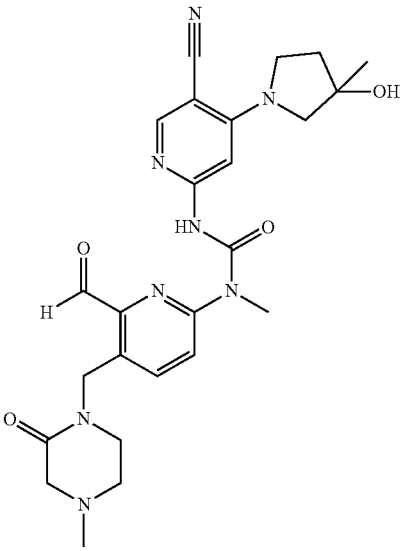
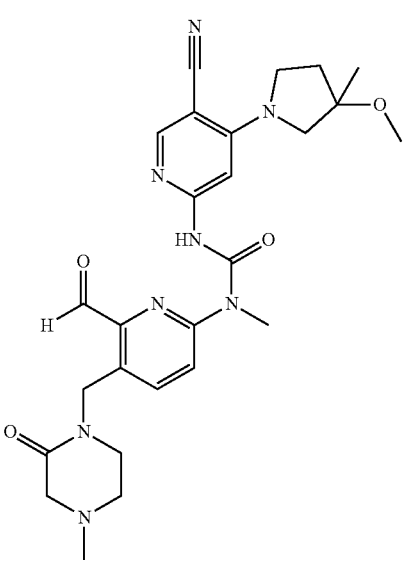

129
-continued
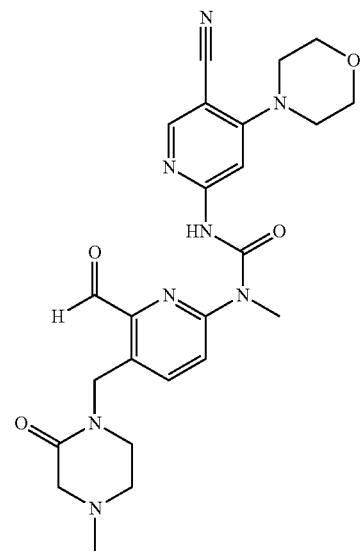
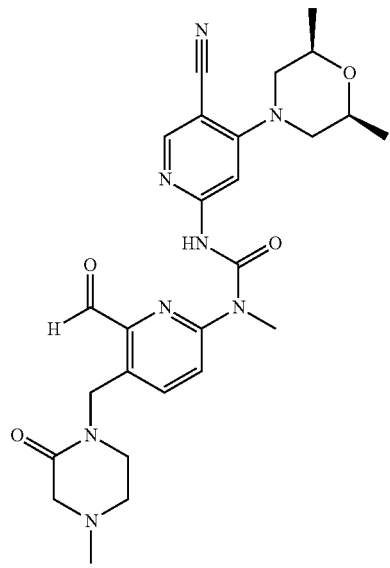
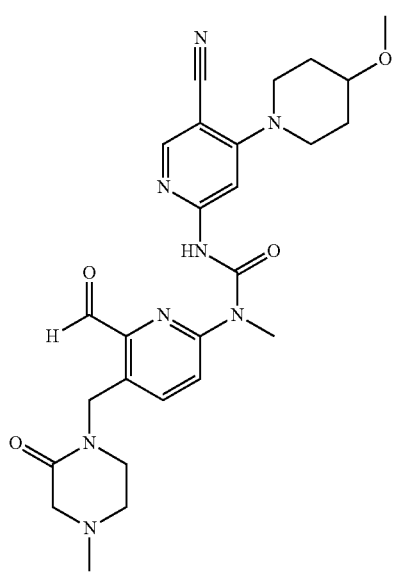
130
-continued
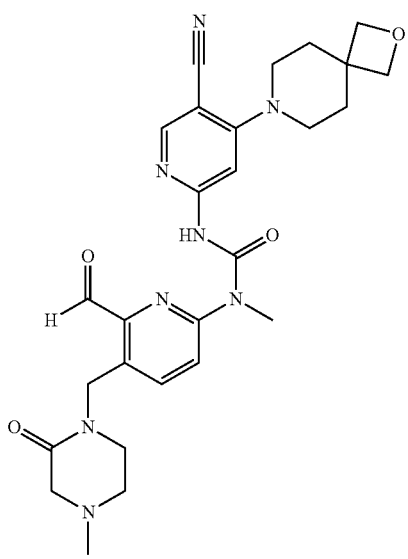
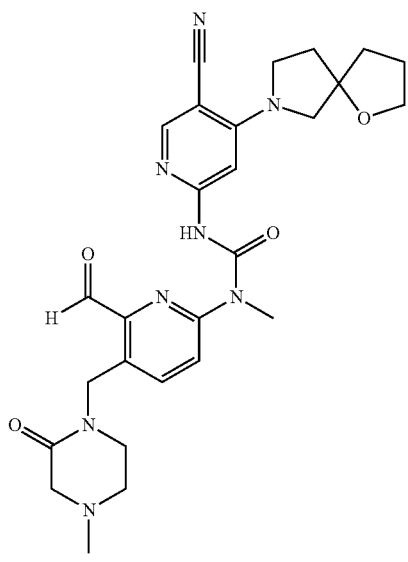
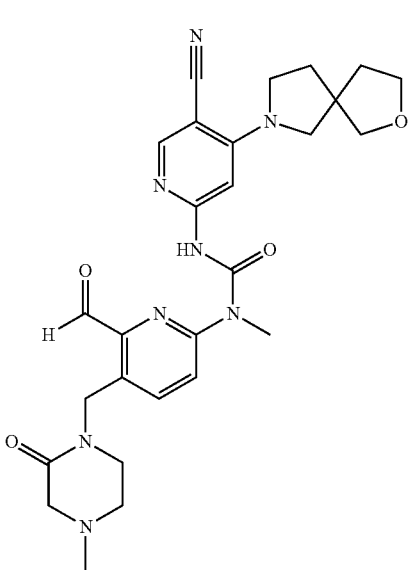

131
-continued
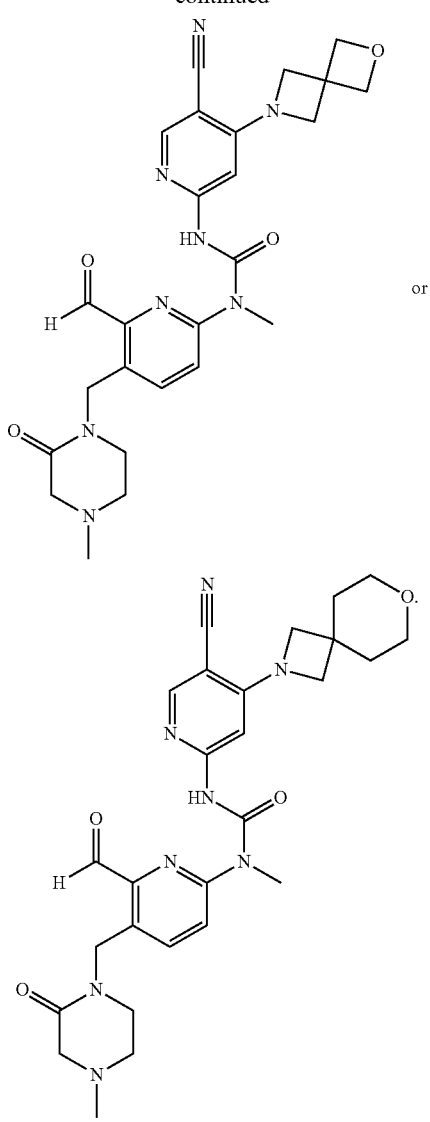
or
3. A process for preparing the compound of formula (IIIa-3), the stereoisomer or pharmaceutically acceptable salt thereof of claim 1, wherein, the process comprises the following steps:
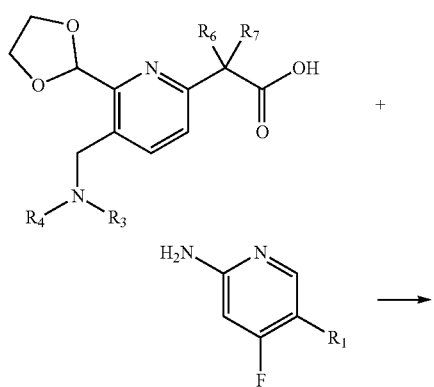
132
-continued
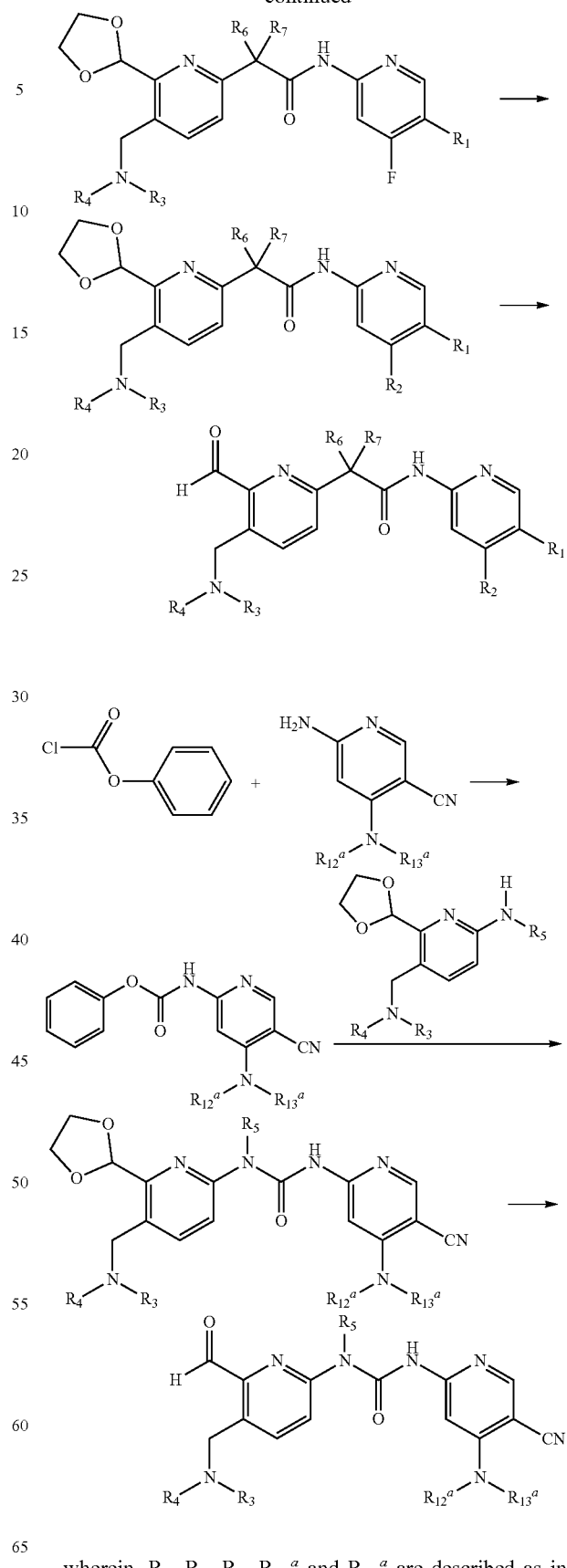
wherein, $R_3$, $R_4$, $R_5$, $R_{12}^a$ and $R_{13}^a$ are described as in claim 1.

4. A pharmaceutical composition comprising the compound of formula (IIIa-3), the stereoisomer or pharmaceutically acceptable salt thereof of claim 1, and pharmaceutically acceptable carrier.

5. A method for treating FGFR4 related cancer, comprising administering the compound of formula (IIIa-3), the stereoisomer or pharmaceutically acceptable salt thereof of claim 1 to a patient in need thereof; wherein said cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

6. A method for inhibiting FGFR4, comprising administering the compound of formula (IIIa-3), the stereoisomer or pharmaceutically acceptable salt thereof of claim 1 to a subject in need thereof.

\* \* \* \* \*